US012807623B2

(12) United States Patent
Luo et al.

(10) Patent No.: US 12,807,623 B2
(45) Date of Patent: Nov. 24, 2026

(54) PYRIMIDINE TRICYCLIC DERIVATIVE AND PHARMACEUTICAL APPLICATION THEREOF

(71) Applicant: CHIA TAI TIANQING PHARMACEUTICAL GROUP CO., LTD., Lianyungang (CN)

(72) Inventors: Yunfu Luo, Shanghai (CN); Guoli Zhang, Shanghai (CN); Shaolong Li, Shanghai (CN); Weizhi Ge, Shanghai (CN); Shuhui Chen, Shanghai (CN)

(73) Assignee: CHIA TAI TIANQING PHARMACEUTICAL GROUP CO., LTD., Lianyungang (CN)

( * ) Notice: Subject to any disclaimer, the term of this patent is extended or adjusted under 35 U.S.C. 154(b) by 325 days.

(21) Appl. No.: 18/699,531

(22) PCT Filed: Oct. 13, 2022

(86) PCT No.: PCT/CN2022/125047
§ 371 (c)(1),
(2) Date: Apr. 8, 2024

(87) PCT Pub. No.: WO2023/061432
PCT Pub. Date: Apr. 20, 2023

(65) Prior Publication Data

US 2024/0409560 A1 Dec. 12, 2024

(30) Foreign Application Priority Data

Oct. 13, 2021 (CN) .......................... 202111194177.6
Dec. 20, 2021 (CN) .......................... 202111565306.8
Sep. 22, 2022 (CN) .......................... 202211160959.2

(51) Int. Cl.
*C07D 471/16* (2006.01)
*A61K 31/519* (2006.01)
*C07D 519/00* (2006.01)

(52) U.S. Cl.
CPC .......... *C07D 519/00* (2013.01); *A61K 31/519* (2013.01)

(58) Field of Classification Search
CPC ... C07D 471/16; C07D 519/00; A61K 31/519
See application file for complete search history.

(56) References Cited

U.S. PATENT DOCUMENTS

2013/0172372 A1 7/2013 Follmann et al.
2014/0350020 A1 11/2014 Follmann et al.

FOREIGN PATENT DOCUMENTS

| | | | |
|---|---|---|---|
| CN | 103906752 | A | 7/2014 |
| CN | 104159899 | A | 11/2014 |
| CN | 107964018 | A | 4/2018 |
| CN | 108727340 | A | 11/2018 |
| CN | 108738320 | A | 11/2018 |
| JP | 2013532162 | A | 8/2013 |
| JP | 2013533250 | A | 8/2013 |
| JP | 2023523830 | A | 6/2023 |
| WO | 2017/121700 | A1 | 7/2017 |
| WO | 2021/219088 | A1 | 11/2021 |

OTHER PUBLICATIONS

Dec. 15, 2022 International Search Report issued in International Patent Application No. PCT/CN2022/125047.

*Primary Examiner* — Sikarl A Witherspoon
(74) *Attorney, Agent, or Firm* — Oliff PLC

(57) ABSTRACT

A pyrimidine tricyclic derivative and a pharmaceutical application thereof. Specifically disclosed are a compound as represented by formula (I), a stereoisomer thereof, and a pharmaceutically acceptable salt thereof.

(I)

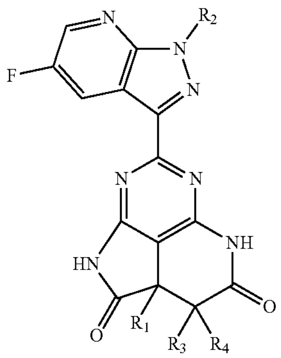

19 Claims, No Drawings

PYRIMIDINE TRICYCLIC DERIVATIVE AND PHARMACEUTICAL APPLICATION THEREOF

CROSS-REFERENCE TO RELATED APPLICATIONS

The present application claims 1) the priority and benefit to the Chinese Patent Application No. 2021111941776 filed with the China National Intellectual Property Administration on Oct. 13, 2021, 2) the priority and benefit to the Chinese Patent Application No. 2021115653068 filed with China National Intellectual Property Administration on Dec. 20, 2021, and 3) the priority and benefit to the Chinese Patent Application No. 2022111609592 filed with China National Intellectual Property Administration on Sep. 22, 2022, which are incorporated herein by reference in their entireties.

TECHNICAL FIELD

The present application relates to a pyrimidine tricyclic derivative and pharmaceutical use thereof, and in particular to a compound of formula (I), a stereoisomer thereof, and a pharmaceutically acceptable salt thereof.

BACKGROUND

Soluble guanylate cyclase (sGC), a heterodimer composed of α and β subunits, is widely found in the cytosol of mammals. Soluble guanylate cyclase is a key signal transduction enzyme in the NO-sGC-cGMP signaling pathway. sGC catalyzes the conversion of guanosine triphosphate (GTP) to cyclic guanosine monophosphate (cGMP) upon being activated in vivo. cGMP is an important secondary messenger molecule. It triggers a series of cascade reactions downstream by activating various effector molecules downstream, such as cGMP-dependent protein kinase G and cGMP-gated ion channels. It serves important physiological functions in the gastrointestinal system, the cardiovascular system, and the central nervous system, such as promoting vasodilation and the relaxation of smooth muscles, inhibiting platelet aggregation, vascular remodeling, apoptosis and inflammation, and taking part in neurotransmission. Under pathophysiological conditions, the NO/cGMP system may be suppressed, which may lead to, for example, hypertension, platelet activation, increased cell proliferation, endothelial dysfunction, arteriosclerosis, angina pectoris, heart failure, myocardial infarction, thrombosis, strokes, sexual dysfunction, etc. In recent two years, studies have shown that abnormality in the sGC-mediated signaling pathway is also closely related to the development of fibrotic diseases such as chronic kidney diseases and systemic sclerosis.

sGC stimulators have a dual mechanism of action: they can directly activate the sGC-cGMP signaling pathway without depending on NO but necessarily on $Fe^{2+}$-containing heme prosthetic groups; they can also heighten sGC's sensitivity to endogenous NO to produce a synergistic effect with NO. sGC stimulators are therefore heme-dependent and NO-independent. By stimulating sGC to generate more cGMP, a variety of important physiological processes can be regulated to promote the relaxation of vascular smooth muscles, inhibit platelet aggregation, etc. In addition, by activating sGC, other signaling pathways such as TGF-β can also be regulated to produce anti-fibrosis and anti-tumor effects. sGC stimulators can therefore be used as potential treatment means for cardiovascular diseases (heart failure, pulmonary hypertension, angina pectoris, and myocardial infarction) and fibrotic diseases (renal fibrosis and systemic sclerosis).

In response to the currently unmet market and clinical needs for such soluble guanylate cyclase stimulators, the present application provides a class of new compounds. Such compounds can be used as stimulators of soluble guanylate cyclase. They have excellent in vitro stimulating activity for soluble guanylate cyclase and have good pharmacokinetic properties.

SUMMARY

The present application provides a compound of formula (I), a stereoisomer thereof, or a pharmaceutically acceptable salt thereof, (I)

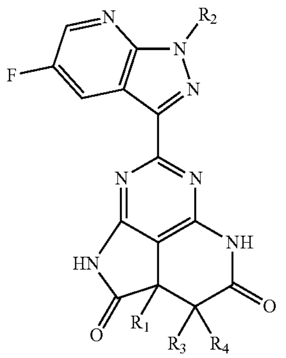

wherein, $R_1$ is selected from the group consisting of H, —OH, $C_{1-3}$ alkyl, $C_{1-3}$ alkoxy, and $C_{1-3}$ alkylamino;

$R_2$ is selected from the group consisting of benzyl and $C_{1-8}$ alkyl, the benzyl or $C_{1-8}$ alkyl being optionally substituted with 1, 2, 3, 4, or 5 halogen atoms;

$R_3$ and $R_4$ are each independently selected from the group consisting of H and $C_{1-3}$ alkyl; or $R_3$, $R_4$, and an atom to which they are both connected form $C_{3-6}$ cycloalkyl;

provided that the compound is not selected from the group consisting of the following structures, stereoisomers thereof, or pharmaceutically acceptable salts thereof:

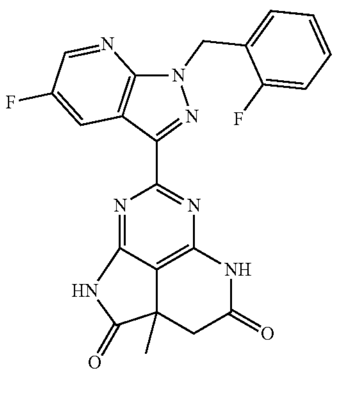

-continued

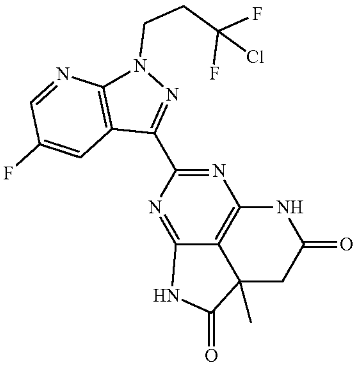

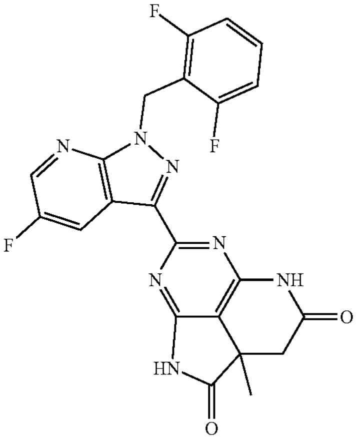

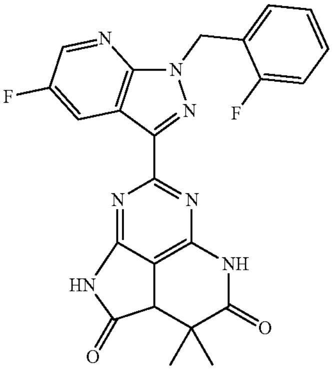

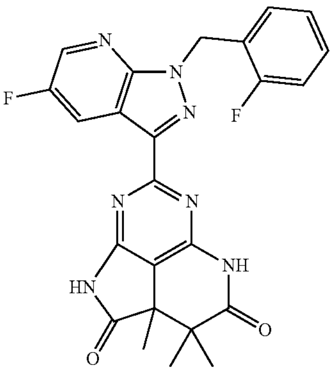

-continued

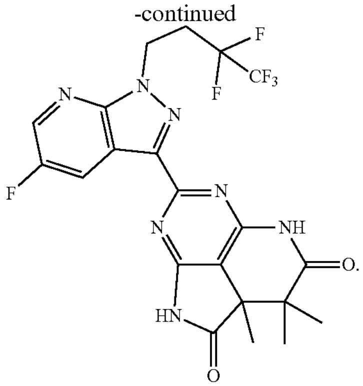

In some embodiments of the present application, $R_1$ is selected from the group consisting of H, —OH, $C_{1-3}$alkyl, and $C_{1-3}$ alkoxy, and the other variables are as defined herein.

In some embodiments of the present application, $R_1$ is selected from the group consisting of H, —OH, methyl, ethyl, n-propyl, isopropyl, methoxy, ethoxy, n-propoxy, and isopropoxy, and the other variables are as defined herein.

In some embodiments of the present application, $R_1$ is selected from the group consisting of H, OH, methyl, and methoxy, and the other variables are as defined herein.

In some embodiments of the present application, $R_2$ is selected from the group consisting of benzyl and $C_{1-6}$ alkyl, the benzyl or $C_{1-6}$ alkyl being optionally substituted with 1, 2, 3, 4, or 5 halogen atoms, and the other variables are as defined herein.

In some embodiments of the present application, $R_2$ is selected from the group consisting of benzyl and $C_{1-4}$ alkyl, the benzyl or $C_{1-4}$ alkyl being optionally substituted with 1, 2, 3, 4, or 5 halogen atoms, and the other variables are as defined herein.

In some embodiments of the present application, $R_2$ is selected from the group consisting of benzyl and $C_{1-4}$ alkyl, the benzyl or $C_{1-4}$ alkyl being optionally substituted with 1, 2, 3, 4, or 5 F, Cl, or Br atoms, and the other variables are as defined herein.

In some embodiments of the present application, $R_2$ is selected from the group consisting of benzyl and $C_{1-4}$ alkyl, the benzyl or $C_{1-4}$ alkyl being optionally substituted with 1, 2, 3, 4, or 5 F atoms, and the other variables are as defined herein.

In some embodiments of the present application, $R_2$ is selected from $C_{1-4}$ alkyl, the $C_{1-4}$ alkyl being optionally substituted with 1, 2, 3, 4, or 5 halogen atoms, and the other variables are as defined herein.

In some embodiments of the present application, $R_2$ is selected from $C_{1-4}$ alkyl, the $C_{1-4}$ alkyl being optionally substituted with 1, 2, 3, 4, or 5 F, Cl, or Br atoms, and the other variables are as defined herein.

In some embodiments of the present application, $R_2$ is selected from $C_{1-4}$ alkyl, the $C_{1-4}$ alkyl being optionally substituted with 1, 2, 3, 4, or 5 F atoms, and the other variables are as defined herein.

In some embodiments of the present application, $R_2$ is selected from the group consisting of benzyl and n-butyl, the benzyl being substituted with 1 fluorine atom and the n-butyl being substituted with 5 fluorine atoms, and the other variables are as defined herein.

In some embodiments of the present application, $R_2$ is selected from the group consisting of

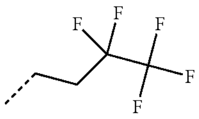 and 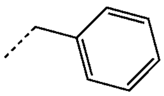, the other variables are as defined herein.

In some embodiments of the present application, $R_3$ and $R_4$ are each independently selected from the group consisting of H, methyl, ethyl, n-propyl, and isopropyl, or $R_3$, $R_4$, and an atom to which they are both connected form cyclopropyl, and the other variables are as defined herein.

In some embodiments of the present application, $R_3$ and $R_4$ are each independently selected from the group consisting of H and methyl, or $R_3$, $R_4$, and an atom to which they are both connected form cyclopropyl, and the other variables are as defined herein.

In some embodiments of the present application, the structural unit

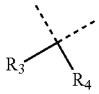

described above is selected from the group consisting of

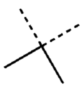, 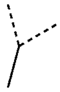, and 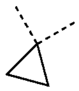, and the other variables are as defined herein.

Some other embodiments of the present application are derived from any combination of the variables described above.

The present application also provides a compound selected from the group consisting of the following, a stereoisomer thereof, or a pharmaceutically acceptable salt thereof:

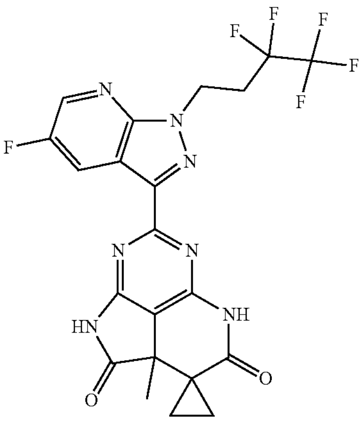

-continued

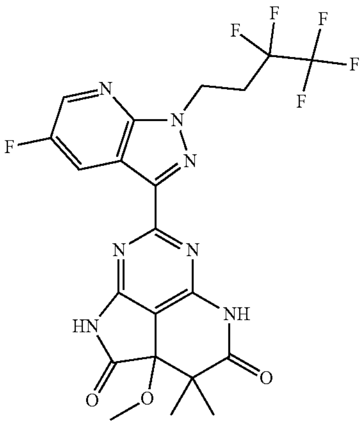

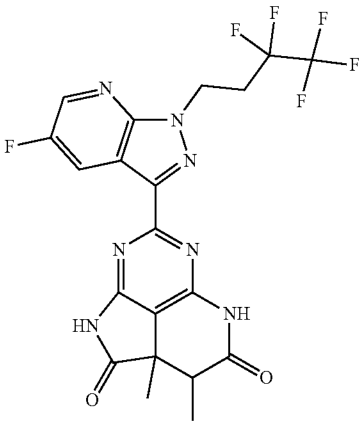

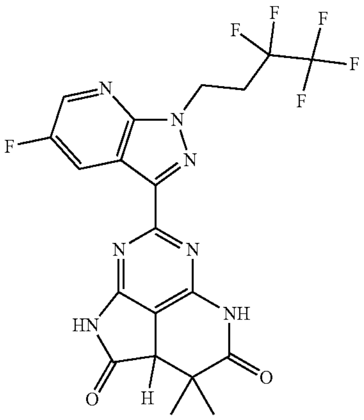

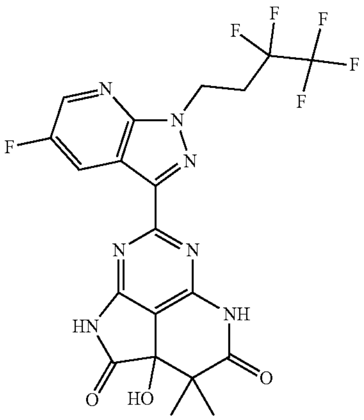

-continued
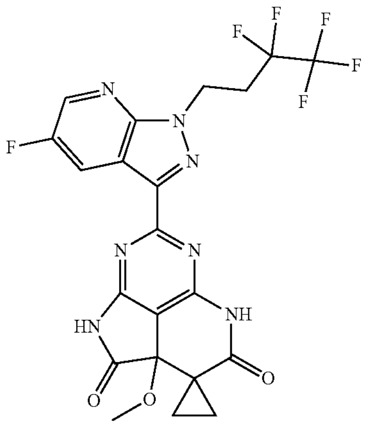
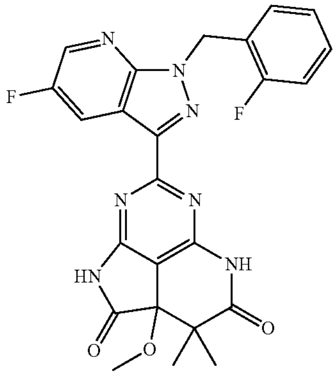
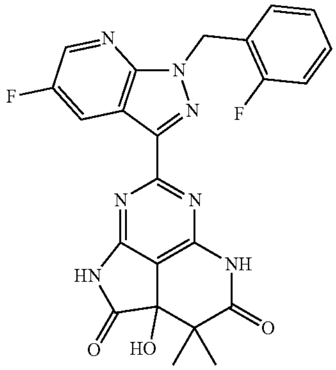
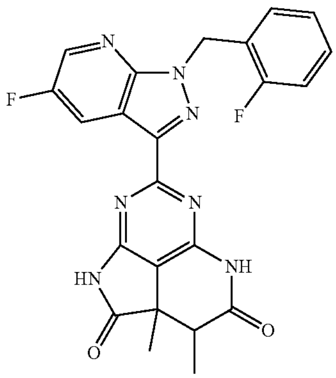
-continued
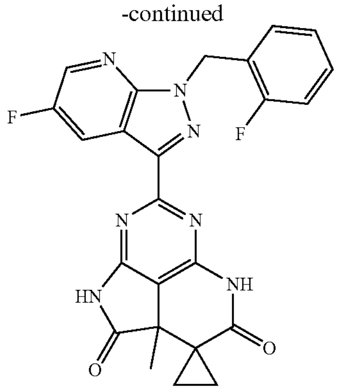
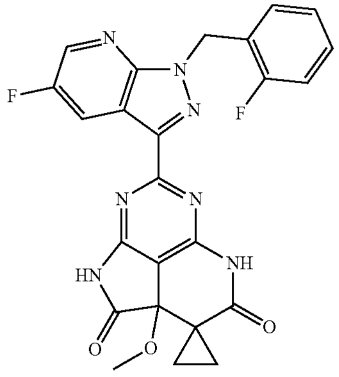
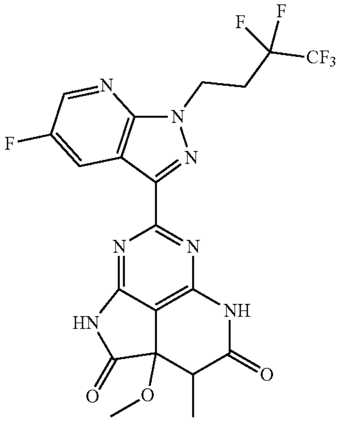
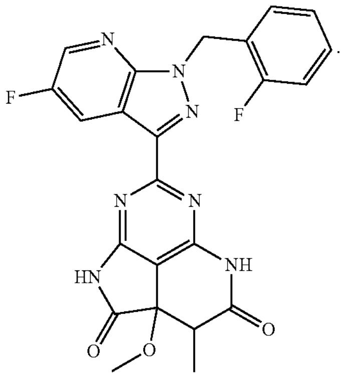 [SMILES: COC12C(=O)Nc3nc(-c4nn(Cc5ccccc5F)c5ncc(F)cc45)nc(c31)NC(=O)C2C]
The present application also provides a compound selected from the group consisting of the following, a stereoisomer thereof, or a pharmaceutically acceptable salt thereof:

-continued
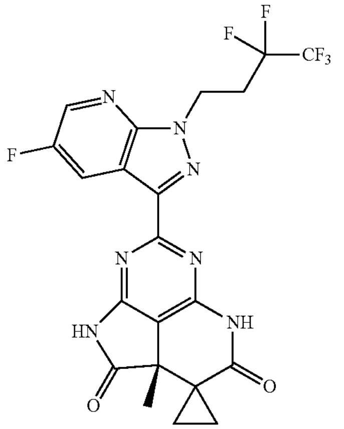
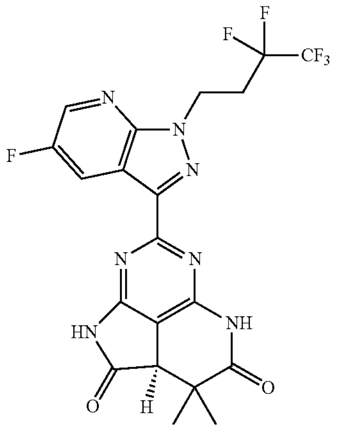
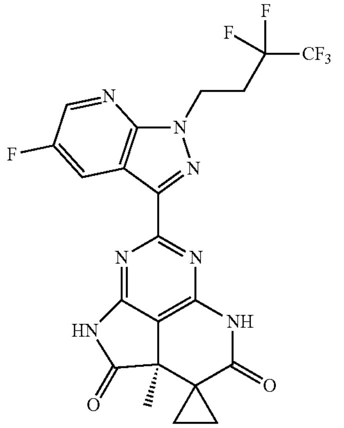
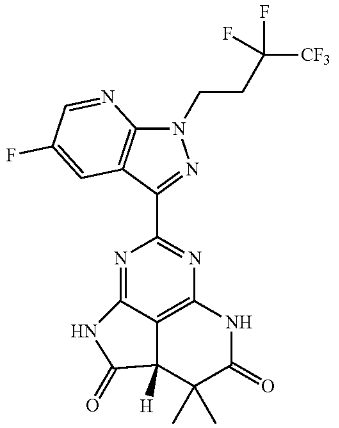
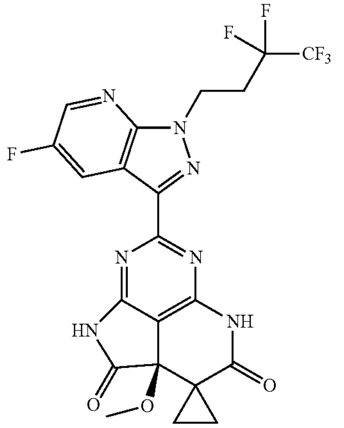
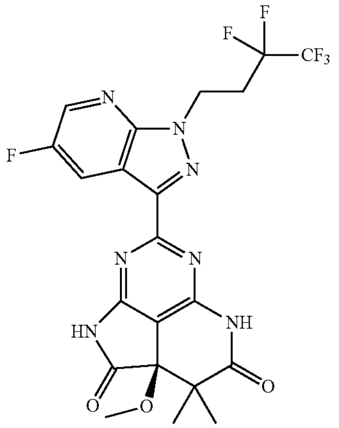
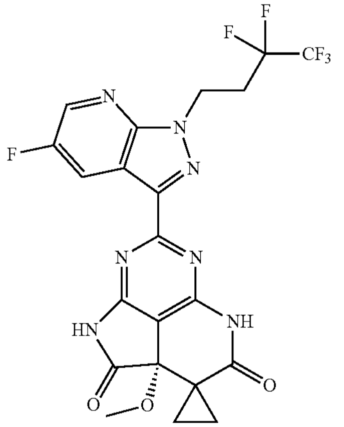
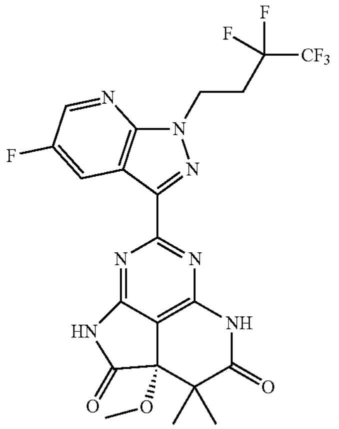

-continued
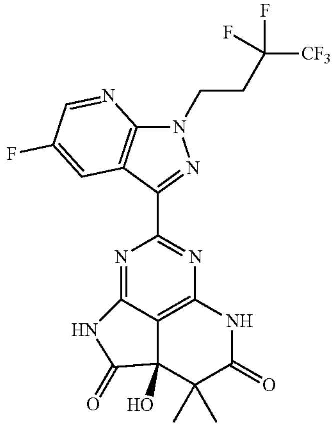
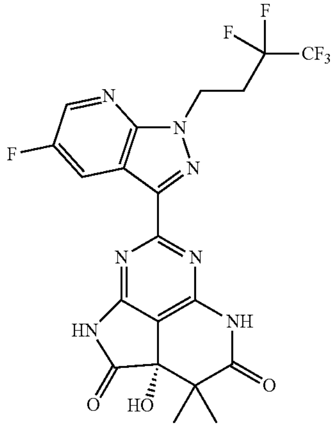
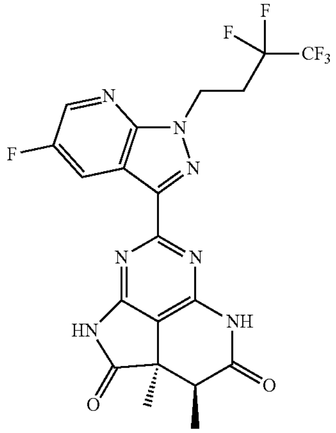
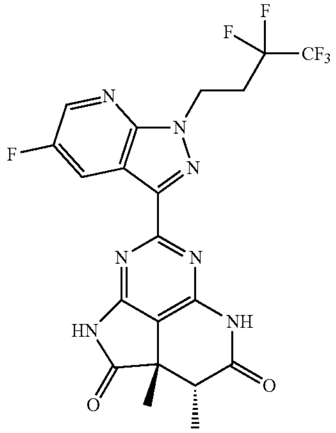
-continued
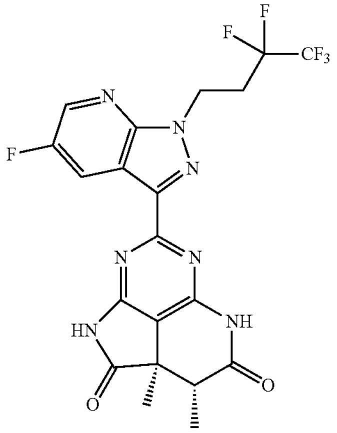
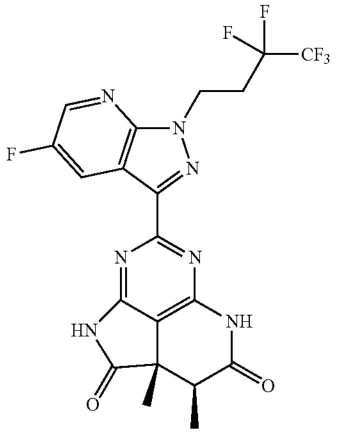
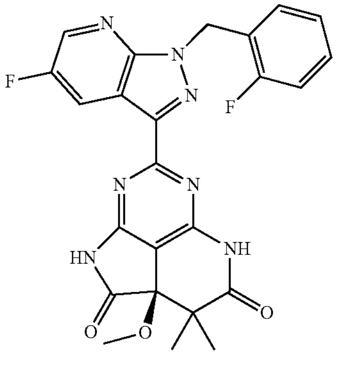
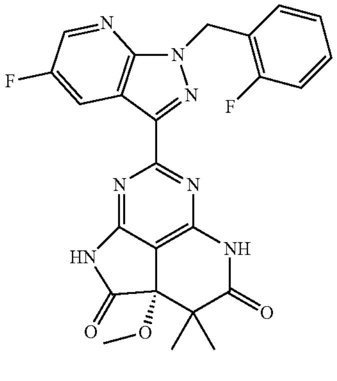

-continued
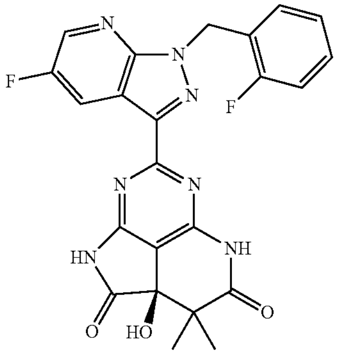
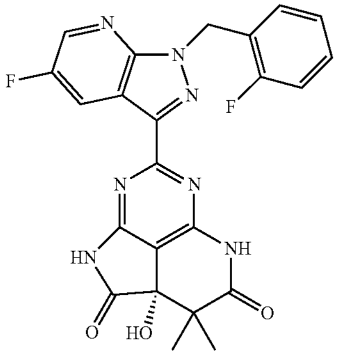
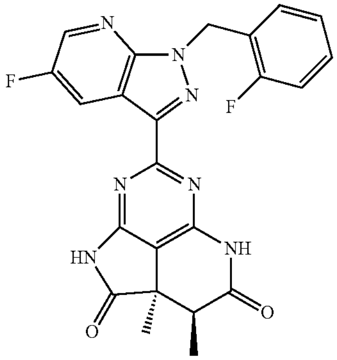
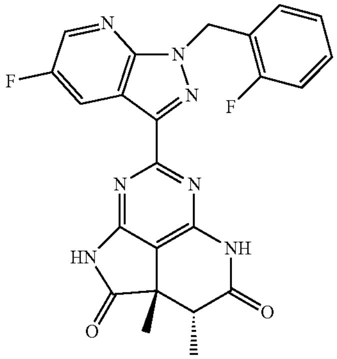
-continued
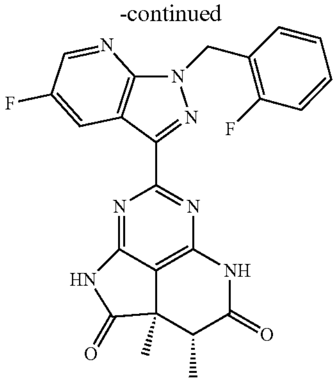
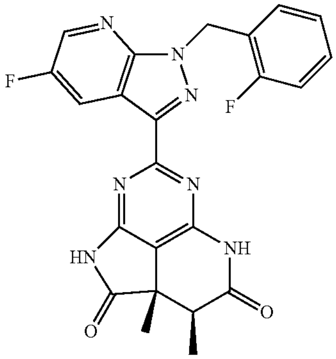
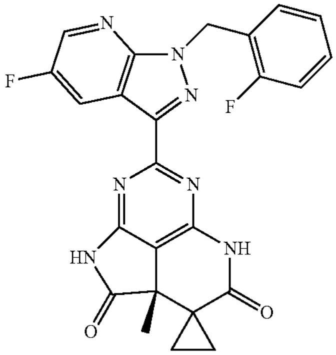
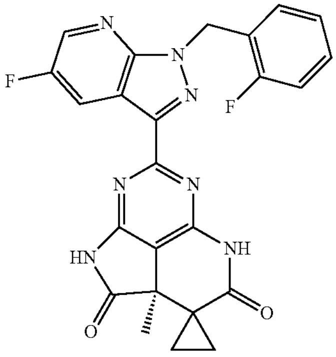

-continued
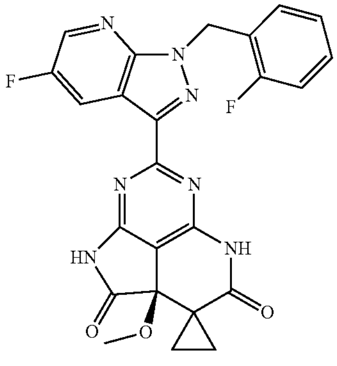
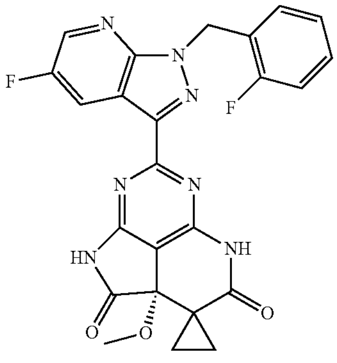
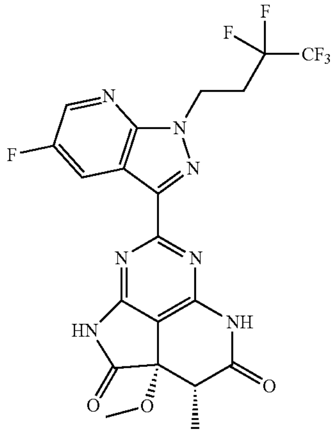
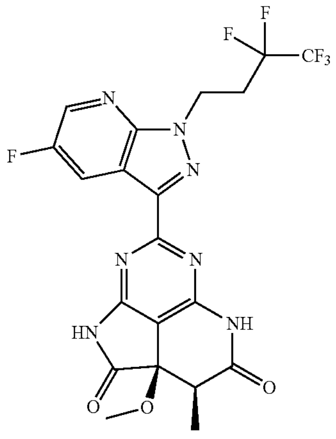
-continued
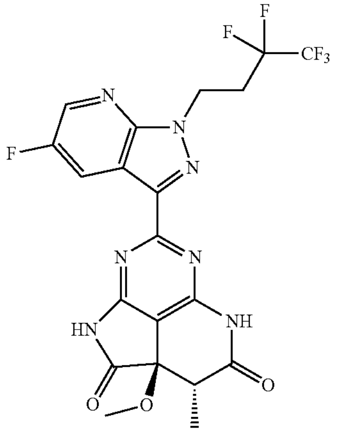
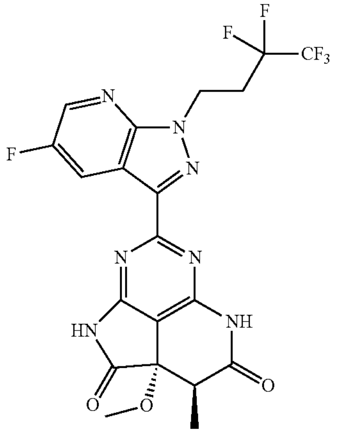
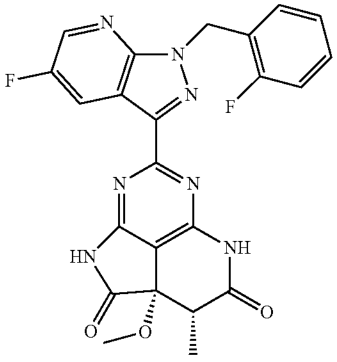
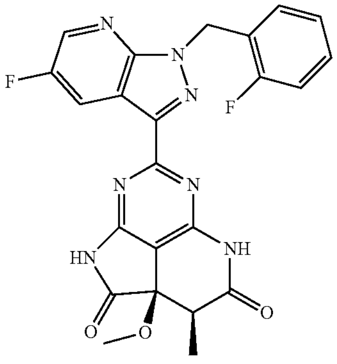

-continued

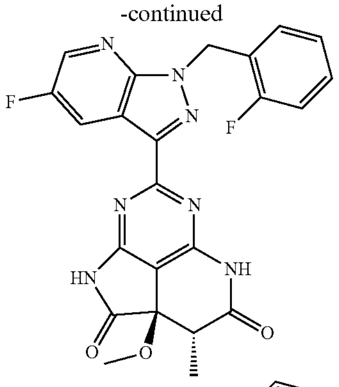

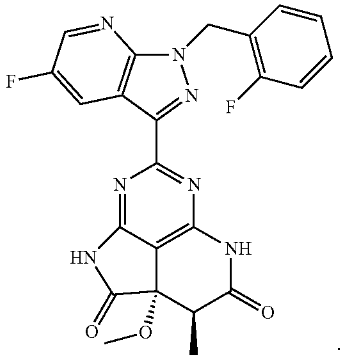

In another aspect, the present application provides a pharmaceutical composition comprising the compound, the stereoisomer thereof, or the pharmaceutically acceptable salt thereof disclosed herein. In some embodiments, the pharmaceutical composition disclosed herein further comprises a pharmaceutically acceptable excipient.

In another aspect, the present application provides use of the compound, the stereoisomer thereof, or the pharmaceutically acceptable salt thereof, or the pharmaceutical composition thereof described above, for preparing a medicament for treating an sGC agonist or stimulator-associated disease.

In another aspect, the present application provides a method for treating an sGC agonist or stimulator-associated disease in a mammal, which comprises administering to the mammal, preferably a human, in need of the treatment a therapeutically effective amount of the compound, the stereoisomer thereof, or the pharmaceutically acceptable salt thereof, or the pharmaceutical composition thereof disclosed herein.

In another aspect, the present application provides use of the compound, the stereoisomer thereof, or the pharmaceutically acceptable salt thereof, or the pharmaceutical composition thereof disclosed herein for treating an sGC agonist or stimulator-associated disease.

In another aspect, the present application provides the compound, the stereoisomer thereof, or the pharmaceutically acceptable salt thereof, or the pharmaceutical composition thereof disclosed herein for use in treating an sGC agonist or stimulator-associated disease.

In some embodiments of the present application, the sGC agonist or stimulator-associated disease is selected from the group consisting of heart failure and hypertension.

Technical Effects

The compound disclosed herein can effectively stimulate sGC, significantly improve the cGMP level, and has good apparent volume of distribution and half-life, good distribution in the heart, and no risk of entering the brain.

Definitions and Explanations

Unless otherwise stated, the following terms and phrases used herein are intended to have the following meanings. A particular term or phrase, unless otherwise specifically defined, should not be considered indefinite or unclear, but construed according to its common meaning. When referring to a trade name, it is intended to refer to its corresponding commercial product or its active ingredient.

The term "pharmaceutically acceptable" is used herein for those compounds, materials, compositions, and/or dosage forms that are, within the scope of sound medical judgment, suitable for use in contact with the tissues of human beings and animals without excessive toxicity, irritation, allergic response, or other problems or complications, and commensurate with a reasonable benefit/risk ratio.

The term "pharmaceutically acceptable salt" refers to a salt of the compound disclosed herein, which is prepared from the compound having particular substituents discovered by the present application and a relatively nontoxic acid or base. When the compound disclosed herein contains a relatively acidic functional group, a base addition salt can be obtained by allowing such a compound to be in contact with a sufficient amount of a base in a pure solution or a suitable inert solvent. When the compound disclosed herein contains a relatively basic functional group, an acid addition salt can be obtained by allowing such a compound to be in contact with a sufficient amount of an acid in a pure solution or a suitable inert solvent. Certain specific compounds disclosed herein contain both basic and acidic functional groups that allow the compounds to be converted into either base or acid addition salt.

The pharmaceutically acceptable salts disclosed herein can be synthesized from a parent compound having an acidic or basic group using conventional chemical methods. In general, such salts are prepared by subjecting the compounds in a free acid or base form to a reaction with a stoichiometric amount of appropriate base or acid in water or an organic solvent or a mixture thereof.

Unless otherwise stated, the term "isomer" is intended to include geometric isomers, cis-trans isomers, stereoisomers, enantiomers, optical isomers, diastereoisomers, and tautomers.

The compounds disclosed herein can be in the form of a geometric isomer or stereoisomer. All such compounds are contemplated herein, including cis- and trans-isomers, (−)- and (+)-enantiomers, (R)- and (S)-enantiomers, diastereoisomers, (D)-isomers, (L)-isomers, and racemic mixtures and other mixtures thereof, such as an enantiomer or diastereoisomer enriched mixture, all of which are encompassed within the scope of the present application. The substituents such as alkyl may have an additional asymmetric carbon atom. All these isomers and mixtures thereof are encompassed within the scope of the present application.

Unless otherwise stated, the term "enantiomer" or "optical isomer" refers to stereoisomers that are mirror images of each other.

Unless otherwise stated, the term "cis-trans isomer" or "geometric isomer" results from the inability of a single bond of a ring carbon atom or a double bond to rotate freely.

Unless otherwise stated, the term "diastereoisomer" refers to stereoisomers in which molecules each have two or more chiral centers and are not mirror images of each other.

Unless otherwise stated, "(+)" stands for dextrorotation, "(−)" stands for levorotation, and "(±)" stands for racemization.

Unless otherwise stated, the absolute configuration of a stereogenic center is represented by a wedged solid bond ( ) and a wedged dashed bond ( ), and the relative configuration of a stereogenic center is represented by a straight solid bond ( ) and a straight dashed bond ( ). A wavy line ( ) represents a wedged solid bond ( ) or a wedged dashed bond ( ), or a wavy line ( ) represents a straight solid bond ( ) or a straight dashed bond ( ).

Unless otherwise stated, the term "enriched with one isomer", "isomer enriched", "enriched with one enantiomer", or "enantiomer enriched" means that the content of one of the isomers or enantiomers is less than 100% and more than or equal to 60%, or more than or equal to 70%, or more than or equal to 80%, or more than or equal to 90%, or more than or equal to 95%, or more than or equal to 96%, or more than or equal to 97%, or more than or equal to 98%, or more than or equal to 99%, or more than or equal to 99.5%, or more than or equal to 99.6%, or more than or equal to 99.7%, or more than or equal to 99.8%, or more than or equal to 99.9%.

Unless otherwise stated, the term "isomeric excess" or "enantiomeric excess" refers to the difference between the relative percentages of two isomers or enantiomers. For example, if the content of one of the isomers or enantiomers is 90% and the content of the other isomer or enantiomer is 10%, the isomeric or enantiomeric excess (ee) is 80%.

Optically active (R)- and (S)-isomers and D and L isomers can be prepared by chiral synthesis or chiral reagents or other conventional techniques. An enantiomer of a certain compound disclosed herein can be prepared by asymmetric synthesis or derivatization using a chiral additive, wherein the resulting diastereoisomeric mixture is separated and the auxiliary group is cleaved so as to provide the desired pure enantiomer. Alternatively, when the molecule contains a basic functional group (such as amino) or an acidic functional group (such as carboxyl), the compound reacts with an appropriate optically active acid or base to form a salt of the diastereoisomer, which is then subjected to diastereoisomeric resolution through conventional methods in the art to give the pure enantiomer. Furthermore, the enantiomer and the diastereoisomer are generally isolated through chromatography using a chiral stationary phase, optionally in combination with chemical derivatization (e.g., carbamate generated from amines).

The compound disclosed herein may contain an unnatural proportion of atomic isotope at one or more of the atoms that constitute the compound. For example, the compound may be labeled with a radioisotope, such as tritium ($^3H$), iodine-125 ($^{125}I$), or C-14 ($^{14}C$). For another example, hydrogen can be substituted with deuterium to form a deuterated drug, and the bond formed by deuterium and carbon is firmer than that formed by common hydrogen and carbon. Compared with an un-deuterated drug, the deuterated drug has the advantages of reduced toxic side effects, increased stability, enhanced efficacy, prolonged biological half-life, and the like. All isotopic variations of the compound disclosed herein, whether radioactive or not, are encompassed within the scope of the present application.

The term "optional" or "optionally" means that the subsequently described event or circumstance may, but not necessarily, occur, and the description includes instances where the event or circumstance occurs and instances where it does not.

The term "substituted" means that one or more hydrogen atoms on a specific atom are substituted with substituents, wherein the substituents may include deuterium and hydrogen variants, as long as the valence of the specific atom is normal and the substituted compound is stable. When the substituent is oxygen (i.e., =O), it means that two hydrogen atoms are substituted. Substitution with oxygen does not occur on aromatic groups. The term "optionally substituted" means that an atom can be or cannot be substituted with a substituent. Unless otherwise specified, the type and number of the substituent may be arbitrary as long as being chemically achievable.

When any variable (e.g., R) occurs once or more in the constitution or structure of a compound, the definition of the variable in each case is independent. Thus, for example, if a group is substituted with 0-2 R, the group can be optionally substituted with up to two R, and the definition of R in each case is independent. Furthermore, a combination of the substituent and/or the variant thereof is permissible only if the combination can result in a stable compound.

When the number of a connecting group is 0, for example, $-(CRR)_0-$, it means that the connecting group is a single bond.

When the number of a substituent is 0, it means that the substituent does not exist. For example, $-A-(R)_0$ means that the structure is actually -A.

When a substituent is absent, it means that the substituent does not exist. For example, when X is absent in A-X, the structure of A-X is actually A.

When one of the variables is selected from a single bond, it means that the two groups linked by the single bond are connected directly. For example, in A-L-Z, when L represents a single bond, it means that the structure is actually A-Z.

When a bond of a substituent is cross-connected to two or more atoms on a ring, the substituent can be bonded to any atom on the ring. For example, the structural unit

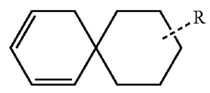
or
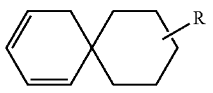

represents that the substitution with substituent R may occur in any one position on cyclohexyl or cyclohexadienyl. When it is not specified by which atom the listed substituent is linked to the group to be substituted, the substituent can be linked via any atom of the group. For example, pyridinyl as a substituent can be linked to the group to be substituted through any carbon atom on the pyridine ring.

When the direction for connection of the listed connecting group is not specified, the direction for connection is arbitrary. For example, when the connecting group L contained in

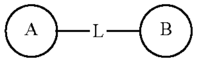

is -M-W—, -M-W— can either connect ring A and ring B in a direction same as left-to-right reading order to form

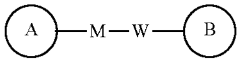
, or connect ring A and ring B in a direction opposite to the left-to-right reading order to form

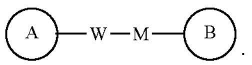

A combination of the connecting group, the substituent, and/or the variant thereof is permissible only if the combination can result in a stable compound.

Unless otherwise specified, when a group has one or more connectable sites, any one or more of the sites of the group may be connected to other groups by chemical bonds. If there is no designated connecting mode for chemical bonds and H atoms are present at a connectable site, when the connectable site is connected to chemical bonds, the number of the H atoms at the connectable site is correspondingly reduced based on the number of the connected chemical bonds, so that the resulting groups have corresponding valences. The chemical bond that connects the site and another group may be represented by a straight solid bond (), a straight dashed bond (), or a wavy line ().

For example, the straight solid bond in —$OCH_3$, refers to being connected to another group via the oxygen atom in the group; the straight dashed bond in

refers to being connected to another group via two ends of the nitrogen atom in the group; the wavy line in

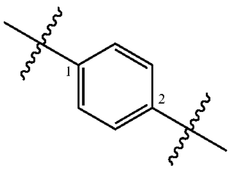 [SMILES: *c1ccc(*)cc1]

refers to being connected to another group via the carbon atoms at positions 1 and 2 in the phenyl group;

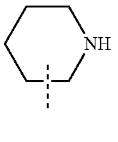

means that any connectable site on the piperidinyl can be connected to another group via 1 chemical bond in at least 4 connecting modes:

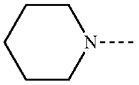, 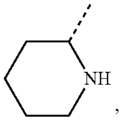, 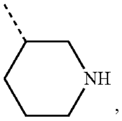, and 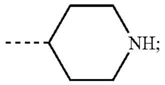

even if —N— is connected with an H atom,

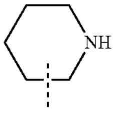

includes the connection mode of

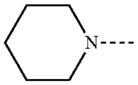, but when 1 chemical bond is connected to a site, the number of H at that site is correspondingly reduced by 1 and a monovalent piperidinyl is thus formed.

Unless otherwise specified, the term "alkyl" refers to a linear or branched saturated hydrocarbon group. In some embodiments, the alkyl is $C_{1-8}$ alkyl. In other embodiments, the alkyl is $C_{1-4}$ alkyl. In still other embodiments, the alkyl is $C_{1-3}$ alkyl. The alkyl may be monosubstituted (e.g., —$CH_2F$) or polysubstituted (e.g., —$CF_3$), and may be monovalent (e.g., methyl), divalent (e.g., methylene), or polyvalent (e.g., methenyl). Examples of alkyl include, but are not limited to, methyl (Me), ethyl (Et), propyl (including n-propyl and isopropyl), butyl (including n-butyl, isobutyl, s-butyl, and t-butyl), pentyl (including n-pentyl, isopentyl, and neopentyl), hexyl, and the like.

Unless otherwise specified, the term "$C_{1-4}$ alkyl" refers to a linear or branched saturated hydrocarbon group consisting of 1 to 4 carbon atoms. The $C_{1-4}$ alkyl includes, but is not limited to, $C_{1-2}$ alkyl, $C_{1-3}$ alkyl, $C_{2-3}$ alkyl, and the like, and may be monovalent (e.g., methyl), divalent (e.g., methylene), or polyvalent (e.g., methenyl). Examples of $C_{1-4}$ alkyl include, but are not limited to, methyl (Me), ethyl (Et), propyl (including n-propyl and isopropyl), butyl (including n-butyl, isobutyl, s-butyl, and t-butyl), and the like.

Unless otherwise specified, the term "$C_{1-3}$ alkyl" refers to a linear or branched saturated hydrocarbon group consisting of 1 to 3 carbon atoms. The $C_{1-3}$ alkyl includes $C_{1-2}$, $C_{2-3}$ alkyl, and the like, and may be monovalent (e.g., methyl), divalent (e.g., methylene), or polyvalent (e.g., methenyl). Examples of $C_{1-3}$ alkyl include, but are not limited to, methyl (Me), ethyl (Et), propyl (including n-propyl and isopropyl), and the like.

Unless otherwise specified, the term "$C_{1-3}$ alkylamino" refers to —NH—$C_{1-3}$ alkyl.

Unless otherwise specified, "$C_{3-6}$ cycloalkyl" refers to a saturated cyclic hydrocarbon group consisting of 3 to 6 carbon atoms, including monocyclic and bicyclic ring systems. The $C_{3-6}$ cycloalkyl includes $C_{3-5}$ cycloalkyl, $C_{4-5}$ cycloalkyl, $C_{5-6}$ cycloalkyl, and the like, and may be monovalent, divalent, or polyvalent. Examples of $C_{3-6}$ cycloalkyl include, but are not limited to, cyclopropyl, cyclobutyl, cyclopentyl, cyclohexyl, and the like.

Unless otherwise specified, the term "halo" or "halogen", by itself or as part of another substituent, refers to a fluorine, chlorine, bromine, or iodine atom.

The compounds disclosed herein can be prepared using a variety of synthetic methods well known to those skilled in the art, including the specific embodiments listed below, embodiments formed by combinations thereof with other chemical synthetic methods, and equivalents thereof known to those skilled in the art. The preferred embodiments include, but are not limited to, the examples of the present application.

The compound disclosed herein may be structurally confirmed by conventional methods well known to those skilled in the art, if the present application relates to the absolute configuration of the compound, this absolute configuration may be confirmed by means of conventional techniques in the art. For example, in single crystal X-ray diffraction (SXRD), intensity data of diffraction of the single crystal grown are collected with a Bruker D8 venture diffractometer, with the light source being Cu-Kα radiation and the scanning mode being φ/ω scanning; after related data are collected, a direct method (Shelxs97) is further employed to analyze the crystal structure, and thus the absolute configuration can be confirmed.

The solvents used herein are commercially available. The following abbreviations are used in the present application: ACN represents acetonitrile; EtOAc represents ethyl acetate; EtOH represents ethanol; MeOH represents methanol; HPLC represents high performance liquid chromatography; LCMS represents liquid chromatography-mass spectrometry; ° C. represents Celsius degree; h represents hour; mL represents milliliter; mM represents millimoles per liter; mmol represents millimole; μmol represents micromole; HNMR represents nuclear magnetic hydrogen spectroscopy; MS represents mass spectrometry; min represents minute; pH represents the negative logarithm of the molar concentration of hydrogen ions; $AlMe_3$ represents trimethylaluminum; TFA represents trifluoroacetic acid; and DMSO represents dimethyl sulfoxide.

The term "treat" or "treatment" means administering a compound or formulation described herein to ameliorate or eliminate a disease or one or more symptoms associated with the disease, including:

(i) inhibiting a disease or disease state, i.e., arresting its progression; and (ii) alleviating a disease or disease state, i.e., causing its regression.

The term "prevent" or "prevention" means administering a compound or formulation described herein to prevent a disease or one or more symptoms associated with the disease, including preventing the occurrence of the disease or disease state in a mammal, particularly when such a mammal is predisposed to the disease state but has not yet been diagnosed with it.

The term "therapeutically effective amount" refers to an amount of the compound disclosed herein for (i) treating or preventing a specific disease, condition, or disorder, (ii) alleviating, ameliorating, or eliminating one or more symptoms of a specific disease, condition, or disorder, or (iii) preventing or delaying onset of one or more symptoms of a specific disease, condition, or disorder described herein. The amount of the compound disclosed herein composing the "therapeutically effective amount" varies depending on the compound, the disease state and its severity, the administration regimen, and the age of the mammal to be treated, but can be determined routinely by those skilled in the art in accordance with their knowledge and the present disclosure.

DETAILED DESCRIPTION

The present application is described in detail below by way of examples. However, this is by no means disadvantageously limiting the scope of the present application. Although the present application has been described in detail herein and specific examples have also been disclosed, it will be apparent to those skilled in the art that various changes and modifications can be made to the specific examples without departing from the spirit and scope of the present application. All reagents used in the present application are commercially available and can be used without further purification.

Examples 1 and 2

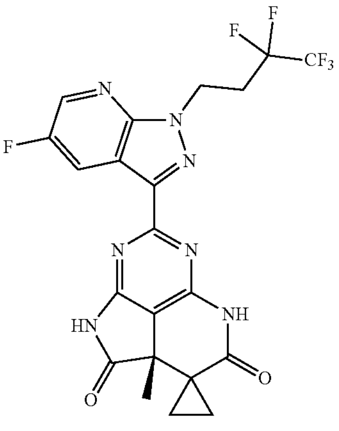

001 or 002

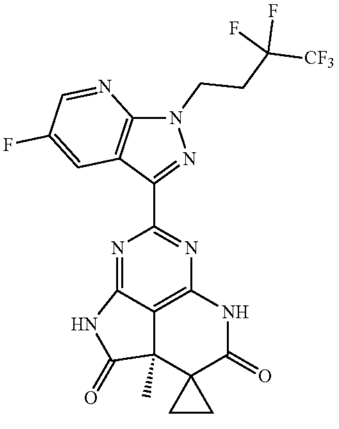

002 or 001

Synthetic Route:

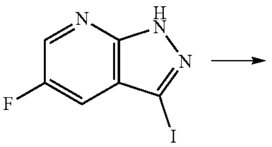

001_1

-continued
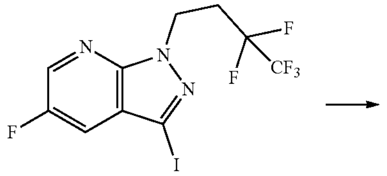
001_2
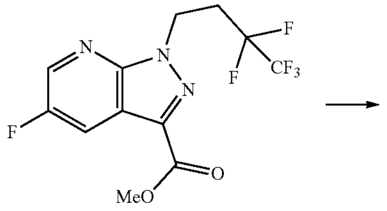
001_3
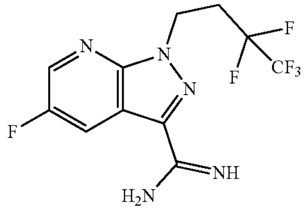
001_4
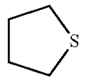
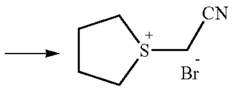
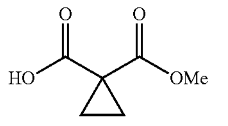
001_7
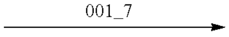
001_5
001_6
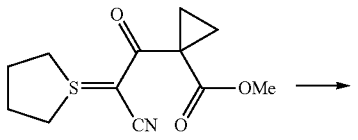
001_8
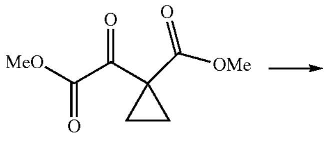
001_9
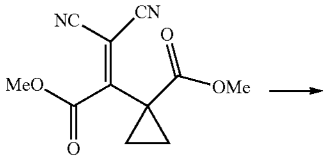
001_10
-continued
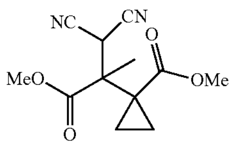
001_11
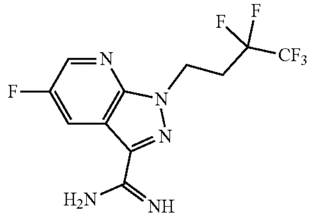
001_4
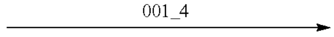
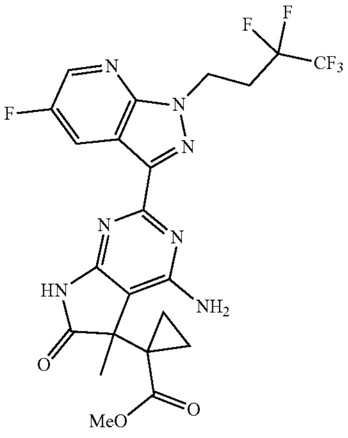
001_12
+
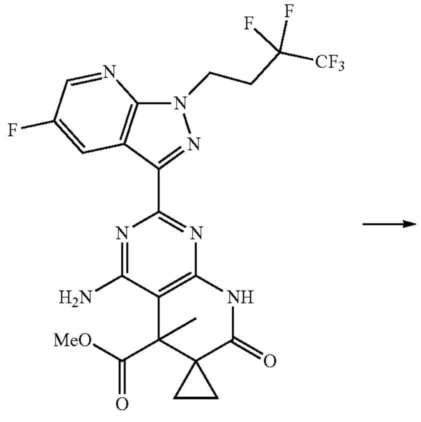
001_13
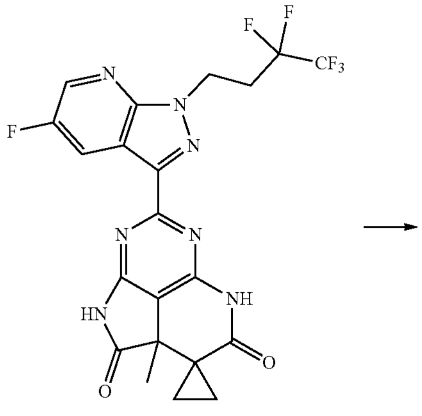
001_14

-continued

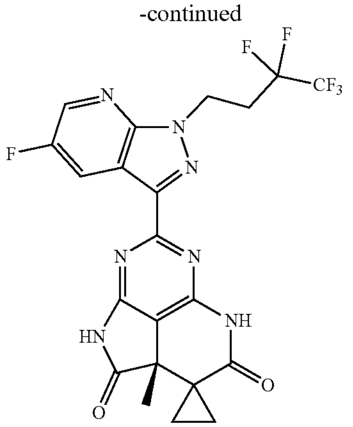

\+

001 or 002

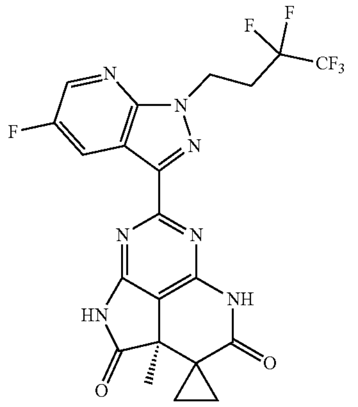

002 or 001

Step 1: Synthesis of Compound 001_2

Compound 001_1 (100 g, 380.21 mmol) was added to N,N-dimethylformamide (1 L) at room temperature, and then 1,1,1,2,2-pentafluoro-4-iodobutane (520.83 g, 1.90 mol) and potassium carbonate (131.37 g, 950.53 mmol) were added. The reaction system was stirred at 80° C. for 2 h. After the reaction was completed, the reaction solution was cooled to room temperature and then filtered, and the filtrate was concentrated under reduced pressure. The residue was separated by a chromatographic column (eluent: petroleum ether/ethyl acetate=1/0 to 15/1, v/v) to give compound 001_2.

Step 2: Synthesis of Compound 001_3

Compound 001_2 (30 g, 73.34 mmol) was added to methanol (100 mL) and N,N-dimethylformamide (300 mL) at room temperature under nitrogen atmosphere, and then cyclopenta-2,4-dien-1-yl(diphenyl)phosphino ferrocene dichloropalladium dichloromethane (3.76 g, 5.13 mmol) and triethylamine (29.68 g, 293.35 mmol, 40.83 mL) were added. The reaction mixture was stirred under nitric oxide atmosphere (15 Psi) at 80° C. for 12 h. After the reaction was completed, the reaction solution was cooled to room temperature and concentrated under reduced pressure. The residue was separated by a chromatographic column (eluent: petroleum ether/ethyl acetate=1/0 to 10/1, v/v) to give compound 001_3.

Step 3: Synthesis of Hydrochloride of Compound 001_4

Ammonium chloride (28.22 g, 527.54 mmol) was dispersed in toluene (360 mL) at room temperature under nitrogen atmosphere, and a solution of trimethylaluminum in toluene (2 M, 253.22 mL) was added. The mixture was heated to 80° C., and then compound 001_3 (36 g, 105.51 mmol) was added. The mixture was stirred at 80° C. for 30 min, warmed to 110° C., and then reacted for 1.5 h. After the mixture was cooled to 25° C., methanol (48.68 g, 1.52 mol, 61.48 mL) was added dropwise with the temperature maintained not higher than 40° C. Then, hydrochloric acid (3 M, 675.25 mL) was added with the temperature maintained not higher than 40° C. The mixture was warmed to 80° C. and stirred for 10 min, and then cooled to 0° C. and stirred for 30 min. After the reaction was completed, the reaction solution was filtered. The filter cake was collected, rinsed with water (200 mL), and then concentrated under reduced pressure to remove the solvent, thus giving the hydrochloride of compound 001_4. $^1H$ NMR (400 MHz, DMSO-$d_6$) δ ppm 9.49 (br d, J=11.2 Hz, 4H) 8.87 (s, 1H) 8.53 (dd, J=8.8, 2.4 Hz, 1H) 4.94 (t, J=6.8 Hz, 2H) 2.97-3.18 (m, 2H).

Step 4: Synthesis of Compound 001_6

Compound 001_5 (5 g, 56.71 mmol) was dissolved in dry toluene (20 mL) at room temperature under nitrogen atmosphere, and bromoacetonitrile (7.48 g, 62.38 mmol) was added. The reaction system was stirred at 25° C. for 12 h. A white solid was gradually precipitated from the clear reaction system. After the reaction was completed, the suspension was filtered. The filter cake was washed with toluene (50 mL), and the solid was collected and dried under reduced pressure to give compound 001_6.

Step 5: Synthesis of Compound 001_8

Compound 001_7 (2.7 g, 18.73 mmol) was dissolved in dichloromethane (50 mL) at room temperature. After the mixture was cooled to 0° C. N,N-diisopropylethylamine (7.26 g, 56.20 mmol), a 50% solution of propylphosphonic anhydride in ethyl acetate (17.88 g, 28.10 mmol), and compound 001_6 (4.29 g, 20.61 mmol) were added. The reaction system was stirred at 25° C. for 12 h. After the reaction was completed, the reaction solution was poured into a saturated aqueous sodium bicarbonate solution (100 mL) and extracted with ethyl acetate (50 mL×3). The organic phase was washed with saturated brine (20 mL), dried over anhydrous sodium sulfate, and then filtered and concentrated. The residue was separated and purified by column chromatography (eluent: petroleum ether/ethyl acetate=1/1 to 0/1, v/v) to give compound 001_8.

Step 6: Synthesis of Compound 001_9

Compound 001_8 (8.0 g, 31.58 mmol) was dissolved in methanol (500 mL) and water (50 mL) at room temperature under nitrogen atmosphere, and potassium monopersulfate (58.25 g, 94.74 mmol) was added. The reaction system was stirred at 25° C. for 12 h. After the reaction was completed, the reaction solution was poured into a saturated aqueous sodium sulfite solution (50 mL) and extracted with ethyl acetate (20 mL×3). The organic phase was washed with saturated brine (20 mL), dried over anhydrous sodium sulfate, and then filtered and concentrated. The residue was separated and purified by column chromatography (eluent: petroleum ether/ethyl acetate=1/0 to 4/1, v/v) to give compound 001_9.

Step 7: Synthesis of Compound 001_10

Compound 001_9 (5 g, 26.86 mmol) was dissolved in anhydrous methanol (50 mL) at room temperature under nitrogen atmosphere, and malononitrile (2.13 g, 32.23 mmol) and ammonium acetate (4.14 g, 53.72 mmol) were added thereto. The reaction system was warmed to 60° C. and stirred for 4 h under nitrogen atmosphere. The reaction solution was poured into a saturated aqueous ammonium chloride solution (70 mL) and extracted with ethyl acetate (20 mL×3). The organic phase was washed with saturated brine (20 mL), dried over anhydrous sodium sulfate, and then filtered and concentrated. The residue was separated and purified by column chromatography (eluent: petroleum ether/ethyl acetate=1/0 to 5/1, v/v) to give compound 001_10.

Step 8: Synthesis of Compound 001_11

Compound 001_10 (1.1 g, 4.70 mmol) was dissolved in tetrahydrofuran (10 mL) under nitrogen atmosphere. The mixture was cooled to 0° C. and a solution of methyl magnesium bromide in toluene (3 M, 3.13 mL) was added dropwise. After the addition was completed, the mixture was stirred for 15 min. After the reaction was completed, the reaction solution was poured into a saturated aqueous ammonium chloride solution (50 mL) and extracted with ethyl acetate (20 mL×3). The organic phase was washed with saturated brine (20 mL), dried over anhydrous sodium sulfate, and then filtered and concentrated. The residue was separated by column chromatography (eluent: petroleum ether/ethyl acetate=1/0 to 5/1, v/v) to give compound 001_11.

Step 9: Synthesis of Compounds 001_12 and 001_13

Compound 001_4 (1 g, 2.76 mmol, hydrochloride) was dissolved in tert-butanol (20 mL) at room temperature under nitrogen atmosphere, and compound 001_11 (1 g, 4.00 mmol) and potassium bicarbonate (692.06 g, 6.91 mmol) were added thereto. The reaction system was warmed to 85° C. and stirred for 12 h. After the reaction was completed, the reaction solution was cooled to room temperature, poured into water (70 mL), and extracted with ethyl acetate (50 mL×3). The organic phase was washed with saturated brine (50 mL), dried over anhydrous sodium sulfate, and then filtered and concentrated. The residue was separated and purified by column chromatography (eluent: petroleum ether/ethyl acetate=1/0 to 1/1, v/v) to give a mixture of 001_12 and 001_13.

Step 10: Synthesis of Compound 001_14

The mixture of 001_12 and 001_13 (500 mg, 920.10 μmol) was dissolved in toluene (5 mL) at room temperature under nitrogen atmosphere. The reaction system was added with a solution of trimethylaluminum in toluene (2 M, 1.38 mL), warmed to 75° C., and stirred for 5 h. After the reaction was completed, the reaction system was cooled to room temperature and added with diluted hydrochloric acid (1 N, 10 mL) to quench the reaction. The reaction system was diluted with ethyl acetate (20 mL), and liquid separation was performed. The organic phase was collected, and the aqueous phase was extracted with ethyl acetate (20 mL×3). The organic phases were combined, dried over anhydrous sodium sulfate, and filtered, and the filtrate was concentrated under reduced pressure to remove the solvent. The residue was separated by column chromatography (eluent: petroleum ether/ethyl acetate=1/0 to 1/1, v/v) and then by prep-HPLC (column: Phenomenex luna C18 (80 mm×30 mm I.D., 3 μm); mobile phase: A: ACN, B: [$H_2O$ (containing 0.04% HCl)], gradient: B %: 30%-70%, 8 min) to give compound 001_14. MS-ESI m/z: 512.0 $[M+H]^+$. $^1H$ NMR (400 MHz, $DMSO\_d_6$) δ: 11.52 (s, 1H)), 11.29 (s, 1H), 8.81-8.68 (m, 2H), 4.91 (t, J=6.7 Hz, 2H), 3.00 (tt, J=6.6, 19.1 Hz, 2H), 1.60-1.48 (m, 1H), 1.44 (s, 3H), 1.18-1.08 (m, 1H), 0.81-0.64 (m, 2H).

Step 11: Synthesis of Compounds 001 and 002

Compound 001_14 was separated by a chiral column (column: DAICEL CHIRALPAK AS (250 mm×30 mm, 10 μm); mobile phase: [EtOH (containing 0.1% $NH_3H_2O$]%: 35%-35%, 7 min)) to give compounds 001 and 002. SFC analysis method: column. Chiralpak AD (50×4.6 mm I.D., 3 μm); mobile phase: A: $CO_2$, B: [EtOH (containing 0.1% IPAm)], gradient: B %: 5%-50%, 3 min.

001 (retention time: 0.900 min): MS-ESI m/z: 512.0 $[M+H]^+$. $^1H$ NMR (400 MHz, $DMSO\_d_6$) δ: 11.52 (s, 1H), 11.34-11.24 (m, 1H), 8.82-8.68 (m, 2H), 4.91 (t, J=6.5 Hz, 2H), 3.09-2.91 (m, 2H), 1.55 (ddd, J=4.4, 6.0, 10.0 Hz, 1H), 1.44 (s, 3H), 1.20-1.08 (m, 1H), 0.81-0.64 (m, 2H);

002 (retention time: 1.017 min): MS-ESI m/z: 511.9 $[M+H]^+$. $^1H$ NMR (400 MHz, $DMSO\_d_6$) δ: 11.61-11.46 (m, 1H), 11.28 (s, 1H), 8.78-8.70 (m, 2H), 4.91 (t, J=6.7 Hz, 2H), 3.10-2.88 (m, 2H), 1.55 (ddd, J=4.0, 6.4, 10.0 Hz, 1H), 1.44 (s, 3H), 1.19-1.04 (m, 1H), 0.82-0.66 (m, 2H).

Examples 3 and 4

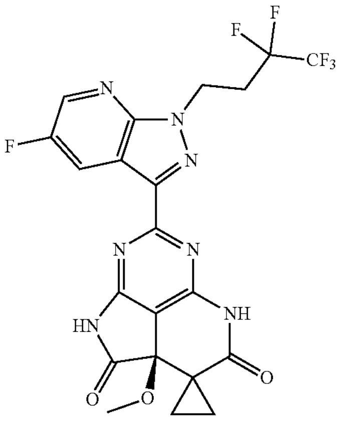

003 or 004

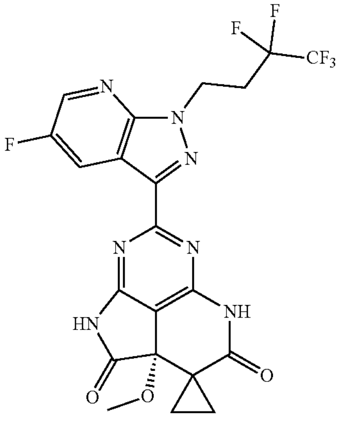

004 or 003

Synthetic Route:

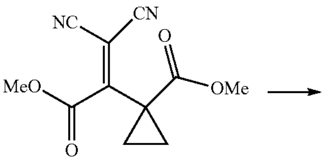

001_10

-continued

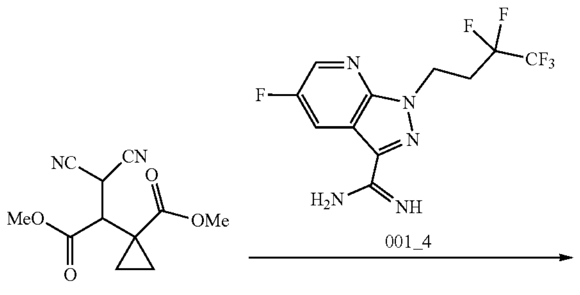

003_1

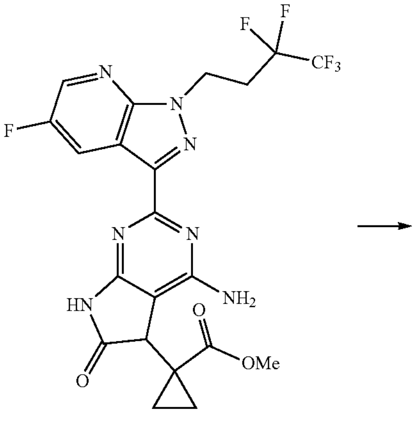

003_2

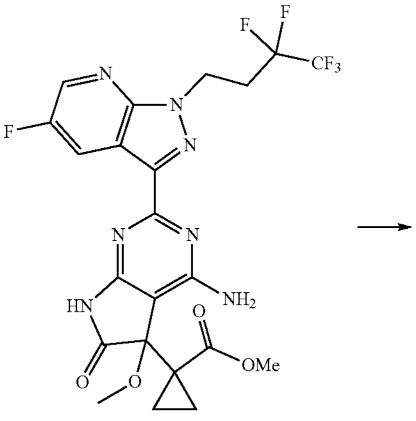

003_3

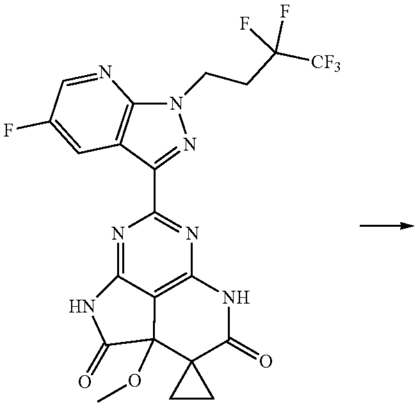

003_4

-continued

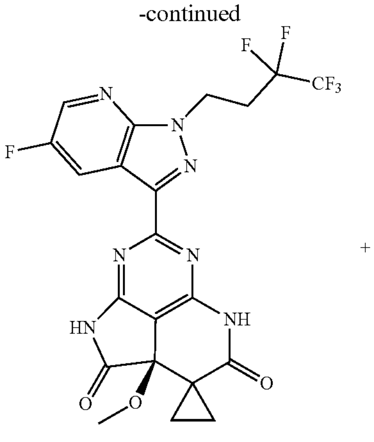

003 or 004

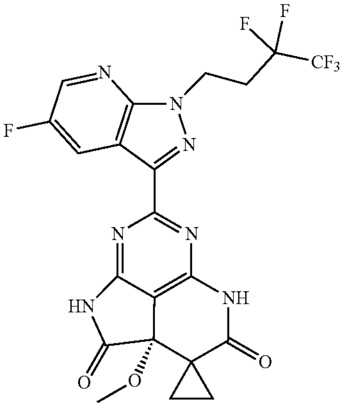

004 or 003

Step 1: Synthesis of Compound 003_1

Compound 001_10 (1.5 g, 6.40 mmol) was dissolved in chloroform (10 mL) and ethanol (10 mL) at room temperature under nitrogen atmosphere, and diethyl 2,6-dimethyl-1,4-dihydro-3,5-pyridinedicarboxylate (2.43 g, 9.61 mmol) was added to the reaction system. The reaction solution was stirred at 25° C. for 12 h under nitrogen atmosphere. After the reaction was completed, the reaction solution was poured into water (100 mL) and extracted with ethyl acetate (50 mL×3). The combined organic phase was washed with saturated brine (50 mL), dried over anhydrous sodium sulfate, and then filtered and concentrated. The resulting residue was separated and purified by column chromatography (eluent: petroleum ether/ethyl acetate=1/0 to 1/1, v/v) to give compound 003_1.

Step 2: Synthesis of Compound 003_2

Compound 001_4 (1.5 g, 4.15 mmol, hydrochloride) was dissolved in tert-butanol (30 mL) at room temperature under nitrogen atmosphere, and compound 003_1 (2 g, 8.47 mmol) and potassium bicarbonate (1.04 g, 10.37 mmol) were added thereto. The reaction system was warmed to 85° C. and stirred for 12 h. The reaction solution was cooled to room temperature, then poured into water (70 mL), and extracted with 2-methyltetrahydrofuran (30 mL×3). The combined organic phase was washed with saturated brine (20 mL), dried over anhydrous sodium sulfate, and then filtered and concentrated. The resulting residue was separated and purified by column chromatography (eluent: petroleum ether/ethyl acetate=1/0 to 1/1, v/v) to give compound 003_2.

Step 3: Synthesis of Compound 003_3

Compound 003_2 (500 mg, 944.48 μmol) was dissolved in anhydrous methanol (10 mL) at room temperature under nitrogen atmosphere, and [bis(trifluoroacetoxy)iodo]benzene (2.03 g, 4.72 mmol) was added. The mixture was stirred at 50° C. for 6 h. The reaction solution was poured into a saturated aqueous sodium bicarbonate solution (50 mL) and extracted with ethyl acetate (30 mL×3). The organic phase was washed with saturated brine (20 mL), dried over anhydrous sodium sulfate, and then filtered and concentrated. The resulting residue was separated and purified by column chromatography (eluent: petroleum ether/ethyl acetate=1/0 to 1/1, v/v) to give compound 003_3.

Step 4: Synthesis of Compound 003_4

Compound 003_3 (150 mg, 268.13 μmol) was dissolved in anhydrous toluene (2 mL) at room temperature under nitrogen atmosphere. The reaction system was added with a solution of trimethylaluminum in toluene (2 M, 429.02 μL), warmed to 80° C., and stirred for 6 h. After the reaction was completed, the reaction system was cooled to room temperature and slowly added with diluted hydrochloric acid (1 N, 10 mL) to quench the reaction. The mixture was extracted with 2-methyltetrahydrofuran (50 mL×4). The organic phases were combined, washed with half-saturated brine (10 mL×2) and saturated brine (20 mL) in sequence, dried over anhydrous sodium sulfate, and then filtered and concentrated. The resulting residue was separated and purified by column chromatography (eluent: petroleum ether/2-methyltetrahydrofuran=1/0 to 1/1, v/v) and by prep-HPLC (column: Phenomenex luna C18 (80 mm×30 mm I.D., 3 μm); mobile phase: A: ACN, B: [$H_2O$ (containing 0.04% HCl)], gradient: B %: 30%-55%, 8 min) to give compound 003_4. MS-ESI m/z: 527.9 $[M+H]^+$. $^1H$ NMR (400 MHz, DMSO-$d_6$) δ: 11.77 (s, 1H), 11.48 (s, 1H), 8.85-8.65 (m, 2H), 4.93 (t, J=6.8 Hz, 2H), 3.19 (s, 3H), 3.10- 2.92 (m, 2H), 1.63 (ddd, J=4.2, 6.8, 9.6 Hz, 1H), 1.43-1.34 (m, 1H), 1.00-0.84 (m, 2H).

Step 5: Synthesis of Compounds 003 and 004

Compound 003_4 (40 mg, 75.85 μmol) was separated by a chiral column (column: DAICEL CHIRALPAK AS (250 mm×30 mm, 10 μm); mobile phase: A: $CO_2$, B: [Neu-IPA], gradient: B %: 25%-25%, 10 min) to give compounds 003 and 004.

SFC analysis method: column: Chiralcel OX-3 (50×4.6 mm I.D., 3 μm); mobile phase: A: $CO_2$, B: [0.1% IPAm IPA], gradient: B %: 5%-50%, 3 min.

003 (retention time: 0.997 min): MS-ESI m/z: 527.9 $[M+H]^+$. $^1H$ NMR (400 MHz, DMSO_$d_6$) δ: 11.77 (s, 1H), 11.47 (s, 1H), 8.82-8.70 (m, 2H), 4.93 (t, J=6.8 Hz, 2H), 3.19 (s, 3H), 3.02-2.95 (m, 2H), 1.66-1.59 (m, 1H), 1.42-1.35 (m, 1H), 1.00-0.84 (m, 2H);

004 (retention time: 1.075 min): MS-ESI m/z: 528.2 $[M+H]^+$. $^1H$ NMR (400 MHz, DMSO_$d_6$) δ: 11.88-11.70 (m, 1H), 11.46 (br s, 1H), 8.83-8.69 (m, 2H), 4.93 (t, J=6.8 Hz, 2H), 3.19 (s, 3H), 3.10-2.92 (m, 2H), 1.68-1.58 (m, 1H), 1.43-1.34 (m, 1H), 0.99-0.84 (m, 2H).

Example 5

005

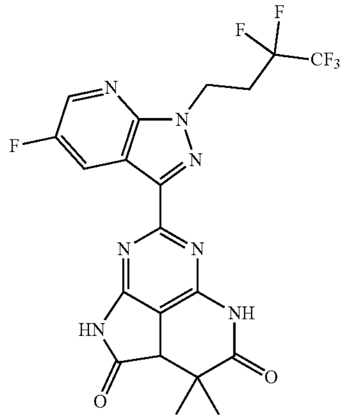

Synthetic Route:

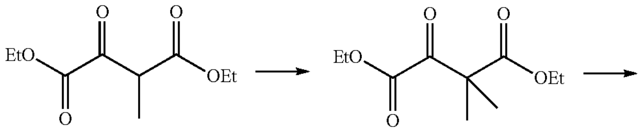

005_1 005_2

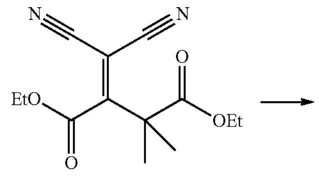

005_3

-continued

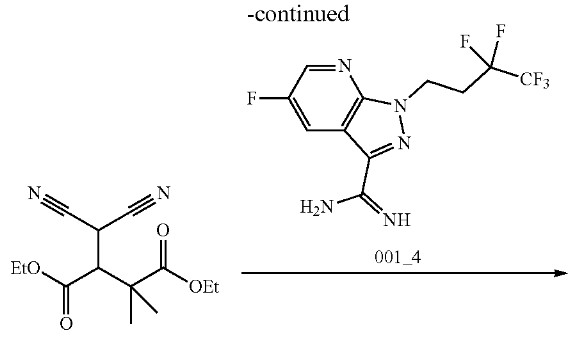

001_4

005_4

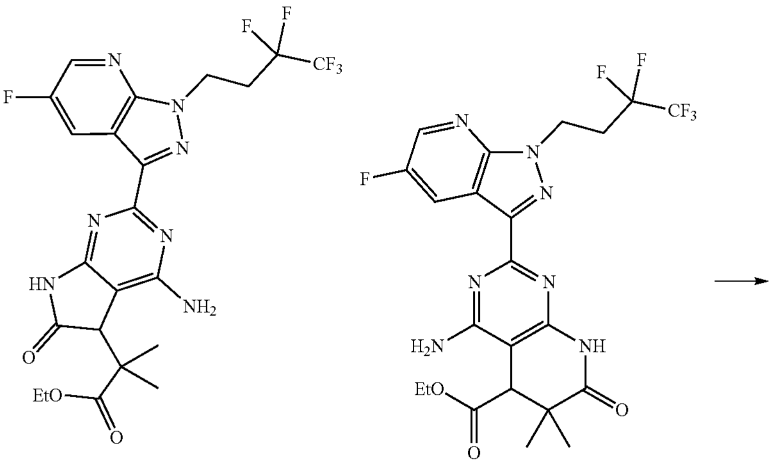

005_5

005_6

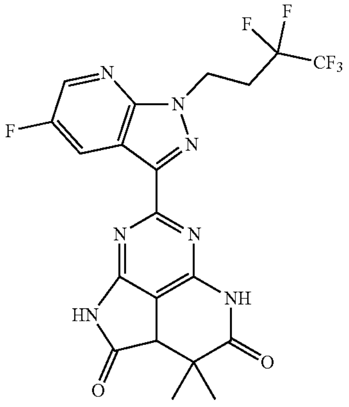

005

Step 1: Synthesis of Compound 005_2

A solution of potassium tert-butoxide in tetrahydrofuran (1 M, 276.95 mL) was added to toluene (2 L) at room temperature. Then, compound 005_1 (50 g, 247.28 mmol, 45.87 mL) was added, and finally iodomethane (228.14 g, 1.61 mol, 100.06 mL) and 18-crown-6 (6.54 g, 24.73 mmol) were added. After the addition, the reaction solution was stirred at 25° C. for 12 h. The reaction solution was added with 500 mL of 25% ammonium hydroxide to quench the reaction, 1 L of water was added, and the mixture was extracted with ethyl acetate (1 L×2). The organic phases were combined, dried over anhydrous sodium sulfate, and then filtered and concentrated under reduced pressure. The residue was separated and purified by a chromatographic column (eluent: petroleum ether/2-methyltetrahydrofuran=1/0 to 1/1, v/v) to give compound 005_2.

MS-ESI m/z: 216.9 $[M+H]^+$.

Step 2: Synthesis of Compound 005_3

Compound 005_2 (20 g, 92.49 mmol) and malononitrile (24.44 g, 369.98 mmol) were added to ethanol (200 mL) at room temperature, and then pyridine (36.58 g, 462.47 mmol, 37.33 mL) was added. The reaction solution was stirred at 70° C. for 12 h. The reaction solution was concentrated under reduced pressure and then dissolved in ethyl acetate (200 mL). The pH was adjusted to 5-6 with 3 M aqueous hydrochloric acid solution, and liquid separation was performed. The aqueous phase was extracted with ethyl acetate (100 mL×2). The organic phases were combined, dried over anhydrous sodium sulfate, and then filtered and concentrated under reduced pressure to give a residue. The residue was separated by a chromatographic column (eluent: petroleum ether/ethyl acetate=1/0 to 6/1, v/v) to give compound 005_3. $^1$H NMR (400 MHz, $CDCl_3$) δ: 4.42 (q, J=7.2 Hz, 2H), 4.25 (q, J=7.2 Hz, 2H), 1.61-1.66 (m, 6H), 1.39-1.47 (m, 6H).

Step 3: Synthesis of Compound 005_4

Compound 005_3 (3.2 g, 12.11 mmol) was added to chloroform (16 mL) and ethanol (16 mL) at room temperature, and then diethyl 2,6-dimethyl-1,4-dihydro-3,5-pyridinedicarboxylate (4.60 g, 18.16 mmol) was added. The reaction solution was stirred at 50° C. for 12 h. The reaction solution was poured into water (30 mL) and extracted with dichloromethane (30 mL×3). The organic phases were combined, dried over anhydrous sodium sulfate, and then filtered and concentrated under reduced pressure to give a residue. The residue was separated and purified by a chromatographic column (eluent: petroleum ether/ethyl acetate=1/0 to 95/5, v/v) to give compound 005_4. MS-NEG m/z: 265.2 $[M-H]^-$ Step 4: Synthesis of Compounds 005_5 and 005_6

Compounds 0014 (2.12 g, 5.87 mmol, hydrochloride) and 005_4 (2.50 g, 9.39 mmol) were added to tert-butanol (30 mL) at room temperature, and then potassium carbonate (2.03 g, 14.67 mmol) was added. The reaction mixture was stirred at 85° C. for 12 h. After the reaction was completed, the reaction solution was cooled to room temperature, then diluted with water (30 mL), and extracted with dimethyltetrahydrofuran (30 mL×3). The organic phases were combined, washed with saturated brine (50 mL), dried over anhydrous sodium sulfate, and then filtered and concentrated under reduced pressure to give a residue. To the residue was added 30 mL of methyl tert-butyl ether. The mixture was stirred at 20° C. for 1 h, whereupon a distinct solid was formed. The reaction solution was filtered and the filter cake was rinsed with methyl tert-butyl ether (10 mL) to give a mixture of 005_5 and 005_6. MS-ESI m/z: 546.1$[M+H]^+$.

Step 5: Synthesis of Compound 005

The mixture of 005_5 and 005_6 (2.36 g, 4.33 mmol) was added to toluene (25 mL) at room temperature under nitrogen atmosphere, and then a solution of trimethylaluminum in toluene (2 M, 6.92 mL) was added. The mixture was warmed to 80° C. and stirred for 12 h. The reaction solution was cooled to room temperature, the pH was adjusted to 5-6 using 3 M HCl diluted hydrochloric acid, and ethyl acetate (25 mL×3) was added for extraction. The organic phases were combined, dried over anhydrous sodium sulfate, and then filtered and concentrated under reduced pressure to give a residue. To the residue was added methyl tert-butyl ether (10 mL). The mixture was stirred at 25° C. for 1 h and then filtered and concentrated under reduced pressure to give compound 005. MS-ESI m/z: 500.2 $[M+H]^+$; $^1$H NMR (400 MHz, DMSO-$d_6$) δ: 11.50 (s, 1H), 11.10-11.19 (m, 1H), 8.75 (dd, J=2.58, 1.58 Hz, 1H), 8.72 (dd. J=8.7, 2.8 Hz, 1H), 4.90 (t, J=6.8 Hz, 2H), 4.0 (s, 1H), 2.89-3.09 (m, 2H), 1.48 (s, 3H), 0.79 (s, 3H).

Examples 6, 7, 8, and 9

006

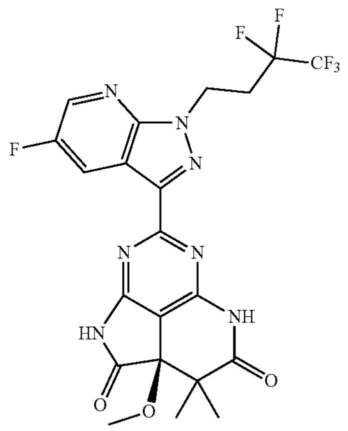

007

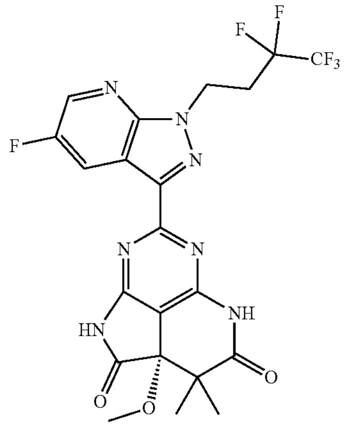

008 or 009

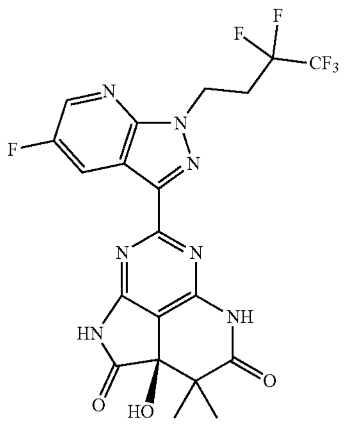

-continued
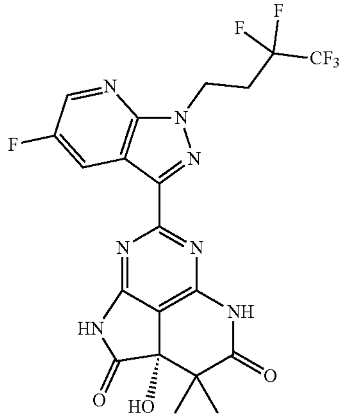
009 or 008
Synthetic Route:
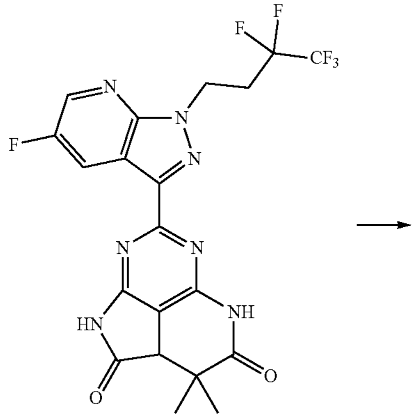
005
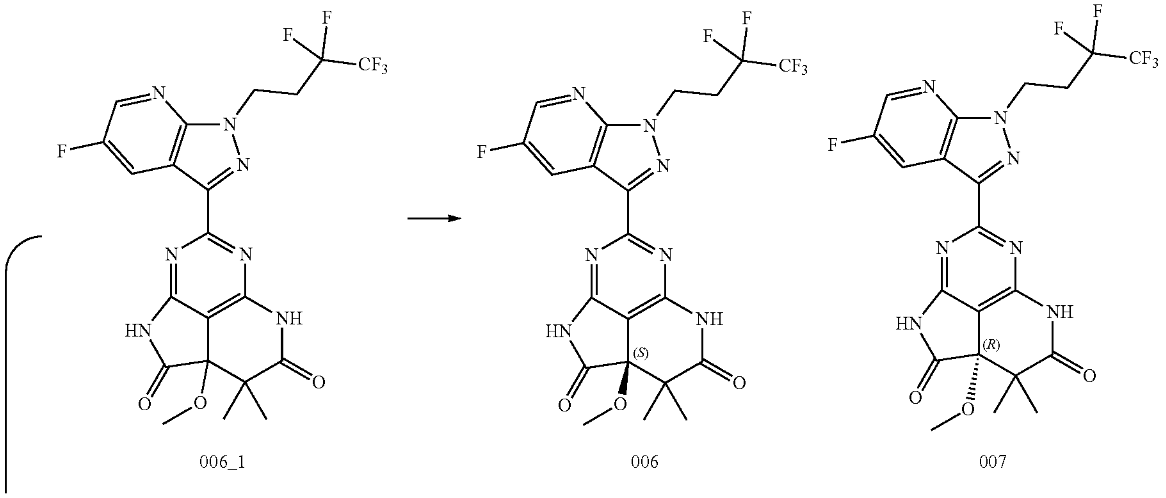
006_1 006 007

-continued

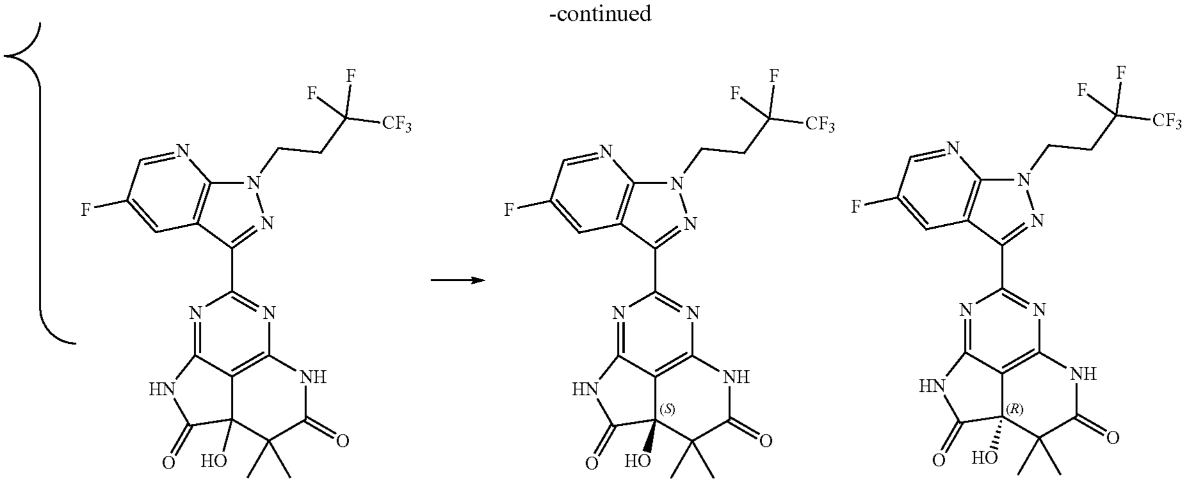

008_1 008 or 009 009 or 008

Step 1: Synthesis of Compounds 006_1 and 008_1

Compound 005 (660 mg, 1.32 mmol) was added to tetrahydrofuran (6 mL) and acetonitrile (3 mL) at room temperature under nitrogen atmosphere, and then methanol (169.39 mg, 5.29 mmol), potassium monopersulfate (1.63 g, 2.64 mmol), potassium dihydrogen phosphate (359.73 mg, 2.64 mmol), and cuprous bromide (37.92 mg, 264.33 μmol) were added. The reaction solution was stirred at 80° C. for 2 h. After the reaction was completed, the reaction solution was added with water (10 mL) and extracted with ethyl acetate (10 mL×2). The organic phases were combined, dried over anhydrous sodium sulfate, and then filtered and concentrated under reduced pressure to give a residue. The residue was separated by prep-HPLC (column: Phenomenex luna C18 (80 mm×30 mm I.D., 3 μm); mobile phase: A: ACN, B: [$H_2O$ (containing 0.04% HCl)], gradient: B %: 25%-50%, 8 min) to give compounds 006_1 and 008_1.

Compound 006_1: MS-ESI m/z: 530.0 $[M+H]^+$ $^1H$ NMR (400 MHz, DMSO-$d_6$) δ: 11.85 (s, 1H), 11.33, (s, 1H) 8.77 (dd, J=2.8, 1.6 Hz, 1H), 8.71 (dd, J=8.4, 2.8 Hz, 1H), 4.92 (t, J=6.8 Hz, 2H), 3.15 (s, 3H), 3.00 (tt, J=19.2, 6.8 Hz, 2H), 1.35 (s, 3H) 0.79 (s, 3H);

Compound 008_1: MS-ESI m/z: 516.2 $[M+H]^+$. $^1H$ NMR (400 MHz, DMSO-$d_6$) δ: 11.49 (s, 1H), 11.19 (s, 1H), 8.76 (dd, J=2.8, 1.6 Hz, 1H), 8.70 (dd, J=8.8, 2.8 Hz, 1H), 6.63 (br s, 1H), 4.86-4.98 (m, 2H), 3.00 (tt, J=19.2, 6.4 Hz, 2H), 1.38 (s, 3H), 0.77 (s, 3H).

Step 2: Synthesis of Compounds 006 and 007

Compound 006_1 (40 mg, 75.85 μmol) was separated by a chiral column (column: REGIS(S,S)WHELK-O1 (250 mm×25 mm, 10 μm); mobile phase: A: $CO_2$, B: [IPA (containing 0.1% $NH_3H_2O$)], gradient: B %: 25%-25%, 7 min) to give compounds 006 and 007.

SFC analysis method: column: Chiralcel (S,S)-Whelk-O1 (100×4.6 mm, I.D., 3.5 μm); mobile phase: [IPA (containing 0.1% IPAm)]%: 10%-50%, 3 min.

006 (retention time: 1.518 min): MS-ESI m/z: 530.2 $[M+H]^+$. $^1H$ NMR (400 MHz, DMSO-$d_6$) δ: 11.33 (br s, 1H) 11.70-12.03 (m, 1H) 8.77 (dd, J=2.4, 1.6 Hz, 1H) 8.71 (dd. J=8.8, 2.8 Hz, 1H), 4.93 (t, J=6.72 Hz, 2H), 3.16 (s, 3H), 3.00 (tt, J=19.2, 7.2 Hz, 2H), 1.35 (s, 3H), 0.79 (s, 3H);

007 (retention time: 1.644 min): MS-ESI m/z: 530.2 $[M+H]^+$ $^1H$ NMR (400 MHz, DMSO-$d_6$) δ: 8.76-8.79 (m, 1H) 8.70 (br d, J=8.8 Hz, 1H), 4.93 (t, J=6.8 Hz, 2H), 3.15 (s, 3H), 2.93-3.09 (m, 2H), 1.35 (s, 3H), 0.79 (s, 3H).

Step 3: Synthesis of Compounds 008 and 009

Compound 008_1 (70 mg, 135.83 μmol) was separated by a chiral column (column: Phenomenex-Cellulose-2 (250 mm×30 mm, 10 μm); mobile phase: A: $CO_2$, B: [MeOH (containing 0.1% $NH_3H_2O$)]; gradient: B %: 30%-30%, 10 min) to give compounds 008 and 009.

SFC analysis method: column: Chiralcel OD-3 (50 mm×4.6 mm I.D., 3 μm); mobile phase: A: $CO_2$, B: [MeOH (containing 0.1% IPAm)]; gradient: B %: 5%-50%, 3 min.

008 (retention time: 1.008 min): MS-ESI m/z: 516.2 $[M+H]^+$. $^1H$ NMR (400 MHz, DMSO-$d_6$) δ: 11.48 (s, 1H), 11.19 (s, 1H), 8.77 (dd, J=2.8, 1.6 Hz, 1H), 8.70 (dd, J=8.4, 2.8 Hz, 1H), 6.62 (s, 1H), 4.87-4.97 (m, 2H), 2.93-3.09 (m, 2H), 1.38 (s, 3H), 0.77 (s, 3H);

009 (retention time: 1.198 min): MS-ESI m/z: 516.2 $[M+H]^+$. $^1H$ NMR (400 MHz, DMSO-$d_6$) δ: 11.34-11.71 (m, 1H), 11.09-11.30 (m, 1H), 8.76 (s, 1H), 8.70 (dd. J=8.4, 2.8 Hz, 1H), 6.62 (s, 1H), 4.92 (br t, J=6.4 Hz, 2H), 2.92-3.12 (m, 2H), 1.38 (s, 3H), 0.77 (s, 3H).

Examples 10, 11, 12, and 13
010 or 011 or 012 or 013
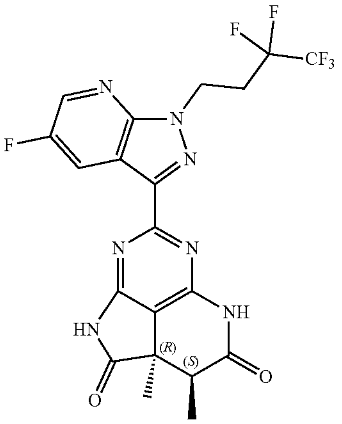
011 or 010 or 012 or 013
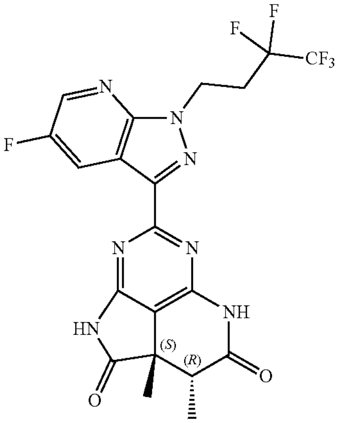
-continued
012 or 013 or 010 or 011
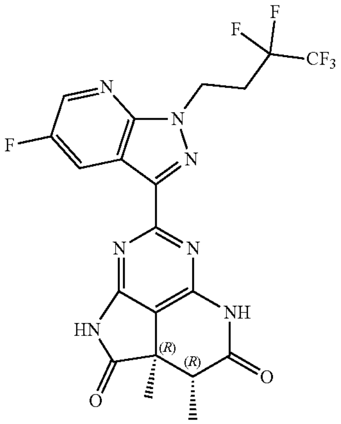
013 or 012 or 010 or 011
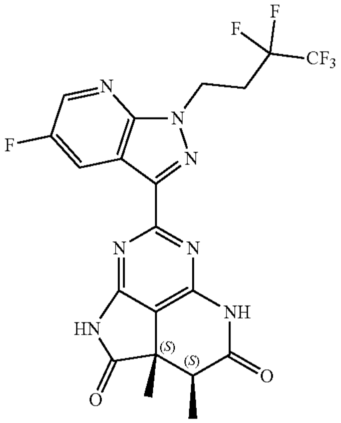
Synthetic Route:
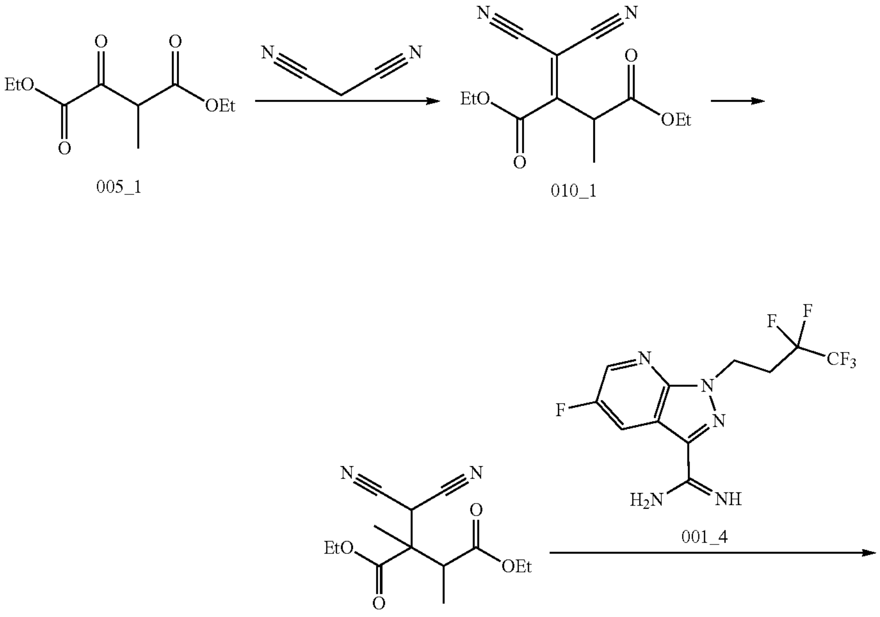
005_1
010_1
001_4
010_2

-continued

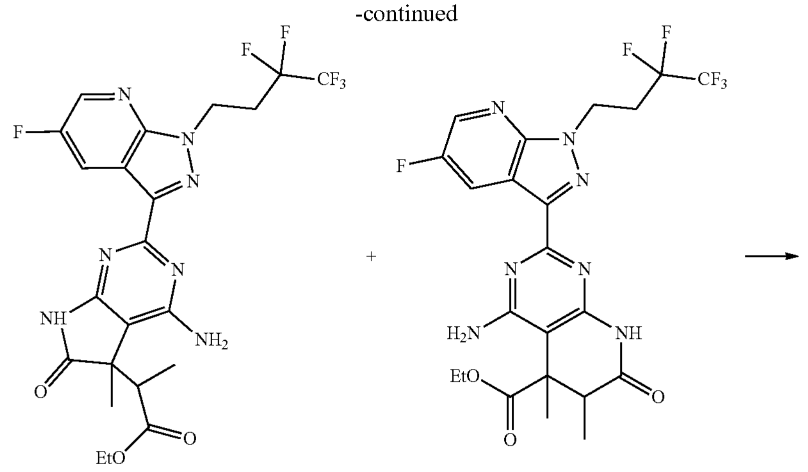

010_3 012_1

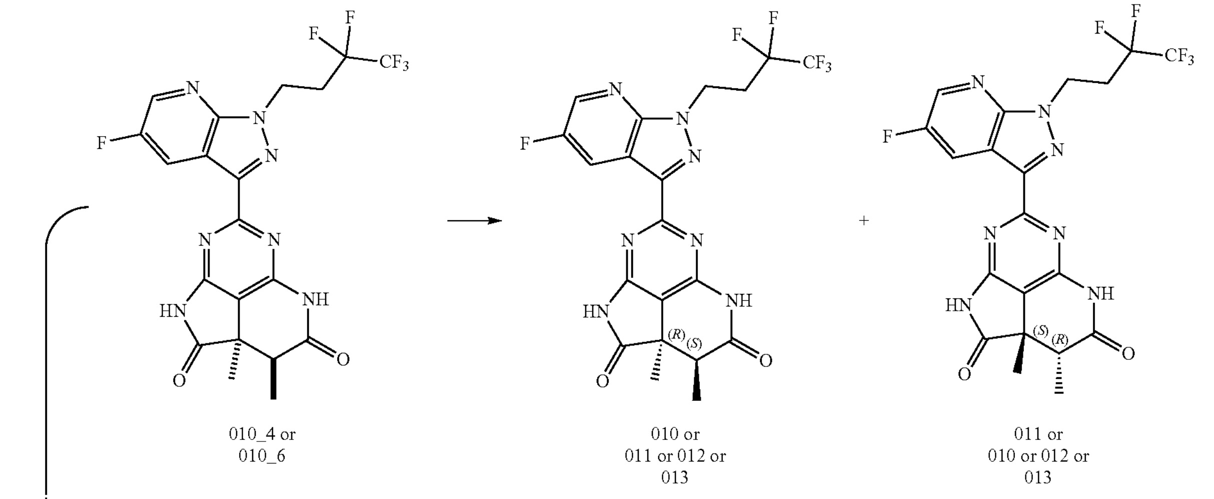

010_4 or 010_6

010 or 011 or 012 or 013

011 or 010 or 012 or 013

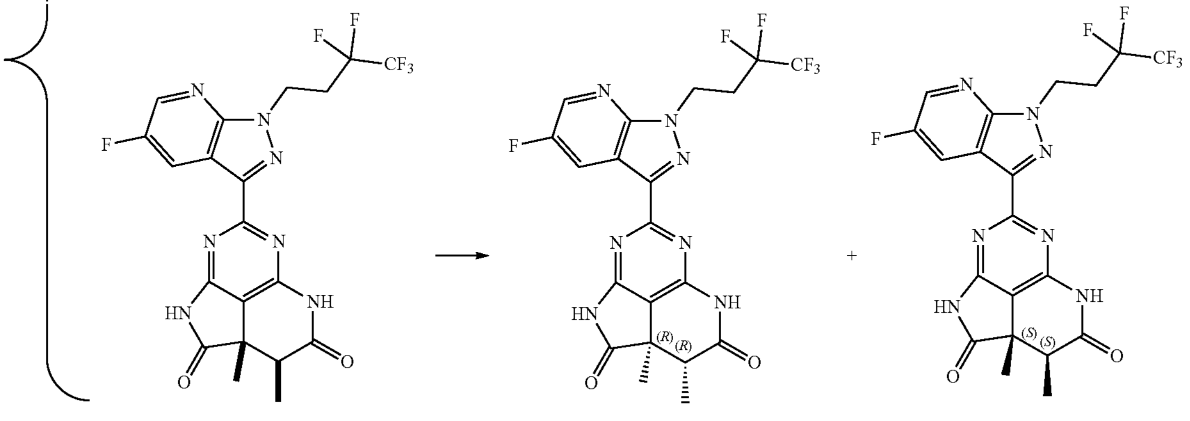

010_6 or 010_4

012 or 013 or 010 or 011

013 or 012 or 010 or 011

Step 1: Synthesis of Compound 010_1

Compound 005_1 (50 g, 247.28 mmol) was dissolved in toluene (500 mL) at room temperature, and malononitrile (16.34 g, 247.28 mmol), β-aminopropionic acid (660.92 mg, 7.42 mmol), and acetic acid (14.85 g, 247.28 mmol) were added thereto. The reaction system was warmed to 130° C. and stirred for 12 h. The reaction solution was poured into a saturated aqueous sodium bicarbonate solution (500 mL) and liquid separation was performed. The aqueous phase was extracted with ethyl acetate (100 mL×3). The organic phase was washed with saturated brine (100 mL), dried over anhydrous sodium sulfate, and then filtered and concentrated. The resulting residue was separated and purified by column chromatography (eluent: petroleum ether/ethyl acetate=1/0 to 5/1, v/v) to give compound 010_1.

Step 2: Synthesis of Compound 010_2

Compound 010_1 (7 g, 27.97 mmol) was dissolved in THF (15 mL), and the solution was purged three times with nitrogen. The reaction system was cooled to 0° C., and a solution of methyl magnesium bromide in ether (3 M, 13.99 mL) was slowly added dropwise. The reaction system was stirred at 0° C. for 15 min. The reaction system was poured into a saturated ammonium chloride solution (100 mL) and extracted with ethyl acetate (50 mL×3). The organic phases were combined, washed with half-saturated brine (10 mL×2) and then with saturated brine (20 mL), dried over anhydrous sodium sulfate, and then filtered and concentrated. The resulting residue was separated and purified by column chromatography (eluent: petroleum ether/ethyl acetate=1/0 to 5/1, v/v) to give compound 010_2.

Step 3: Synthesis of Mixture of Compounds 010_3 and 012_1

Compound 001_4 (3.5 g, 9.68 mmol, hydrochloride) was dissolved in tert-butanol (50 mL), and compound 010_2 (4.4 g, 16.52 mmol) and potassium bicarbonate (2.42 g, 24.19 mmol) were added thereto. The reaction system was warmed to 85° C. and stirred for 12 h. The reaction solution was poured into water (100 mL) and extracted with ethyl acetate (50 mL×3). The organic phase was washed with saturated brine (50 mL), dried over anhydrous sodium sulfate, and then filtered and concentrated. The resulting residue was separated and purified by column chromatography (eluent: petroleum ether/ethyl acetate=1/0 to 1/1, v/v) to give a mixture of compounds 010_3 and 012_1.

Step 4: Synthesis of Compounds 010_4 and 010_6

The mixture described above (800.00 mg, 1.47 mmol) was dissolved in toluene (10 mL), and the mixed solution was purged three times with nitrogen. The reaction system was added with a solution of trimethylaluminum in toluene (2 M, 2.20 mL), warmed to 75° C., and stirred for 5 h. After the reaction was completed, the reaction system was cooled to room temperature, and diluted hydrochloric acid (1 N, 10 mL) was added thereto to quench the reaction. The reaction solution was diluted with ethyl acetate (50 mL) and liquid separation was performed. The organic phase was collected, and the aqueous phase was extracted with ethyl acetate (50 mL×3). The organic phases were combined, dried over anhydrous sodium sulfate, and filtered, and the filtrate was concentrated under reduced pressure to remove the solvent, thus giving a crude product. The resulting residue was separated and purified by column chromatography (eluent: petroleum ether/ethyl acetate=1/0 to 2/1, v/v) and separated by prep-HPLC (column: Phenomenex luna C18 (250 mm×50 mm I.D., 10 μm), mobile phase: A: ACN, B: [$H_2O$ (containing 0.04% HCl)], gradient: B %: 30%-60%, 10 min) to give compounds 010_4 and 010_6.

LCMS analysis method: column: Luna 5 μm C18 (2×50 mm); mobile phase A: $H_2O$+0.05% (v/v) TFA; mobile phase B: ACN+0.05% (v/v) TFA, gradient: B %: 10%-100%, 6 min.

010_4 (retention time: 2.789 min) MS-ESI m/z: 500.1 $[M+H]^+$. $^1H$ NMR (400 MHz, DMSO-$d_6$) δ: 11.55 (s, 1H), 11.24 (s, 1H), 8.75 (dd. J=1.6, 2.8 Hz, 1H), 8.70 (dd, J=2.8, 8.4 Hz, 1H), 4.91 (t, J=6.8 Hz, 2H), 3.00 (tt, J=6.4, 19.2 Hz, 2H), 2.80 (q, J=7.2 Hz, 1H), 1.41 (s, 3H), 0.79 (d, J=7.2 Hz, 3H);

010_6 (retention time: 2.848 min) MS-ESI m/z: 500.0 $[M+H]^+$. $^1H$ NMR (400 MHz, DMSO-$d_6$) δ: 11.42 (s, 1H), 11.09 (s, 1H), 8.82-8.65 (m, 2H), 4.91 (t, J=6.6 Hz, 2H), 3.09-2.89 (m, 3H), 1.25 (t, J=3.4 Hz, 6H).

Step 5: Synthesis of Compounds 010 and 011

The compound 010_4 (retention time: 2.789 min) (720 mg, 1.27 mmol) was separated by a chiral column (column: DAICEL CHIRALPAK IE (250 mm×30 mm, 10 μm); mobile phase: A: $CO_2$, B: [EtOH (containing 0.1% $NH_3H_2O$)]; gradient: B %: 38%-38%, 6 min) to give compounds 010 and 011.

SFC analysis method: column: Chiralpak AD-3 (50 mm×4.6 mm I.D., 3 μm); mobile phase: A: $CO_2$, B: [EtOH (containing 0.1% IPAm)]; gradient: B: 5%-50%, 3 min.

Compound 010 (retention time: 1.00 min): MS-ESI m/z: 500.0 $[M+H]^+$. $^1H$ NMR (400 MHz, DMSO_$d_6$) δ: 11.41 (br s, 1H), 11.09 (br s, 1H), 8.82-8.59 (m, 2H), 4.90 (t, J=6.8 Hz, 2H), 3.13-2.87 (m, 3H), 1.25 (t, J=3.2 Hz, 6H);

Compound 011 (retention time: 1.311 min): MS-ESI m/z: 500.0 $[M+H]^+$. $^1H$ NMR (400 MHz, DMSO_$d_6$) δ: 11.42 (s, 1H), 11.09 (s, 1H), 8.75 (dd, J=1.6, 2.8 Hz, 1H), 8.71 (dd, J=2.8, 8.6 Hz, 1H), 4.91 (t, J=6.8 Hz, 2H), 3.13-2.91 (m, 3H), 1.31-1.19 (m, 6H).

Step 6: Synthesis of Compounds 012 and 013

Compound 010_6 (retention time: 2.848 min) (270 mg, 540.68 μmol) was separated by a chiral column (column: DAICEL CHIRALPAK IE (250 mm×30 mm, 10 μm); mobile phase: A: $CO_2$, B: [EtOH (containing 0.1% $NH_3H_2O$)]; gradient: B %: 33%-33%, 7 min) to give compounds 012 and 013.

SFC analysis method: column: Chiralpak IE-3 (50 mm×4.6 mm I.D., 3 μm); mobile phase: A: $CO_2$, B: [EtOH (containing 0.1% IPAm)], gradient: B %: 5%-50%, 3 min.

Compound 012 (retention time: 1.087 min): MS-ESI m/z: 499.9 $[M+H]^+$. $^1H$ NMR (400 MHz, DMSO_$d_6$) δ: 11.54 (br s, 1H), 11.23 (s, 1H), 8.75 (dd, J=1.6, 2.8 Hz, 1H), 8.70 (dd, J=2.8, 8.8 Hz, 1H), 4.91 (tt, J=6.8 Hz, 2H), 3.00 (t, J=6.4, 19.1 Hz, 2H), 2.85-2.76 (m, 1H), 1.41 (s, 3H), 0.80 (d, J=7.2 Hz, 3H);

Compound 013 (retention time: 1.193 min): MS-ESI m/z: 499.9 $[M+H]^+$. $^1H$ NMR (400 MHz, DMSO_$d_6$) δ: 11.53 (br s, 1H), 11.23 (br s, 1H), 8.78-8.66 ((m, 2H), 4.91 (t, J=6.8 Hz, 2H), 2.99 (tt, J=6.8, 19.2 Hz, 2H), 2.80 (q, J=7.2 Hz, 1H), 1.41 (s, 3H), 0.80 (d, J=7.2 Hz, 3H).

Examples 14 and 15

014 or 015

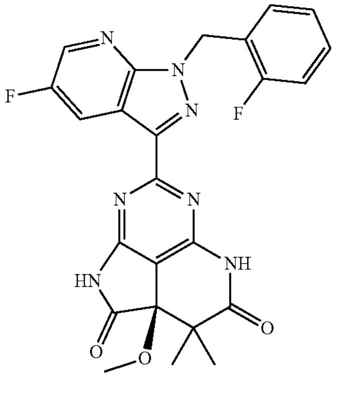

-continued
015 or 014
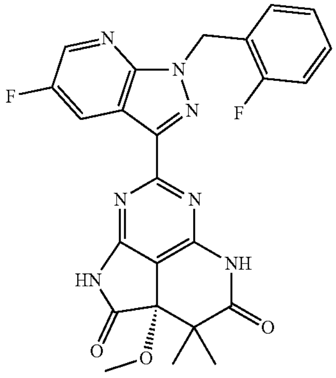
Synthetic Route:
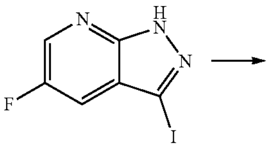
001_1
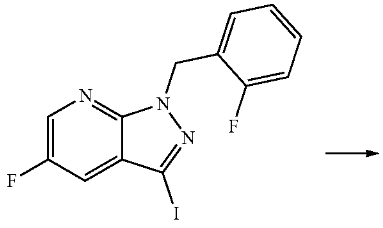
014_1
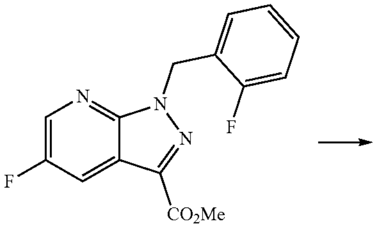
014_2
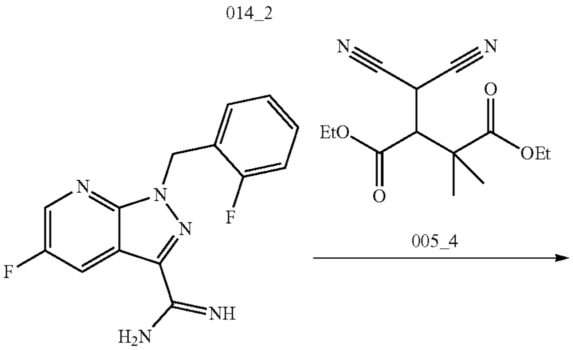
005_4
014_3
-continued
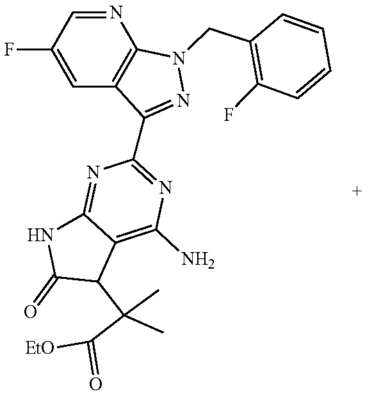
014_4
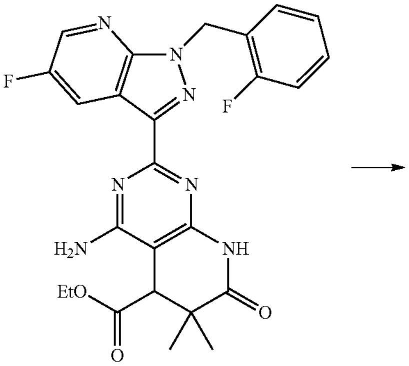
014_5
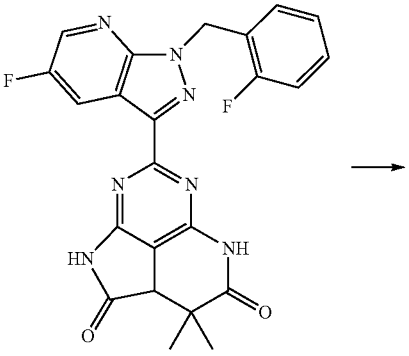
014_6
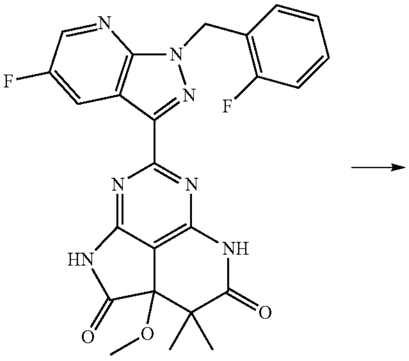
014_7

-continued

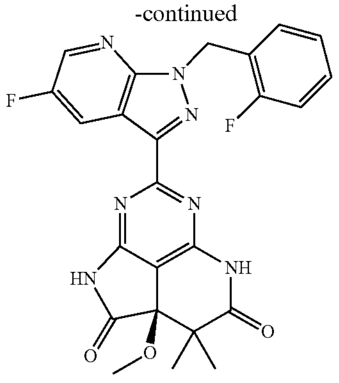

+

014 or 015

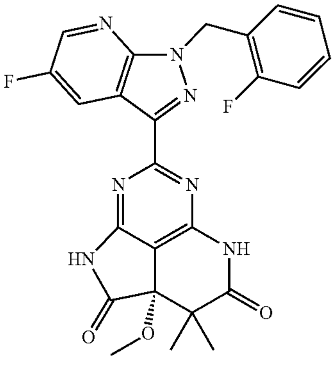

015 or 014

Step 1: Synthesis of Compound 014_1

Compound 001_1 (300 g, 1.14 mol) was added to N,N-dimethylformamide (3 L) at room temperature under nitrogen atmosphere, and then 2-fluorobenzyl chloride (164.91 g, 1.14 mol, 135.17 mL) and cesium carbonate (408.81 g, 1.25 mol) were added. The reaction solution was stirred at 80° C. for 2 h. After the reaction was completed, the reaction solution was cooled to room temperature and filtered to give a solution of compound 014_1 (423 g) in N,N-dimethylformamide (3 L), which could be used directly.

Step 2: Synthesis of Compound 014_2

Compound 014_1 (70 g, 188.62 mmol) was added to a N,N-dimethylformamide solution (1 L) at room temperature under nitrogen atmosphere, and methanol (300 mL), cyclopenta-2,4-dien-1yl(diphenyl)phosphino ferrocene dichloropalladium dichloromethane (6.90 g, 9.43 mmol), and triethylamine (76.34 g, 754.47 mmol, 105.01 mL) were added. The mixture was stirred at 80° C. for 12 h under carbon monoxide (15 psi) atmosphere. After the reaction was completed, the reaction solution was concentrated under reduced pressure to give a residue. The residue was separated and purified by column chromatography (eluent: petroleum ether/ethyl acetate=1/0 to 15/1, v/v) to give compound 014_2.

Step 3: Synthesis of Hydrochloride of Compound 014_3

Ammonium chloride (4.41 g, 82.44 mmol) was dispersed in toluene (50 mL) at room temperature under nitrogen atmosphere, and a solution of trimethylaluminum in toluene (2 M, 39.57 mL) was added. The mixture was heated to 80° C., and then compound 014_2 (5 g, 16.49 mmol) was added into the reaction system. The mixture was stirred at 80° C. for 30 min, warmed to 110° C., and then reacted for 1.5 h. After the mixture was cooled to 25° C., methanol (7.61 g, 237.42 mol) was added dropwise with the temperature maintained not higher than 40° C. Then, hydrochloric acid (3 M, 105.52 mL) was added with the temperature maintained not higher than 40° C. The mixture was warmed to 80° C. and stirred for 10 min, and then cooled to 0° C. and stirred for 30 min. After the reaction was completed, the reaction mixture was filtered. The filter cake was collected and rinsed with water (100 mL) to give the hydrochloride of compound 014_3.

Step 4: Synthesis of Compounds 014_4 and 014_5

Compound 005_4 (6.58 g, 24.71 mmol) was added to tert-butanol (70 mL) at room temperature under nitrogen atmosphere, and the hydrochloride of compound 014_3 (5 g, 15.45 mmol) and potassium carbonate (5.34 g, 38.61 mmol) were added in sequence. The reaction solution was stirred at 85° C. for 12 h. After the reaction was completed, the reaction solution was cooled to room temperature, added with water (100 mL), and extracted with dimethyltetrahydrofuran (100 mL×2). The organic phases were combined, washed with saturated brine (100 mL), dried over anhydrous sodium sulfate, and then filtered and concentrated under reduced pressure to give a mixture of compounds 014_4 and 014_5.

Step 5: Synthesis of Compound 014_6

The mixture of compounds 014_4 and 014_5 (7 g, 13.79 mmol) was dissolved in toluene (100 mL) at room temperature under nitrogen atmosphere, and a solution of trimethylaluminum in toluene (2 M, 28.97 mL) was slowly added dropwise. The mixture was stirred at 80° C. for 12 h. The reaction solution was cooled to room temperature and slowly poured into water (100 mL), 3 M hydrochloric acid was added, and the pH was adjusted to 5-6. The solution was extracted with dimethyltetrahydrofuran (100 mL×3). The organic phases were combined, dried over anhydrous sodium sulfate, and then filtered and concentrated under reduced pressure to give a residue. To the residue was added methyl tert-butyl ether (50 mL). The mixture was stirred at 25° C. for 1 h and filtered to give compound 014_6.

Step 5: Synthesis of Compound 014_7

Compound 014_6 (4.24 mg, 9.19 mmol) was dissolved in methanol (80 mL) at room temperature under nitrogen atmosphere, and [bis(trifluoroacetoxy)iodo]benzene (7.90 g, 18.38 mmol) was added. The mixture was stirred at 50° C. for 12 h. After the reaction was completed, the reaction solution was cooled to room temperature and filtered through diatomite to give a filtrate, and the filtrate was concentrated under reduced pressure to give a residue. The residue was separated by prep-HPLC (column: Welch Xtimate C18 (250 mm×70 mm I.D., 10 μm); mobile phase: A: ACN, B: [$H_2O$ (containing 0.04% HCl)], gradient: B %: 35%-70%, 20 min) to give compound 014_7. MS-ESI m/z: 492.0 $[M+H]^+$ $^1H$ NMR (400 MHz, DMSO-$d_6$) δ 11.81 (br s, 1H), 11.26-11.39 (m, 1H), 8.77 (d, J=1.00 Hz, 1H), 8.71 (dd, J=8.8, 2.8 Hz, 1H), 7.35-7.43 (m, 1H), 7.27-7.32 (m, 1H), 7.20-7.26 (m, 1H), 7.14-20 (m, 1H), 5.86 (s, 2H), 3.14 (s, 3H), 1.34 (s, 3H), 0.77 (s, 3H).

Step 6: Synthesis of Compounds 014 and 015

Compound 014_7 (200 mg, 406.96 μmol) was separated by a chiral column (column: REGIS (s,s) WHELK-O1 (250 mm×30 mm, 5 μm); mobile phase: [0.1% $NH_3H_2O$ MeOH] %: 32%-32% A, 16.5 min) to give compounds 014 and 015.

SFC analysis method: column: Chiralpak IE-3 (50 mm×4.6 mm I.D., 3 μm); mobile phase: A: $CO_2$, B: [EtOH (containing 0.1% IPAm)], gradient: B %: 5%-50%, 3 min.

014 (retention time: 2.612 min) MS-ESI m/z: 492.0 $[M+H]^+$ $^1H$ NMR (400 MHz, DMSO-$d_6$) δ 11.73-11.96 (m, 1H), 11.31 (s, 1H), 8.77 (dd, J=2.8, 1.6 Hz, 1H), 8.71 (dd, J=8.8, 2.8 Hz, 1H), 7.35-7.42 (m, 1H), 7.27-7.32 (m, 1H), 7.20-7.26 (m, 1H), 7.14-7.20 (m, 1H), 5.86 (s, 2H), 3.14 (s, 3H), 1.34 (s, 3H), 0.77 (s, 3H);

015 (retention time: 2.749 min) MS-ESI m/z: 492.0 $[M+H]^+$ $^1H$ NMR (400 MHz, DMSO-$d_6$) δ 11.75-11.89 (m, 1H), 11.28-11.36 (m, 1H), 8.77 (d, J=2.63 Hz, 1H), 8.71 (dd, J=8.66, 2.76 Hz, 1H), 7.35-7.42 (m, 1H), 7.27-7.32 (m, 1H), 7.20-7.26 (m, 1H), 7.14-7.20 (m, 1H), 5.86 (s, 2H), 3.14 (s, 3H), 1.34 (s, 3H), 0.77 (s, 3H).

Example 16

016

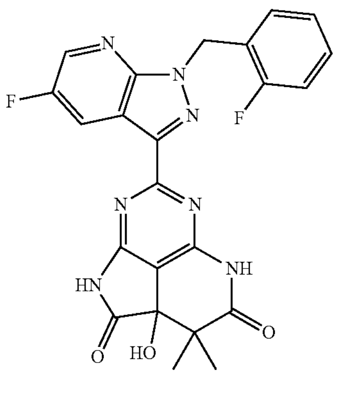

Synthetic Route:

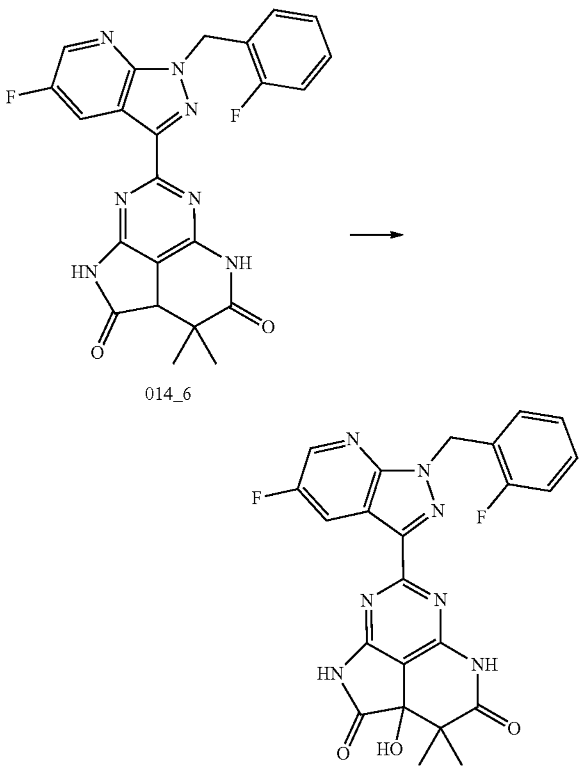

014_6

016

Step 1: Synthesis of Compound 016

Compound 014_6 (500 mg, 1.08 mmol) was dissolved in THF (5 mL) and $H_2O$ (5 mL) at room temperature under nitrogen atmosphere, and then potassium monopersulfate (1.33 g, 2.17 mmol), potassium dihydrogen phosphate (294.94 mg, 2.17 mmol), and cuprous bromide (31.09 mg, 216.72 μmol) were added. The reaction solution was stirred at 80° C. for 2 h. After the reaction was completed, the reaction solution was added with water (10 mL), and ethyl acetate (10 mL×2) was added for liquid separation. The organic phases were combined, dried over anhydrous sodium sulfate, and then filtered and concentrated under reduced pressure to give a residue. The residue was separated by prep-HPLC (Waters Xbridge Prep OBD C18 (150 mm×40 mm I.D., 10 μm); mobile phase: A: ACN, B: [$H_2O$ (containing 10 mmol $NH_4HCO_3$+0.05% $NH_3{\cdot}H_2O$], gradient: B %: 40%-60%, 8 min)) to give compound 016. MS-ESI m/z: 478.2 $[M+H]^+$. $^1H$ NMR (400 MHz, DMSO-$d_6$) δ 11.38-11.54 (m, 1H) 11.17 (br s, 1H) 8.76 (s, 1H) 8.70 (dd, J=8.4, 2.8 Hz, 1H) 7.33-7.43 (m, 1H) 7.20-7.31 (m, 2H) 7.15-7.20 (m, 1H) 6.61 (s, 1H) 5.85 (d, J=3.2 Hz, 2H) 1.37 (s, 3H) 0.75 (s, 3H).

Examples 17, 18, 19, and 20

017 or 018 or 019 or 020

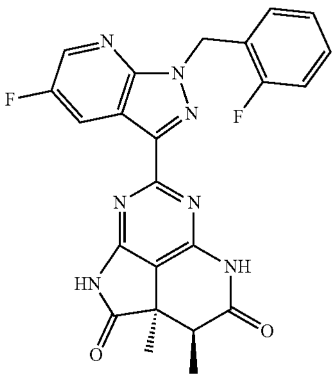

018 or 017 or 019 or 020

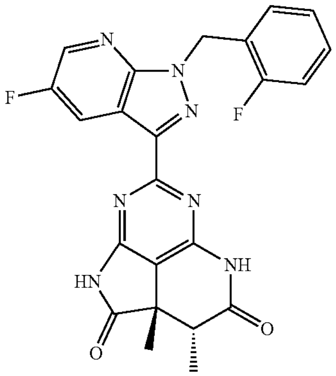

-continued
019 or 020 or 017 or 018
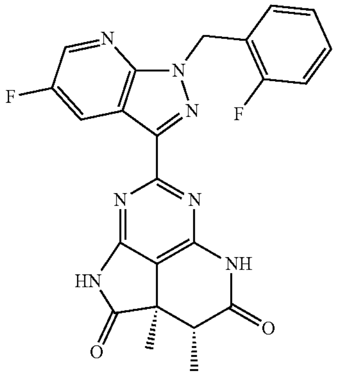
020 or 019 or 017 or 018
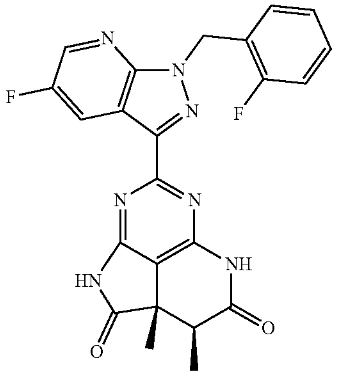
Synthetic Route:
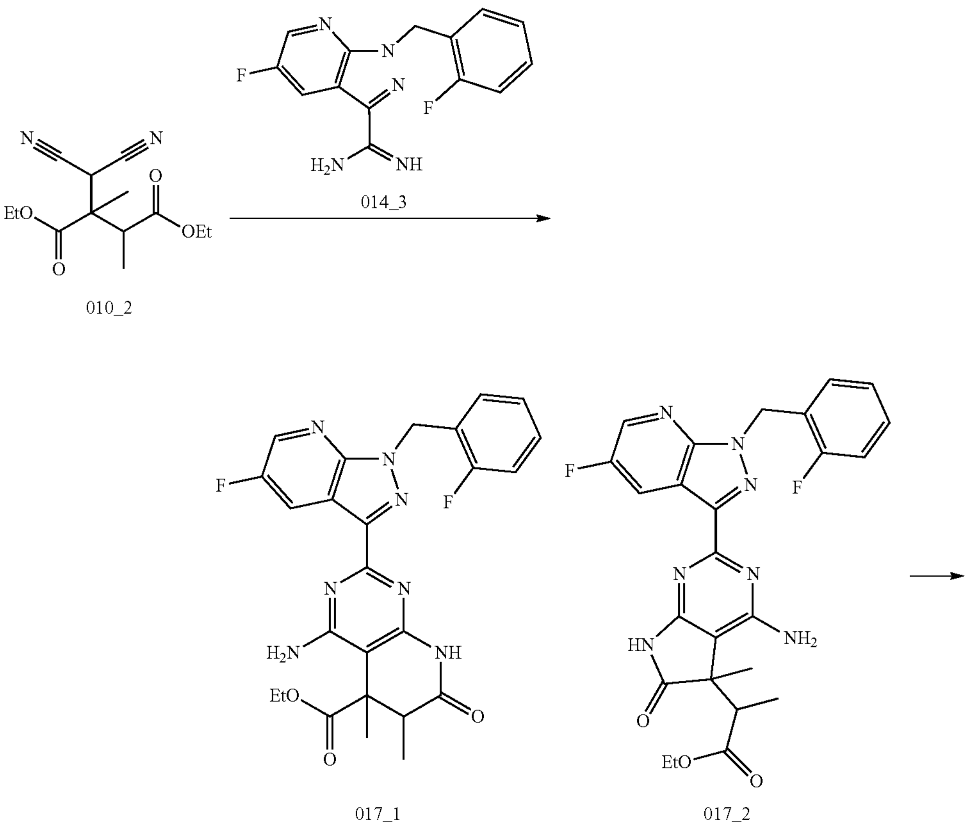

-continued

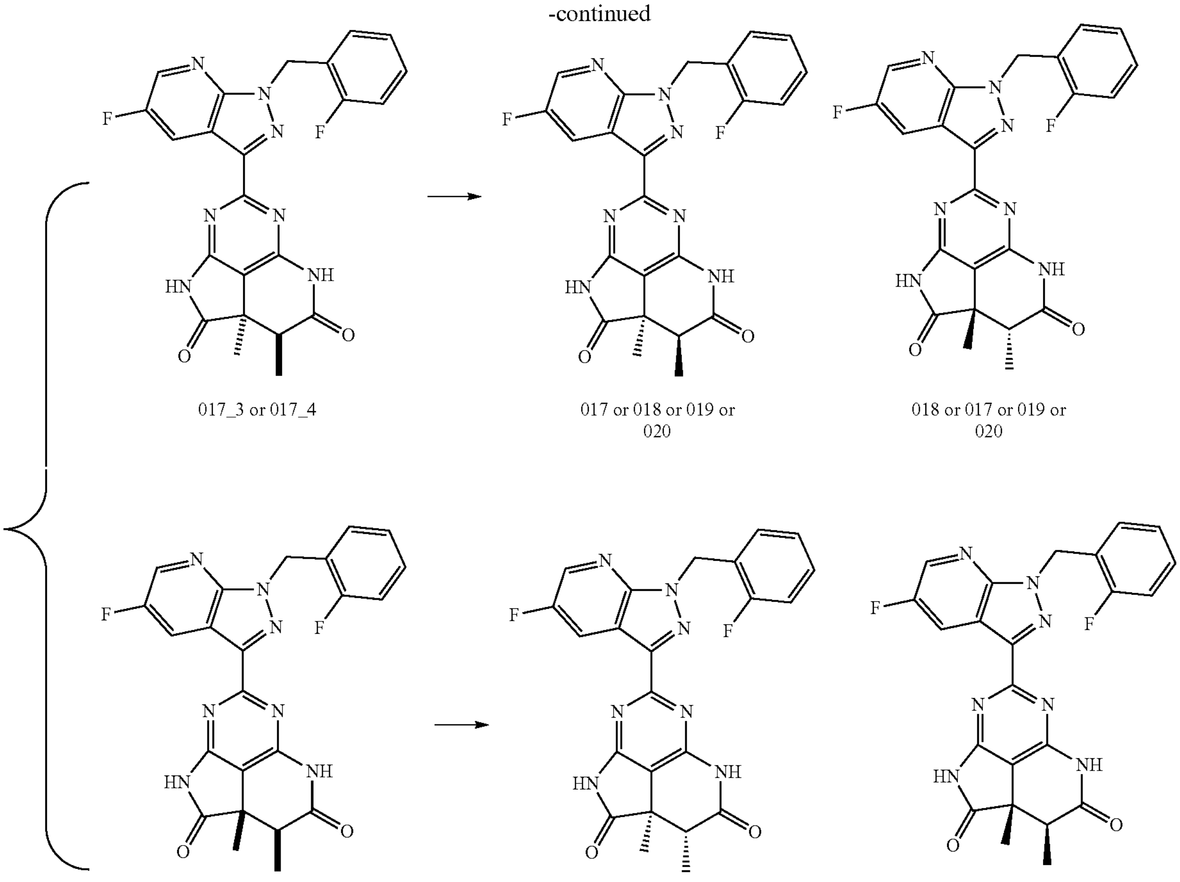

017_3 or 017_4

017 or 018 or 019 or 020

018 or 017 or 019 or 020

017_4 or 017_3

019 or 020 or 017 or 018

020 or 019 or 017 or 018

Step 1: Synthesis of Compounds 017_1 and 017_2

The hydrochloride of intermediate 014_3 (2.76 g) was added to tert-butanol (40 mL) at room temperature under nitrogen atmosphere, and then intermediate 0102 (2.72 g, 10.21 mmol) and potassium bicarbonate (2.13 g, 21.28 mmol) were added in sequence. The reaction solution was stirred at 80° C. for 12 h. After the reaction was completed, the reaction solution was cooled to room temperature and added with water (100 mL), and dimethyltetrahydrofuran (100 mL×2) was added for liquid separation. The organic phases were combined, washed with saturated brine (100 mL), dried over anhydrous sodium sulfate, and then filtered and concentrated under reduced pressure. The resulting residue was separated and purified by column chromatography (eluent: petroleum ether/ethyl acetate=1/0 to 4/1, v/v) to give intermediate 017_1 and intermediate 017_2.

Step 2: Synthesis of Compounds 017_3 and 017_4

The intermediate 017_1 (500.00 mg, 985.24 μmol) was dissolved in toluene (5 mL) at room temperature under nitrogen atmosphere. The reaction system was added with $AlMe_3$ (2 M, 1.48 mL), warmed to 75° C., and stirred for 12 h. After the reaction was completed, the reaction system was cooled to room temperature. The reaction solution was poured into water (50 mL), and diluted hydrochloric acid (1 N) was added to adjust the pH to 3-4. 2-methyltetrahydrofuran (50 mL) was added for liquid separation. The organic phase was collected, and the aqueous phase was extracted with 2-methyltetrahydrofuran (20 mL×3). The organic phases were combined, dried over anhydrous sodium sulfate, and filtered, and the filtrate was concentrated under reduced pressure to remove the solvent, thus giving a crude product. The resulting residue was separated by column chromatography (eluent: petroleum ether/ethyl acetate=1/0 to 3/1, v/v) and by prep-HPLC (column: Phenomenex luna C18 (80 mm×40 mm I.D., 3 μm); mobile phase: A: ACN, B: [$H_2O$ (containing 0.04% HCl)], gradient: B %: 33%-49%, 7 min) to give compound 017_3.

The intermediate 017_2 (700.00 mg, 1.38 mmol) was dissolved in toluene (10 mL) at room temperature under nitrogen atmosphere, and the solution was purged three times with nitrogen. The reaction system was added with $AlMe_3$ (2 M, 2.07 mL), wared to 75° C., and stirred for 12 h. After the reaction was completed, the reaction system was cooled to room temperature. The reaction system was poured into water (100 mL), and diluted hydrochloric acid (1 N) was added to adjust the pH to 3-4. 2-methyltetrahydrofuran (50 mL) was added for dilution, and liquid separation was performed. The organic phase was collected, and the aqueous phase was extracted with 2-methyltetrahydrofuran (50 mL×3). The organic phases were combined, dried over anhydrous sodium sulfate, and filtered, and the filtrate was concentrated under reduced pressure to remove the solvent, thus giving a crude product. The resulting residue was separated by column chromatography (eluent: petroleum ether/ethyl acetate=1/0 to 3/1, v/v), by prep-HPLC (mobile phase: acetonitrile/water: hydrochloric acid system: 0.04% HCl), and by prep-HPLC (column: Phenomenex luna C18 (75 mm×30 mm I.D., 3 μm); mobile phase: A: ACN, B:

[$H_2O$ (containing 10 mmol $NH_4HCO_3$+0.05% $NH_3 \cdot H_2O$)], gradient: B %: 35%-55%, 8 min) in sequence to give compound 017_4.

HPLC analysis method: column: Kinetex 5 μm C18 (2.1×50 mm); mobile phase A: $H_2O$+0.04% (v/v) TFA; mobile phase B: ACN+0.02% (v/v) TFA, gradient: B %: 10%-80%, 6 min.

017_3 (retention time: 3.482 min) MS-ESI m/z: 462.2 $[M+H]^+$. $^1H$ NMR (400 MHz, DMSO-$d_6$) δ 11.53 (s, 1H), 11.22 (s, 1H), 8.81-8.62 (m, 2H), 7.42-7.33 (m, 1H), 7.30-7.14 (m, 3H), 5.85 (s, 2H), 2.78 (q, J=7.2 Hz, 1H), 1.39 (s, 3H), 0.78 (d, J=7.4 Hz, 3H).

017_4 (retention time: 3.574 min) MS-ESI m/z: 462.2 $[M+H]^+$. $^1H$ NMR (400 MHz, DMSO-$d_6$) δ 11.14-10.77 (m, 2H), 8.76-8.73 (m, 1H), 8.72-8.67 (m, 1H), 7.41-7.34 (m, 1H), 7.28-7.20 (m, 2H), 7.19-7.13 (m, 1H), 5.84 (s, 2H), 3.09-2.99 (m, 1H), 1.28-1.19 (m, 6H).

Step 3: Synthesis of Compounds 017 and 018

Compound 017_3 (30 mg, 65.02 μmol) was separated by a chiral column (column: DAICEL CHIRALPAK IE (250 mm×30 mm, 10 μm); mobile phase: [0.1% $NH_3H_2O$ MeOH; 20%-45%, 18 min) to give compounds 017 and 018.

SFC analysis method: column: Chiralpak AS-3 (50 mm×4.6 mm I.D., 3 μm); mobile phase: A: $CO_2$, B: [MeOH (containing 0.1% IPAm)]; gradient: B %: 5%-50%, 3 min.

Compound 017 (retention time: 1.138 min): MS-ESI m/z: 462.2 $[M+H]^+$. $^1H$ NMR (400 MHz, DMSO_$d_6$) δ 11.65-11.40 (m, 1H), 11.23 (br s, 1H), 8.81-8.61 (m, 2H), 7.43-7.34 (m, 1H), 7.31-7.14 (m, 3H), 5.85 (s, 2H), 2.79 (d, J=7.4 Hz, 1H), 1.40 (s, 3H), 0.78 (d, J=7.4 Hz, 3H);

Compound 018 (retention time: 1.422 min): MS-ESI m/z: 462.2 $[M+H]^+$. $^1H$ NMR (400 MHz, DMSO_$d_6$) δ 11.71-11.01 (m, 2H), 8.83-8.64 (m, 2H), 7.42-7.35 (m, 1H), 7.31-7.13 (m, 3H), 5.85 (s, 2H), 2.78 (q, J=7.3 Hz, 1H), 1.39 (s, 3H), 0.78 (d, J=7.4 Hz, 3H).

Step 4: Synthesis of Compounds 019 and 020

Compound 017_4 (150 mg, 325.08 μmol) was separated by a chiral column (column: DAICEL CHIRALPAK IE (250 mm×30 mm, 10 μm); mobile phase: [0.1% $NH_3H_2O$ EtOH]; gradient: B %: 50%, 12 min) to give compounds 019 and 020.

SFC analysis method: column: (S,S)-WHELK-O1 (50 mm×4.6 mm I.D., 3.5 μm); mobile phase: A: $CO_2$, B: [EtOH (containing 0.1% IPAm)], gradient: B %: 5%-50%, 3 min.

Compound 019 (retention time: 1.669 min): MS-ESI m/z: 462.31 $[M+H]^+$. $^1H$ NMR (400 MHz, DMSO_$d_6$) δ: 11.38 (br s, 1H), 11.07 (s, 1H), 8.77-8.66 (m, 2H), 7.41-7.32 (m, 1H), 7.29-7.13 (m, 3H), 5.84 (s, 2H), 3.04 (q, J=7.1 Hz, 1H), 1.27-1.20 (m, 6H);

Compound 020 (retention time: 1.808 min): MS-ESI m/z: 462.34 $[M+H]^+$. $^1H$ NMR (400 MHz, DMSO_$d_6$) δ: 11.38 (br s, 1H), 11.08 (br s, 1H), 8.76-8.65 (m, 2H), 7.37 (q, J=7.1 Hz, 1H), 7.28-7.12 (m, 3H), 5.84 (s, 2H), 3.04 (q, J=6.9 Hz, 1H), 1.29-1.17 (m, 6H).

Example 21 and 22

021 or 022

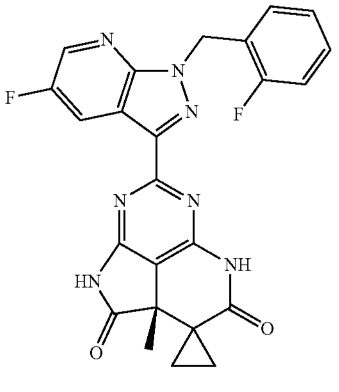

022 or 021

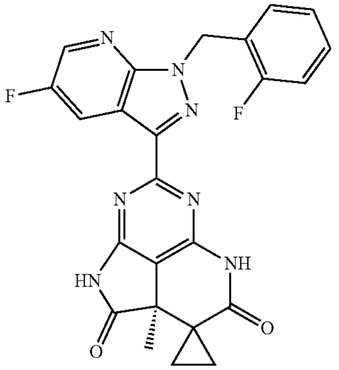

Synthetic Route:

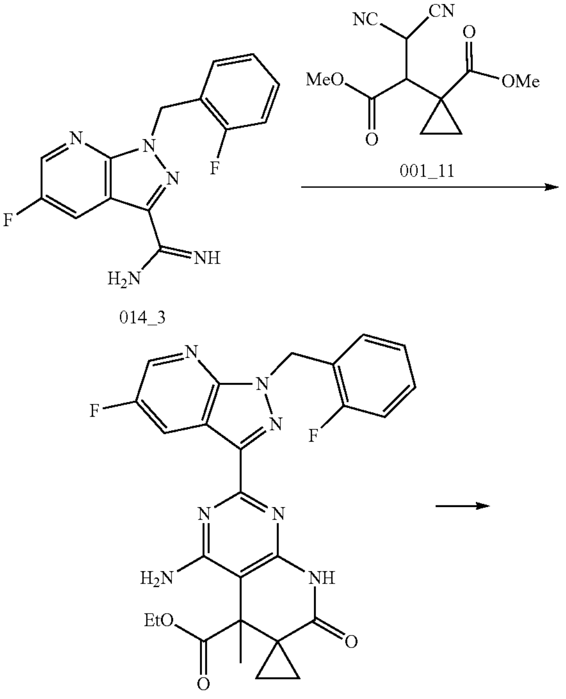

014_3

001_11

021_1

-continued

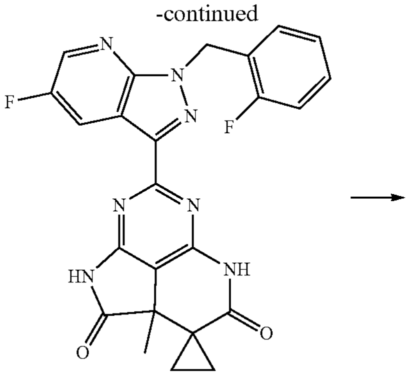

021_2

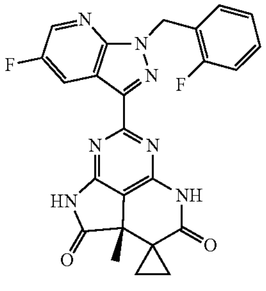

021 or 022

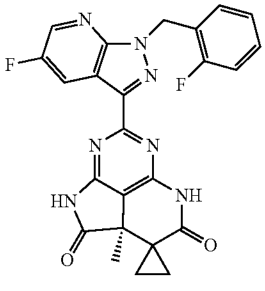

022 or 021

Step 1: Synthesis of Compound 021_1

Compound 001_11 (9.04 g, 36.14 mmol) was added to tert-butanol (100 mL) at room temperature under nitrogen atmosphere, and then the hydrochloride of compound 014_3 (5 g) and potassium carbonate (3.87 g, 38.61 mmol) were added. The reaction solution was stirred at 80° C. for 12 h. After the reaction was completed, the reaction solution was added with water (500 mL) and extracted with ethyl acetate (200 mL×3). The organic phases were combined, washed with saturated brine (100 mL×3), dried over anhydrous sodium sulfate, and then filtered and concentrated under reduced pressure to give a residue. The residue was slurried with methyl tert-butyl ether (70 mL) at room temperature and filtered, and the filter cake was collected and concentrated under reduced pressure to give compound 021_1.

Step 2: Synthesis of Compound 021_2

Compound 021_1 (4.5 g, 8.90 mmol) was dissolved in anhydrous toluene (130 mL) at room temperature under nitrogen atmosphere, and a solution of trimethylaluminum in toluene (2 M, 13.35 mL) was slowly added dropwise. The reaction system was stirred at 75° C. for 12 h. After the reaction was completed, the reaction system was cooled to room temperature, then slowly poured into water (100 mL), and added with 3 M hydrochloric acid to adjust the pH to 3-4. The mixture was extracted with dimethyltetrahydrofuran (100 mL×3). The organic phases were combined, dried over anhydrous sodium sulfate, and filtered, and the filtrate was concentrated under reduced pressure to give a residue. The residue was separated by prep-HPLC (column: Phenomenex C18 (250 mm×70 mm I.D., 10 μm); mobile phase: A: ACN, B: [$H_2O$ (containing 0.04% HCl)], gradient: B %: 40%-70%, 20 min) to give compound 021_2. $^1$H NMR (400 MHz, DMSO-$d_6$) δ: 11.50 (s, 1H), 11.28 (s, 1H), 8.78-8.68 (m, 2H), 7.44-7.34 (m, 1H), 7.30-7.19 (m, 2H), 7.20-7.12 (m, 1H), 5.85 (s, 2H), 1.58-1.49 (m, 1H), 1.44 (s, 3H), 1.18-1.08 (m, 1H), 0.82-0.62 (m, 2H).

Step 3: Synthesis of Compounds 021 and 022

Compound 021_2 (200 mg, 422.45 μmol) was separated by a chiral column (column: DAICEL CHIRALPAK AD (250 mm×30 mm, 10 μm); mobile phase: [0.1% $NH_3H_2O$ EtOH]%: 40%-40%, 8 min) to give compounds 021 and 022.

SFC analysis method: column: Chiralpak AD-3 (50 mm×4.6 mm I.D., 3 μm); mobile phase: A: $CO_2$, B: [EtOH (containing 0.1% IPAm)], gradient: B: 5%-50%, 3 min.

021 (retention time: 1.253 min) MS-ESI m/z: 474.2.0 $[M+H]^+$ $^1$H NMR (400 MHz, DMSO-$d_6$) δ 11.50 (s, 1H), 11.28 (s, 1H), 8.78 (s, 2H), 7.43-7.32 (m, 1H), 7.30-7.20 (m, 2H), 7.19-7.13 (m, 1H), 5.85 (s, 2H), 1.58-1.50 (m, 1H), 1.43 (s, 3H), 1.15-1.10 (m, 1H), 0.77-0.67 (m, 2H);

022 (retention time: 1.367 min) MS-ESI m/z: 474.2.0 $[M+H]^+$ $^1$H NMR (400 MHz, DMSO-$d_6$) δ 11.54-11.46 (m, 1H), 11.28 (s, 1H), 8.78-8.70 (m, 2H), 7.44-7.34 (m, 1H), 7.30-7.20 (m, 2H), 7.20-7.14 (m, 1H), 5.86 (s, 2H), 1.60-1.50 (m, 1H), 1.44 (s, 3H), 1.13 (ddd, J=9.2, 7.2, 4.0 Hz, 1H) 0.80-0.66 (m, 2H).

Example 23

023

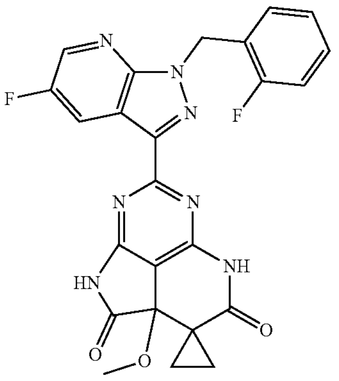

Synthetic Route:

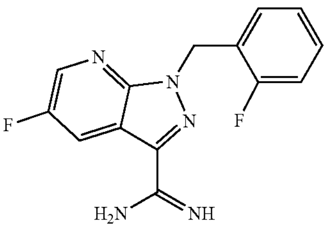

014_3

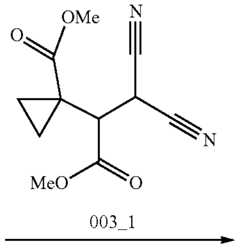

003_1

-continued

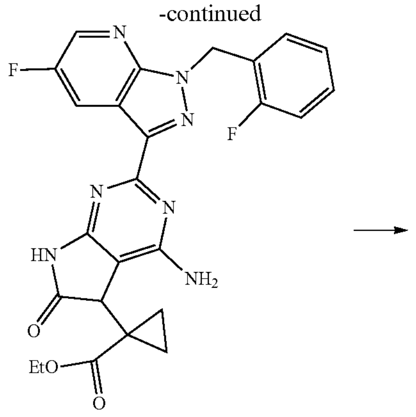

023_1

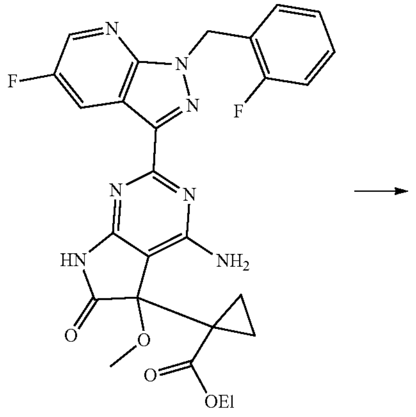

023_2

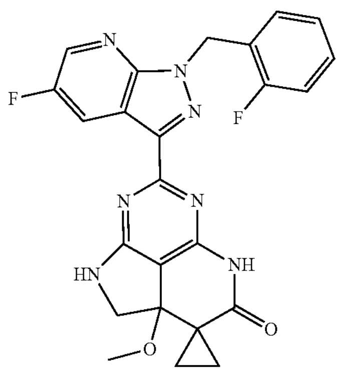

023

Step 1: Synthesis of Compound 023_

The hydrochloride of compound 014_3 (10 g, 30.89 mmol) was added to tert-butanol (150 mL) at room temperature under nitrogen atmosphere, and then compound 003_1 (14.59 g, 61.78 mmol) and potassium carbonate (7.73 g, 77.23 mmol) were added. The reaction solution was stirred at 80° C. for 12 h. After the reaction was completed, the reaction solution was added with water (500 mL) and extracted with ethyl acetate (200 mL×3). The organic phases were combined, washed with saturated brine (100 mL×3), dried over anhydrous sodium sulfate, and then filtered and concentrated under reduced pressure to give a residue. The residue was slurried with methyl tert-butyl ether (50 mL) and filtered, and the filter cake was collected and concentrated under reduced pressure to give compound 023_1.

Step 2: Synthesis of Compound 023_2

A mixture of compound 023_1 (5 g, 10.17 mmol) was added to anhydrous methanol (100 mL) at room temperature under nitrogen atmosphere, and then [bis(trifluoroacetoxy)iodo]benzene (10.94 g, 25.43 mmol) was added. The reaction solution was stirred at 50° C. for 12 h. After the reaction was completed, the reaction solution was concentrated under reduced pressure, then diluted with ethyl acetate (100 mL), and washed with saturated sodium sulfite (50 mL×3). The organic phase was dried over anhydrous sodium sulfate and then filtered and concentrated under reduced pressure to give a residue. The residue was separated by prep-HPLC (column: Phenomenex luna C18 (250 mm×100 mm I.D., 15 μm); mobile phase: A: ACN, B: [$H_2O$ (containing 0.1% TFA)], gradient: B %: 35%-65%, 20 min) to give compound 023_2.

Step 3: Synthesis of Compound 023

Compound 023_2 (0.8 g, 1.53 mmol) was dissolved in anhydrous toluene (15 mL) at room temperature under nitrogen atmosphere, and a solution of trimethylaluminum in toluene (2 M, 2.45 mL) was slowly added dropwise. After the addition, the reaction solution was stirred at 100° C. for 12 h. After the reaction was completed, the reaction system was cooled to room temperature and slowly poured into water (20 mL), 3 M hydrochloric acid was added to adjust the pH to 3-4, and the solution was extracted with dimethyltetrahydrofuran (20 mL×3). The organic phases were combined, washed with saturated brine (20 mL×2), dried over anhydrous sodium sulfate, and filtered, and the filtrate was concentrated under reduced pressure to give a residue. The resulting residue was separated by column chromatography (eluent: petroleum ether/ethyl acetate=1/0 to 3/1, v/v) and by prep-HPLC (column: Phenomenex luna C18 (80 mm×40 mm I.D., 3 μm), mobile phase: A: ACN, B: [$H_2O$ (containing 0.04% HCl)], gradient: B %: 45%-65%, 7 min) to give compound 023. MS-ESI m/z: 490.0 $[M+H]^+$. $^1H$ NMR (400 MHz, DMSO-$d_6$) δ: 11.75 (br s, 1H), 11.46 (s, 1H), 8.82-8.68 (m, 2H), 7.44-7.34 (m, 1H), 7.32-7.14 (m, 3H), 5.80-5.94 (m, 2H), 3.17 (s, 3H), 1.58-1.68 (m, 1H), 1.32-1.44 (m, 1H), 0.82-0.98 (m, 2H).

Examples 24 and 25
024 and 025
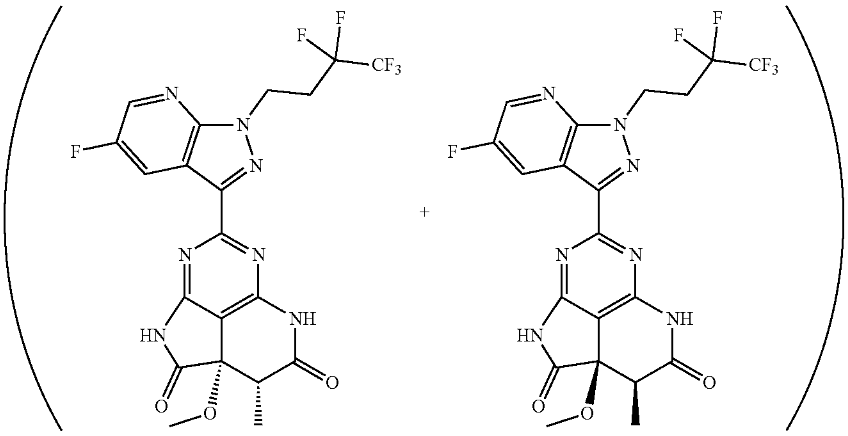
or
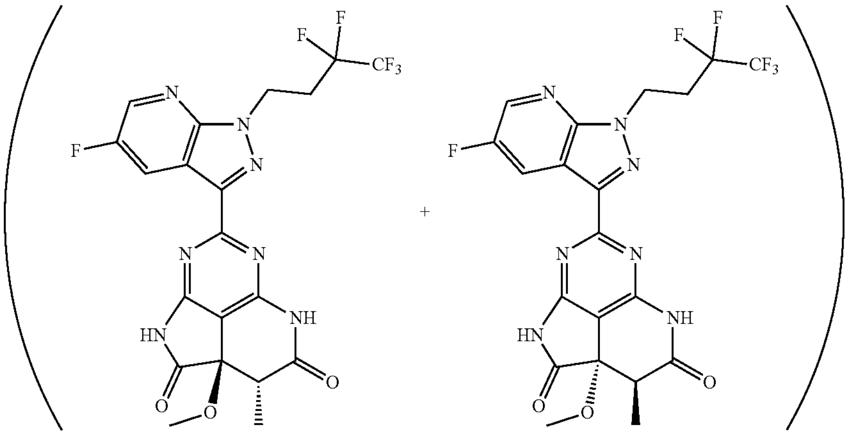
Synthetic Route:
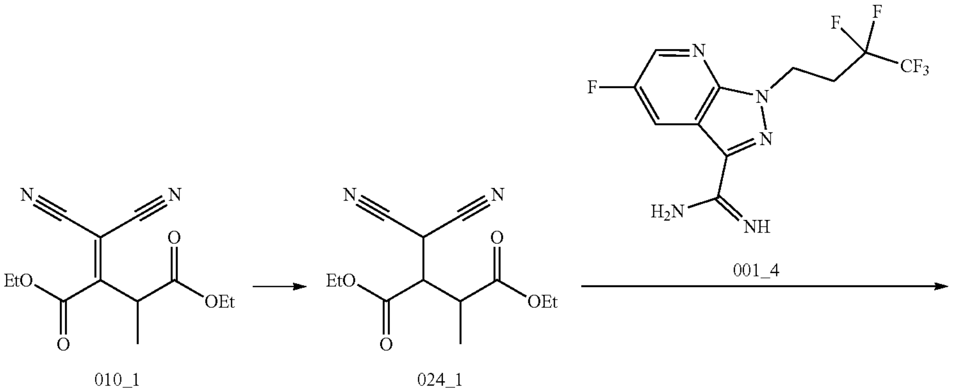

-continued
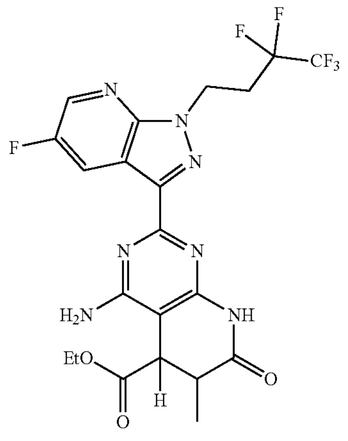
024_2
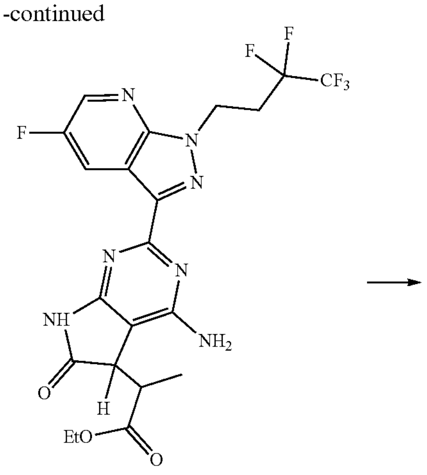
024_3
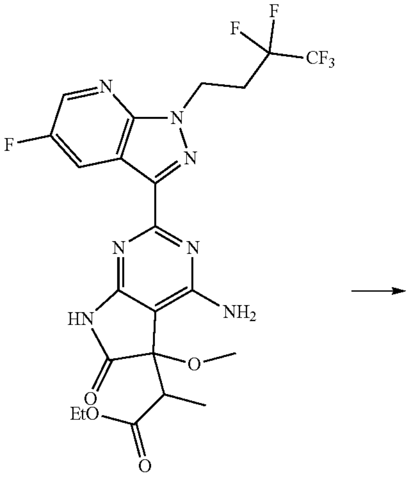
024_4
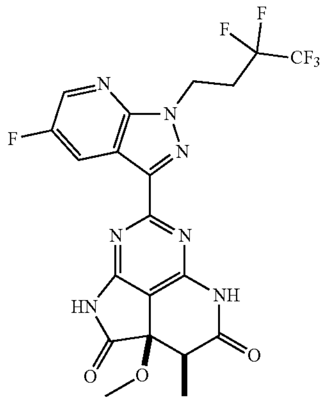
or
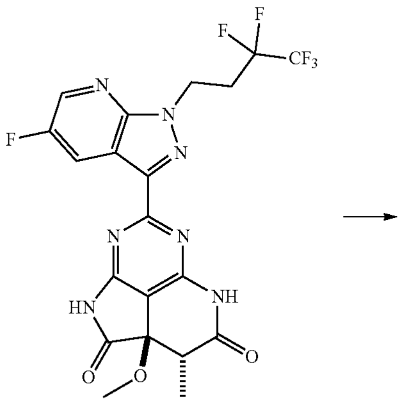
024_5

-continued

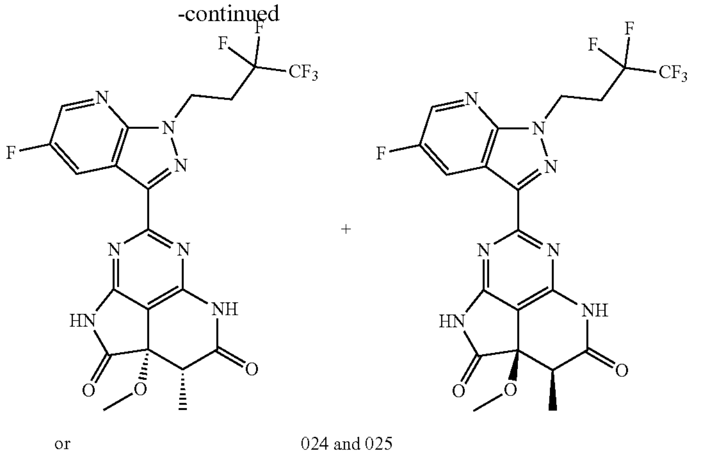

024 and 025 or

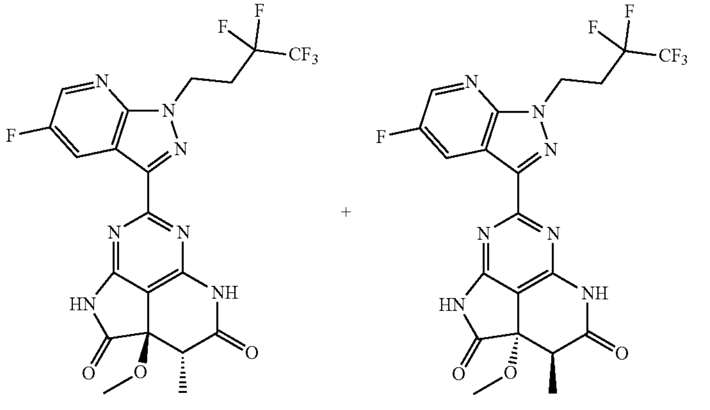

024 and 025

Step 1: Synthesis of Compound 024_1

Compound 010_1 (10 g, 39.96 mmol) was added to chloroform (40 mL) and ethanol (40 mL) at room temperature under nitrogen atmosphere, and then diethyl 2,6-dimethyl-1,4-dihydro-3,5-pyridinedicarboxylate (15.18 g, 59.94 mmol) was added. The reaction solution was stirred at 25° C. for 12 h. After the reaction was completed, the reaction solution was filtered, and the filtrate was concentrated under reduced pressure to give a residue. The resulting residue was separated by column chromatography (eluent: petroleum ether/ethyl acetate=1/0 to 4/1, v/v) to give compound 024_1.

Step 2: Synthesis of Compound 024_2

The hydrochloride of intermediate 001_4 (8.5 g) was dissolved in tert-butanol (150 mL) at room temperature under nitrogen atmosphere, and then the intermediate 024_1 (9.49 g, 37.60 mmol) and potassium bicarbonate (5.88 g, 58.75 mmol) were added. The reaction solution was stirred at 90° C. for 12 h. After the reaction was completed, the reaction solution was added to water (500 mL), and a solid was precipitated. The mixed solution was filtered, and the filter cake was washed with methyl tert-butyl ether (20 mL), collected, and dried under reduced pressure to give a mixture of compound 024_2 and compound 024_3.

Step 3: Synthesis of Compound 024_4

Compounds 024_2 and 024_3 (5 g, 9.41 mmol) were dispersed in anhydrous methanol (100 mL) at room temperature under nitrogen atmosphere, and [bis(trifluoroacetoxy)iodo]benzene (12.14 g, 28.23 mmol) was added. The reaction solution was stirred in an oil bath at 50° C. for 2 h. After the reaction was completed, the reaction solution was cooled to room temperature and concentrated to remove the solvent, thus giving an oily residue. Isopropyl ether (100 mL) was added to the residue. The mixture was stirred at room temperature for 30 min, and then a white solid was precipitated. The mixture was filtered, and the filtrate was concentrated under reduced pressure to give a crude product. The residue was separated and purified by column chromatography (eluent: petroleum ether/2-methyltetrahydrofuran=1/0 to 1/1, v/v) to give intermediate 024_4.

Step 4: Synthesis of Compound 024_5

Compound 024_4 (0.3 g, 534.34 μmol) was dissolved in anhydrous toluene (6 mL) at room temperature under nitrogen atmosphere, and a solution of trimethylaluminum in toluene (2 M, 854.95 μL) was added. The reaction system was stirred at 50° C. for 12 h, warmed to 90° C. and stirred for 12 h. After the reaction was completed, the reaction solution was cooled to room temperature. The reaction solution was poured into water (100 mL). Diluted hydrochloric acid (1 N) was added to adjust the pH to 3-4, and the reaction solution was extracted with ethyl acetate (50 mL×3). The organic phase was washed with saturated brine (20 mL), dried over anhydrous sodium sulfate, and then filtered and concentrated to give a crude product. The residue was separated by prep-HPLC (column: Phenomenex C18 (75 mm×30 mm I.D., 3 μm); mobile phase: A: ACN, B: [$H_2O$ (containing 10 mmol $NH_4HCO_3$)], gradient: B %: 35%-55%, 8 min) to give compound 024_5. MS-ESI m/z: 516.2 $[M+H]^+$. $^1H$ NMR (400 MHz, DMSO_$d_6$) δ 11.95-11.71 (m, 1H), 11.38 (br s, 1H), 8.82-8.66 (m, 2H), 4.93 (t, J=6.6 Hz, 2H), 3.19 (s, 3H), 3.01 (tt, J=6.8, 19.1 Hz, 2H), 2.89 (q, J=7.6 Hz, 1H), 0.82 (d, J=7.5 Hz, 3H).

Step 5: Synthesis of Compounds 024 and 025

Compound 024_5 (100 mg, 153.29 μmol) was separated by a chiral column (column: DAICEL CHIRALPAK AS (250 mm×30 mm, 10 μm); mobile phase: [0.1% $NH_3H_2O$ EtOH]%: 10%-10%, 12 min) to give compounds 024 and 025.

SFC analysis method: column: Chiralpak AS-3 (150 mm×4.6 mm I.D., 3 μm); mobile phase: A: $CO_2$, B: [EtOH (containing 0.1% IPAm)], gradient: B: 10%-50%, 3 min.

024 (retention time: 1.496 min) MS-ESI m/z: 515.9 $[M+H]^+$ $^1H$ NMR (400 MHz, DMSO-$d_6$) δ 11.85 (br s, 1H), 11.38 (br s, 1H), 8.77 (dd, J=1.6, 2.8 Hz, 1H), 8.71 (dd. J=2.8, 8.6 Hz, 1H), 4.93 (t, J=6.6 Hz, 2H), 3.19 (s, 3H), 3.09-2.94 (m, 2H), 2.90 (q, J=7.6 Hz, 1H), 0.95-0.74 (m, 3H);

025 (retention time: 1.789 min) MS-ESI m/z: 516.2 $[M+H]^+$ $^1H$ NMR (400 MHz, DMSO-$d_6$) δ 12.09-11.16 (m, 2H), 8.88-8.61 (m, 2H), 4.93 (t, J=6.8 Hz, 2H), 3.19 (s, 3H), 3.01 (tt, J=6.6, 19.2 Hz, 2H), 2.90 (q, J=7.6 Hz, 1H), 0.82 (d, J=7.6 Hz, 3H).

Examples 26 and 27

026 and 027

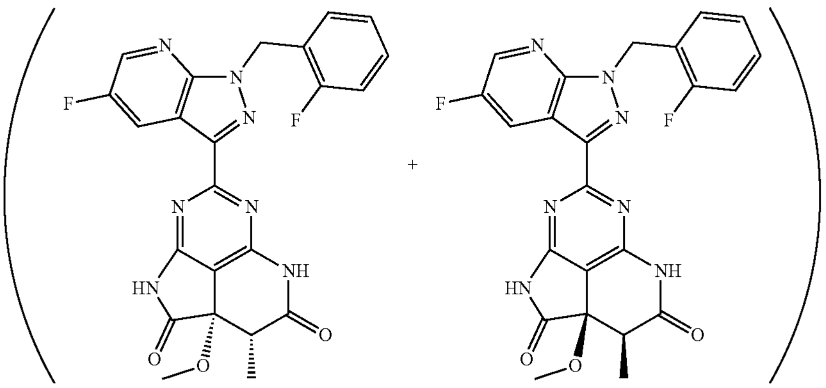

or

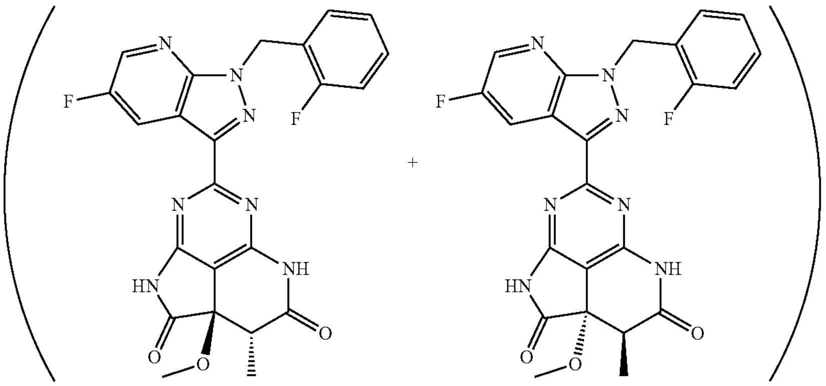

Synthetic Route:

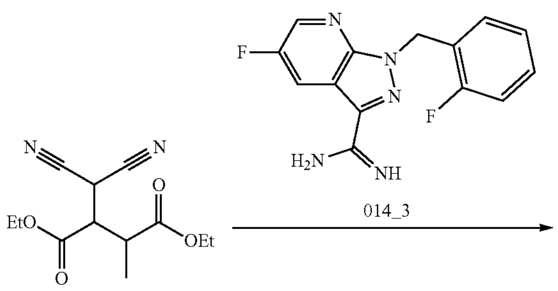

024_1

-continued
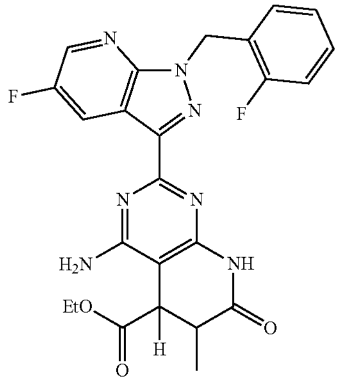
026_1
+
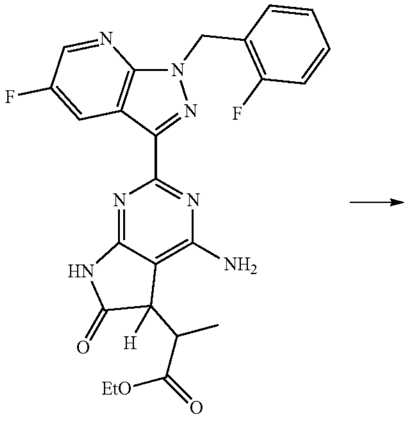
026_2
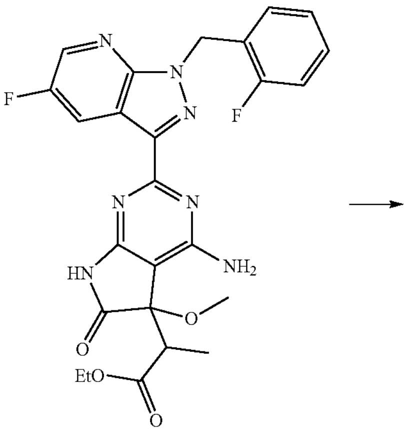
026_3
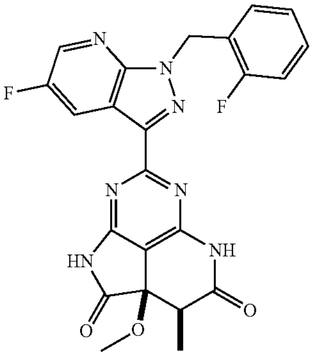
or
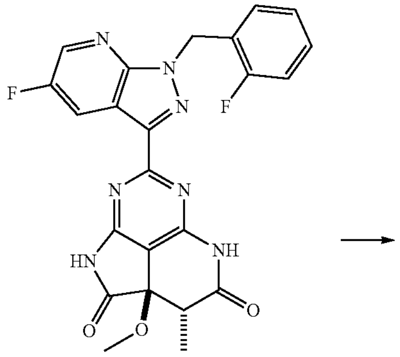
026_4
or
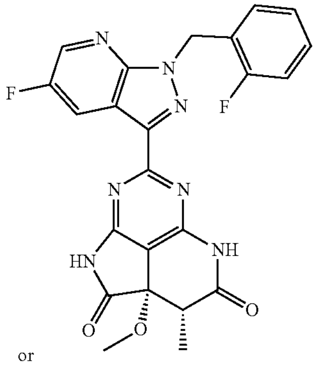
+
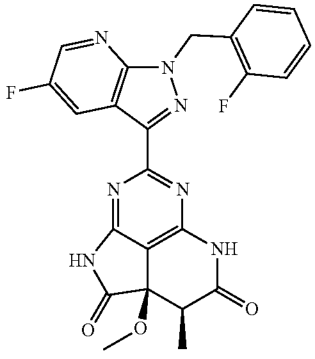

-continued

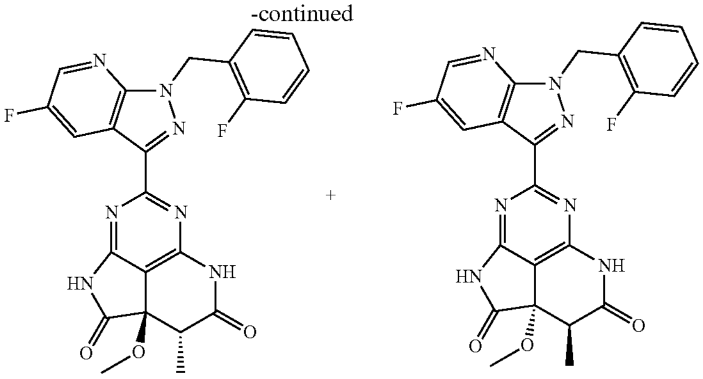

026 and 027

Step 1: Synthesis of Compound 026_1

Compound 024_1 (2.99 g, 11.86 mmol) was dissolved in tert-butanol (150 mL) at room temperature under nitrogen atmosphere, and the hydrochloride of compound 014_3 (2.4 g, 7.41 mmol) and potassium bicarbonate (1.86 g, 18.53 mmol) were added. The mixture was stirred at 85° C. for 12 h. After the reaction was completed, 2-methyltetrahydrofuran (100 mL) and water (100 mL) were added to the reaction solution, and liquid separation was performed. The aqueous phase was extracted with 2-methyltetrahydrofuran (100 mL×3). The organic phases were combined, washed with saturated brine (100 mL×3), dried over anhydrous sodium sulfate, and then filtered and concentrated under reduced pressure to give a mixture of intermediates 026_1 and 026_2.

Step 2: Synthesis of Compound 026_3

The mixture of compounds 026_1 and 026_2 (1 g, 2.03 mmol) was dispersed in anhydrous methanol (20 mL) at room temperature under nitrogen atmosphere, and [bis(trifluoroacetoxy)iodo]benzene (1.74 g, 4.05 mmol) was added. The reaction solution was stirred in an oil bath at 50° C. for 12 h. After the reaction was completed, the reaction solution was cooled to room temperature and concentrated to remove the solvent, thus giving an oily residue. The residue was separated and purified by column chromatography (eluent: petroleum ether/ethyl acetate=1/0 to 7/3, v/v) to give compound 026_3.

Step 3: Synthesis of Compound 026_4

Compound 026_3 (350 g, 668.59 μmol) was dissolved in anhydrous toluene (10 mL) at room temperature under nitrogen atmosphere, and a solution of trimethylaluminum in toluene (2 M, 1.34 mL) was added. The reaction system was stirred at 75° C. for 5 h. After the reaction was completed, the reaction solution was cooled to room temperature. The reaction solution was poured into water (50 mL), 1 N diluted hydrochloric acid was added to adjust the pH to 3-4 and the reaction solution was extracted with ethyl acetate (50 mL×3). The organic phase was washed with saturated brine (20 mL), dried over anhydrous sodium sulfate, and then filtered and concentrated to give a crude product. The residue was separated by prep-HPLC (column: Waters Xbridge BEH C18 (100 mm×30 mm I.D., 10 μm); mobile phase: A: ACN, B: [$H_2O$ (containing 10 mmol $NH_4HCO_3$)], gradient: B %: 30%-60%, 8 min) to give compound 0264.

Step 4: Synthesis of Compounds 026 and 027

Compound 026_4 (50 mg, 104.73 μmol) was separated by a chiral column (column: DAICEL CHIRALPAK IC (250 mm×30 mm, 10 μm); mobile phase: [0.1% $NH_3H_2O$ IPA]%: 45%-45%, 9 min) to give compounds 026 and 027.

SFC analysis method: column: Chiralpak IC-3 (50 mm×4.6 mm I.D., 3 μm); mobile phase: A: $CO_2$, B: [IPA (containing 0.1% IPAm)], gradient: B %: 5%-50%, 3 min.

026 (retention time: 1.369 min) MS-ESI m/z: 478.2 $[M+H]^+$ $^1H$ NMR (400 MHz, DMSO-$d_6$) δ 11.82 (br s, 1H), 11.37 (br s, 1H), 8.77 (dd, J=1.6, 2.4 Hz, 1H), 8.71 (dd, J=2.8, 8.8 Hz, 1H), 7.41-7.36 (m, 1H), 7.31-7.16 (m, 3H), 5.86 (s, 2H), 3.17 (s, 3H), 2.88 (q, J=7.6 Hz, 1H), 0.80 (d, J=7.6 Hz, 3H);

027 (retention time: 1.499 min) MS-ESI m/z: 478.2 $[M+H]^+$ $^1H$ NMR (400 MHz, DMSO-$d_6$) δ 11.82 (br s, 1H), 11.37 (br s, 1H), 8.78-8.69 (m, 2H), 7.41-7.37 (m, 1H), 7.31-7.16 (m, 3H), 5.86 (s, 2H), 3.17 (s, 3H), 2.88 (q, J=7.6 Hz, 1H), 0.80 (d, J=7.6 Hz, 3H).

Bioassays

Experimental Example 1: In Vitro Activity Assay

I. InCap Cell-Based cGMP Expression Assay

1. Procedures

1) Preparation of Solutions

10% BSA (Bovine Serum Albumin)

10 g of BSA was dissolved in 100 mL of double distilled water ($ddH_2O$) to give 10% BSA.

5 Mm Deta (Diethylenetriamine)-NO 10 mg of DETA-NO was weighed out and dissolved in 12.2 mL of double distilled water ($ddH_2O$) to give 5 mM DETA-NO, which was aliquoted and cryopreserved in a freezer at −20° C.

Washing Buffer (50 mL)

| Volume | Final concentration |
|---|---|
| 49 mL of Earle buffered saline solution (EBSS) | 1× |
| 500 μL of hydroxyethyl piperazineethanesulfonic acid (HEPES) 1M | 10 mM |
| 250 μL of 10% BSA stabilizer | 0.05% |
| 250 μL of $MgCl_2$ 1M | 5 mM |

Assay Buffer (50 mL)

| Volume | Final concentration |
|---|---|
| 48.95 mL of Earle buffered saline solution (EBSS) | 1× |
| 500 μL of hydroxyethyl piperazineethanesulfonic acid (HEPES) 1M | 10 mM |
| 250 μL of 10% BSA | 0.05% |
| 50 μL of isobutylmethylxanthine (IBMX) 500 mmol/L | 0.5 mM |
| 250 μL of $MgCl_2$ 1M | 5 mM |

Detection Buffer a) To 1 mL of a lysis buffer was added 50 μL of cGMP-D2 (D2-labeled cyclic guanosine monophosphate), and the mixture was well mixed.

b) To 1 mL of a lysis buffer was added 50 μL of anti-cGMP cryptate ($Eu^{3+}$ cryptate-labeled anti-cyclic guanosine monophosphate antibody), and the mixture was well mixed.

2) Dilution of Compounds (1) The compounds were diluted to 5 mM with DMSO, 10 μL of each of the compounds was transferred to a shallow well plate for Echo.

(2) The compounds were serially diluted with Echo. Each of the compounds was diluted to obtain 10 concentration gradients, and 50 nL of each compound at each concentration gradient was added to a 384 microwell plate.

3) Preparation of LNCap Cells (1) LNCap medium: RPMI1640+10% fetal bovine serum+1% bispecific antibody.

(2) Phosphate buffered saline, pancreatin, and the medium used in the process of cell passaging were pre-heated in a water bath at 37° C.

(3) The cells (the 14th generation) were taken out of the 37° C. 5% $CO_2$ incubator, and the old medium was pipetted off the culture flask.

(4) 5 mL of phosphate buffered saline was pipetted into the culture flask to rinse the cells, and then the liquid was discarded.

(5) 3 mL of pancreatin was pipetted into the culture flask. After the culture flask was shaken, the liquid was discarded, and the culture flask was placed in the incubator.

(6) After about 2 min, the culture flask was taken out. After all the cells were observed to be isolated, 9 mL of the medium was pipetted into the culture flask and the mixture was pipetted several times. The cell suspension was transferred to a 50 mL centrifuge tube.

(7) 0.7 mL of the cell suspension was pipetted into a counter cup and the cells were counted on a ViCell XR. The remaining cells were centrifuged at 1000 rpm for 5 min, and the supernatant was removed.

(8) The cells were washed by adding 10 mL of the washing buffer and centrifuged at 1000 rpm for 5 min, and the supernatant was removed.

(9) The assay buffer was added to adjust the cell concentration to $1.25\times10^6$/mL. The cells were added to the microwell plate at 8 μL/well.

4) Formulation and Addition of DETA-NO (1) 10 μL of 5 mM DETA-NO was added to 1240 μL of the assay buffer and to 1657 μL of the assay buffer to give 40 μM DETA-NO and 30 μM DETA-NO, respectively.

(2) DETA-NO was transferred to the 384 microwell plate at 2 μL/well using Bravo.

(3) The mixtures were centrifuged at 1500 rpm for 5 min. The microwell plate was incubated at 37° C. for 30 min.

5) Preparation of cGMP Standard Curve (1) 1 mM of the cGMP stock solution was diluted to 10 μM with the assay buffer. Then 4-fold serial dilution was performed to obtain 11 concentration gradients.

(2) The cGMP dilutions were added to the microwell plate at 10 μL/well.

6) Addition of Detection Reagents and Plate Reading (1) cGMP-D2 was transferred to the 384 microwell plate at 5 μL/well using Bravo. The mixtures were centrifuged at 1500 rpm for 1 min.

(2) The anti-cGMP cryptate was transferred to the 384 microwell plate at 5 μL/well using Bravo. The mixtures were centrifuged at 1500 rpm for 1 min.

(3) The plate was incubated at room temperature for 1 h.

(4) 665/615 was read using envision.

7) Data Analysis (1) cGMP standard curve: a standard curve was generated using Graphpad prism based on the cGMP concentrations and 665/615 ratios.

(2) Conversion of HTRF (homogeneous time-resolved fluorescence) ratios (665/615) to cGMP concentrations: in Graphpad prism, the HTRF ratios (665/615) were copied into the ratio column of the cGMP standard cure, and the "Log inhibitor vs response-variable slope" analysis was run with "interpolate" selected to convert the HTRF ratios (665/615) to cGMP concentrations.

(3) Compound activation curve: a curve was generated using the "Log agonist vs response-variable slope" analysis method in Graphpad prism based on the cGMP concentrations obtained by the conversion and the compound concentrations.

MEC values of the stimulating activity of the compounds disclosed herein for sGC are shown in Table 1.

TABLE 1

MEC values of the stimulating activity of the compounds disclosed herein for sGC

| Compound | MEC (nM) |
|---|---|
| 001 | 71.4 |
| 002 | 74.1 |
| 003 | 240 |
| 004 | 673 |
| 006 | 214 |
| 007 | 548 |
| 008 | 729 |
| 010 | 62.6 |
| 011 | 56.3 |
| 012 | 101 |
| 013 | 140.5 |
| 016 | 19.3 |
| 024 | 64.5 |
| 025 | 128.4 |
| 026 | 9.2 |
| 027 | 10.2 |

MEC: minimum effective concentration to stimulate cGMP production (three times greater than the basal value) in lnCap cells.

Conclusion: The compounds disclosed herein can effectively stimulate sGC, significantly increasing the cGMP level.

Experimental Example 2: In Vivo Pharmacokinetic Property Study

Objective: This study was intended to determine the pharmacokinetic parameters of the compounds in male SD rats.

Experimental Materials:

Sprague Dawley rats (Male, 200-300 g, 7-9 weeks old, Shanghai SLAC)

Procedures:

In the project, 4 male SD rats were used. One group of 2 SD rats were dosed by intravenous injection at 0.3 mg/kg, 0.15 mg/mL and another group of 2 SD rats were orally dosed at 1 mg/kg, 0.2 mg/mL. Plasma samples were collected at 0.083 h (the intravenous injection group only), 0.25 h, 0.5 h, 1 h, 2 h, 4 h, 6 h, 8 h, 12 h, and 24 h after the dosing and then subjected to LC-MS/MS analysis, and data were recorded. Relevant pharmacokinetic parameters were calculated using the Phoenix WinNonlin 6.3 software based on the recorded data.

The results are shown in Table 2.

TABLE 2

| In Vivo Pharmacokinetic Results | | | | |
|---|---|---|---|---|
| Test sample | | 006 | 013 | 024 |
| iv (0.3 mg/kg) | Cl (mL/min/kg) | 4.58 | 5.55 | 5.25 |
| | $V_{dss}$ (L/kg) | 2.36 | 2.65 | 1.39 |
| | $T_{1/2}$ (h) | 6.28 | 4.91 | 3.3 |
| po (1 mg/kg) | $T_{1/2}$ (h) | 6.7 | 5.2 | 2.62 |
| | % F | 65% | 34% | 84.8% |

Conclusion: The compounds disclosed herein have good apparent volume of distribution and half-life.

Experimental Example 3: Tissue Distribution Test: Tissue Distribution Study in Animals Objective: This study was intended to test the distribution ratio of the compounds in plasma, heart, cerebrospinal fluid, and brain tissue in the case of oral administration.

Experimental Materials:

Sprague Dawley Rats (Male, 200-300 g, 7-9 Weeks Old, Shanghai SLAC)

Procedures:

In the project, 6 male SD rats were orally dosed at 1 mg/kg, 0.2 mg/mL. Samples of cerebrospinal fluid, brain, heart tissue, and plasma were collected at 2 h, 6 h, and 12 h after the dosing and then subjected to LC-MS/MS analysis, and data were recorded. Relevant pharmacokinetic parameters were calculated using the Phoenix WinNonlin 6.3 software based on the recorded data.

The results are shown in Table 3.

TABLE 3

| In vivo tissue distribution results | | | |
|---|---|---|---|
| Test sample | | 006 $AUC_{0-last}$ (h*nmol/L or h*nmol/kg) | 013 $AUC_{0-last}$ (h*nmol/L or h*nmol/kg) |
| po (1 mg/kg) | Cerebrospinal fluid | ND | ND |
| | Brain homogenate | ND | ND |
| | Heart | 6970 | 5599 |
| | Plasma | 1889 | 1369 |

ND: below the limit of detection.

Conclusion: The compounds disclosed herein have no risk of entering the brain and have good distribution in the heart.

The invention claimed is:

1. A compound of formula (I), a stereoisomer thereof, or a pharmaceutically acceptable salt thereof, (I)

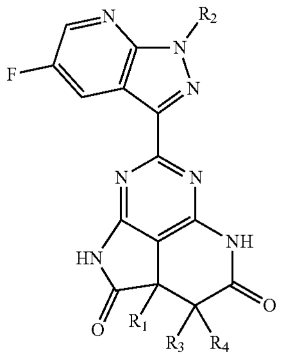

wherein, $R_1$ is selected from the group consisting of $C_{1-3}$ alkoxy, and $C_{1-3}$ alkylamino;

$R_2$ is selected from the group consisting of benzyl and $C_{1-8}$ alkyl, the benzyl or $C_{1-8}$ alkyl being optionally substituted with 1, 2, 3, 4, or 5 halogen atoms; and $R_3$ and $R_4$ are each independently selected from the group consisting of H and $C_{1-3}$ alkyl; or $R_3$, $R_4$, and an atom to which they are both connected form $C_{3-6}$ cycloalkyl.

2. The compound, the stereoisomer thereof, or the pharmaceutically acceptable salt thereof according to claim 1, wherein $R_1$ is $C_{1-3}$ alkoxy.

3. The compound, the stereoisomer thereof, or the pharmaceutically acceptable salt thereof according to claim 1, wherein $R_2$ is selected from the group consisting of benzyl and $C_{1-4}$ alkyl, the benzyl or $C_{1-4}$ alkyl is selected from the group consisting of benzyl and $C_{1-4}$ alkyl, the benzyl or $C_{1-4}$ alkyl being optionally substituted with 1, 2, 3, 4 or 5 F atoms.

4. The compound, the stereoisomer thereof, or the pharmaceutically acceptable salt thereof according to claim 1, wherein $R_3$ and $R_4$ are each independently selected from the group consisting of H, methyl, ethyl, n-propyl, and isopropyl, or $R_3$, $R_4$, and an atom to which they are both connected form cyclopropyl.

5. The compound, the stereoisomer thereof, or the pharmaceutically acceptable salt thereof according to claim 1, wherein the structural unit

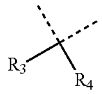

is selected from the group consisting of

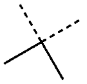,
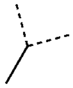,
and
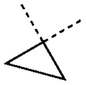.

6. The compound, the steroisomer thereof, or the pharmaceutically acceptable salt thereof according to claim 1, wherein the compound is selected from the group consisting of:
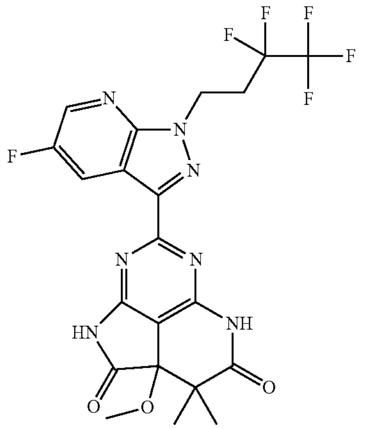 [SMILES: COC12C(=O)Nc3nc(-c4nn(CCC(F)(F)C(F)(F)F)c5ncc(F)cc45)nc(c31)NC(=O)C2(C)C]
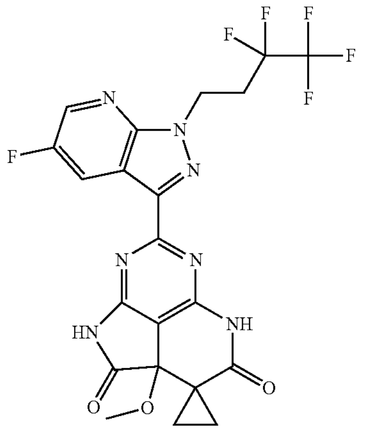
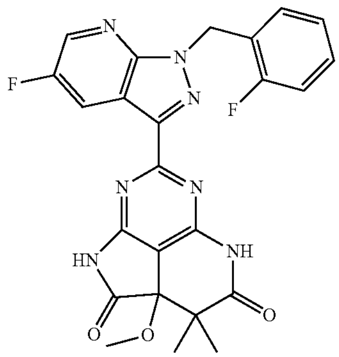
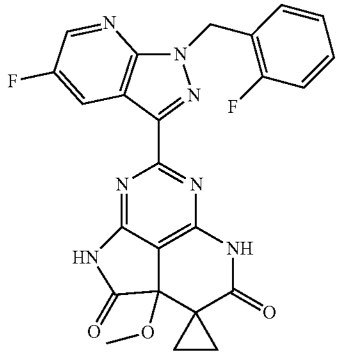
-continued
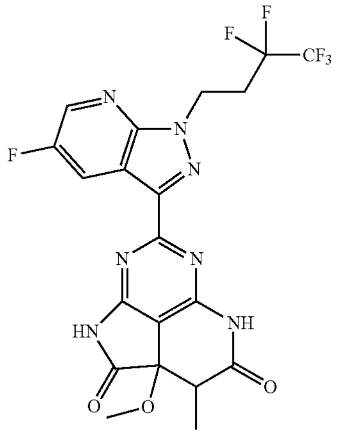
and
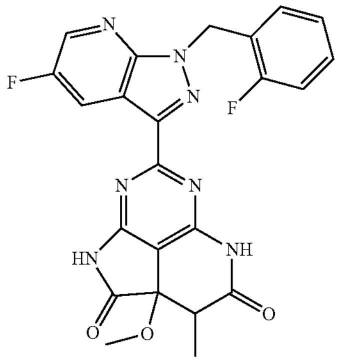
.
7. The compound, the steroisomer thereof, or the pharmaceutically acceptable salt thereof according to claim 1, wherein the compound is selected from the group consisting of:
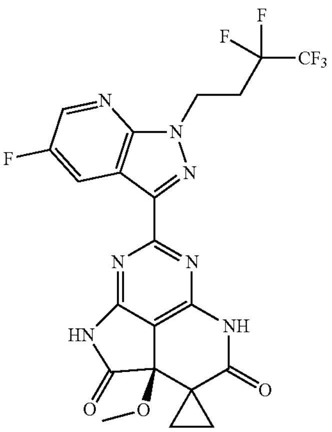

-continued
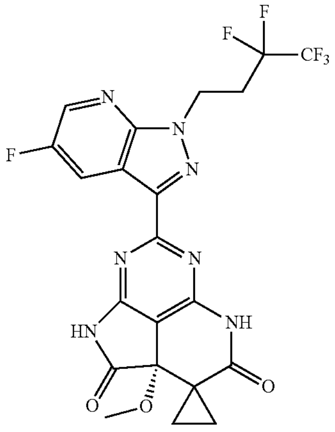
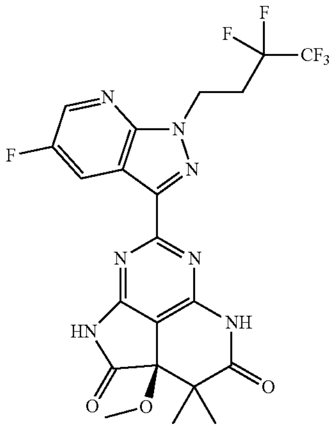
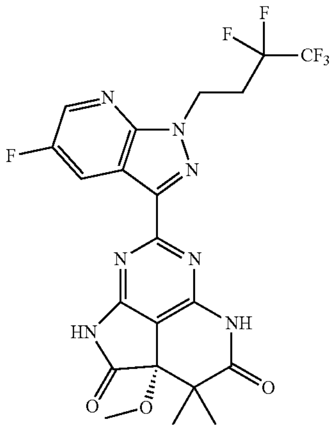
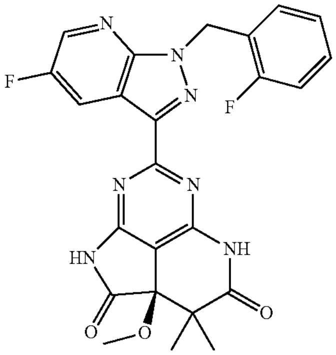
-continued
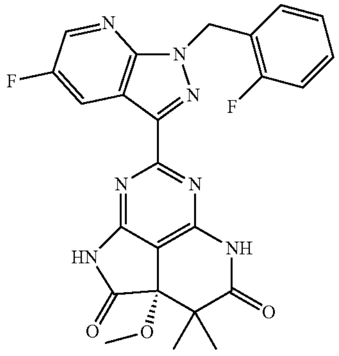
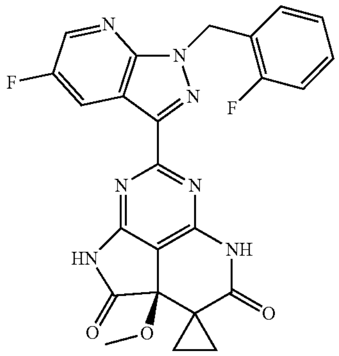
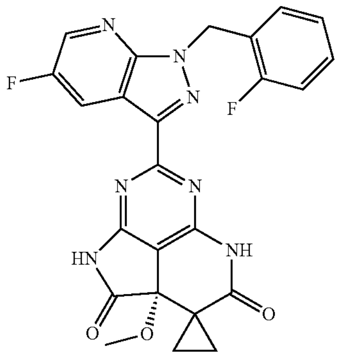
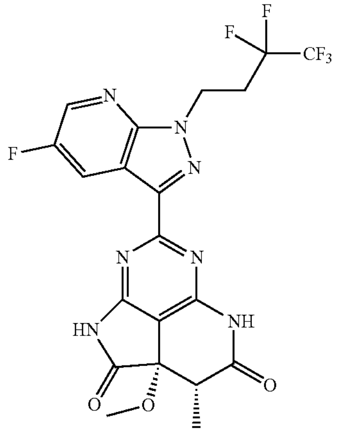

-continued

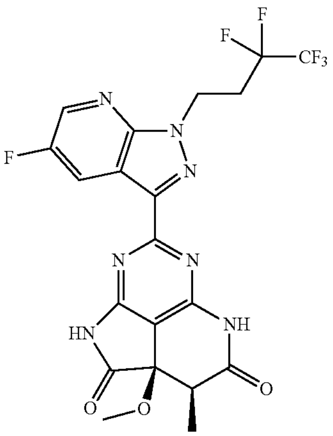

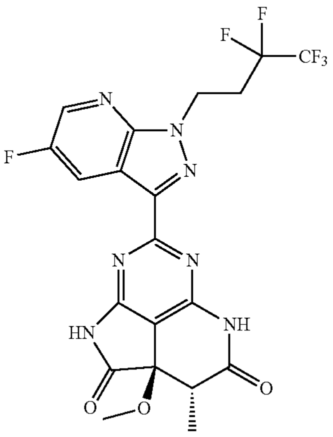

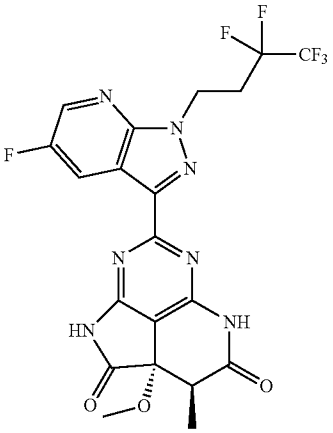

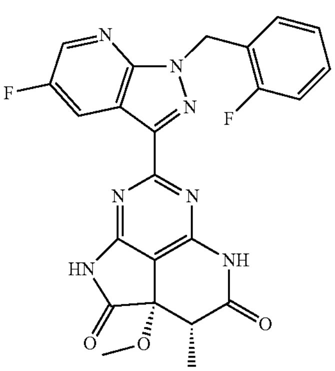

-continued

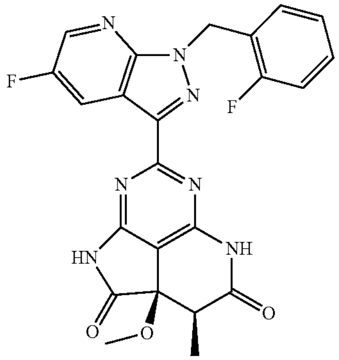

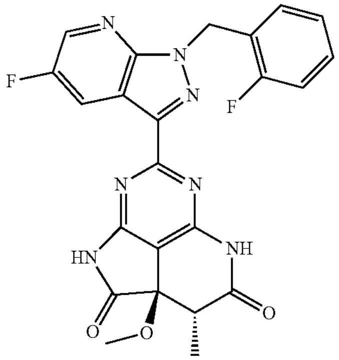

and

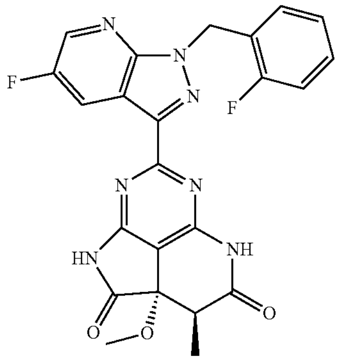

.

8. A pharmaceutical composition, comprising the compound, the stereoisomer thereof, or the pharmaceutically acceptable salt thereof according to claim 1.

9. A method for treating a sGC agonist or stimulator-associated disease, comprising administering an effective amount of the compound, the stereoisomer thereof, or the pharmaceutically acceptable salt thereof according to claim 1 to a subject in need thereof, wherein the sGC agonist or stimulator-associated disease is selected from the group consisting of heart failure and hypertension.

10. The compound, the stereoisomer thereof, or the pharmaceutically acceptable salt thereof according to claim 1, wherein $R_2$ is selected from the group consisting of

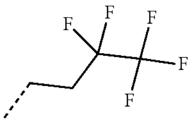

and

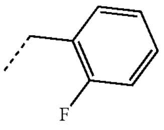

.

11. A compound of formula (I), a stereoisomer thereof, or a pharmaceutically acceptable salt thereof,

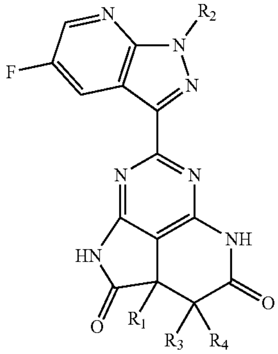

(I)

wherein, $R_1$ is selected from the group consisting of H, —OH, $C_{1-3}$ alkyl, $C_{1-3}$ alkoxy, and $C_{1-3}$ alkylamino;

$R_2$ is selected from the group consisting of benzyl and $C_{1-8}$ alkyl, the benzyl or $C_{1-8}$ alkyl being optionally substituted with 1, 2, 3, 4, or 5 halogen atoms; and $R_3$, $R_4$, and an atom to which they are both connected form $C_{3-6}$ cycloalkyl.

12. The compound, the stereoisomer thereof, or the pharmaceutically acceptable salt thereof according to claim 11, wherein $R_1$ is selected from the group consisting of H, —OH, $C_{1-3}$ alkyl, and $C_{1-3}$ alkoxy.

13. The compound, the stereoisomer thereof, or the pharmaceutically acceptable salt thereof according to claim 11, wherein $R_2$ is selected from the group consisting of benzyl and $C_{1-4}$ alkyl, the benzyl or $C_{1-4}$ alkyl being optionally substituted with 1, 2, 3, 4, or 5 F, Cl, or Br atoms.

14. The compound, the stereoisomer thereof, or the pharmaceutically acceptable salt thereof according to claim 11, wherein $R_2$ is selected from the group consisting of

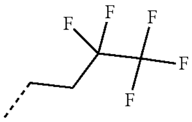

and

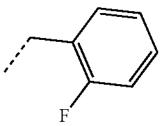

.

15. The compound, the stereoisomer thereof, or the pharmaceutically acceptable salt thereof according to claim 11, wherein the structural unit

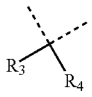

is

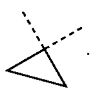

.

16. The compound, the stereoisomer thereof, or the pharmaceutically acceptable salt thereof according to claim 11, wherein the compound is selected from the group consisting of:

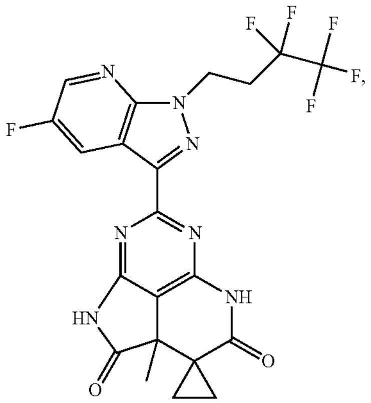

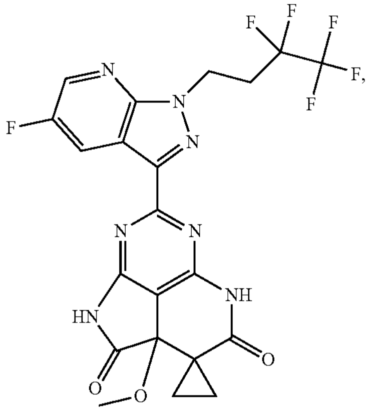

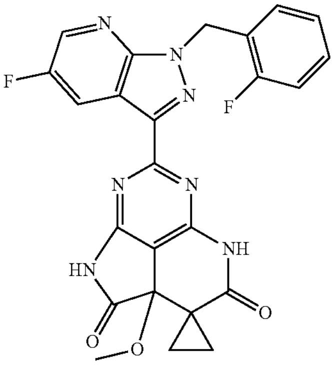

and

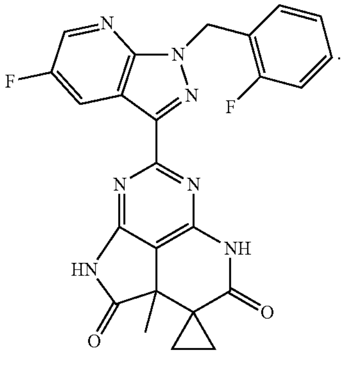

.

17. The compound, the stereoisomer thereof, or the pharmaceutically acceptable salt thereof according to claim 11, wherein the compound is selected from the group consisting of:
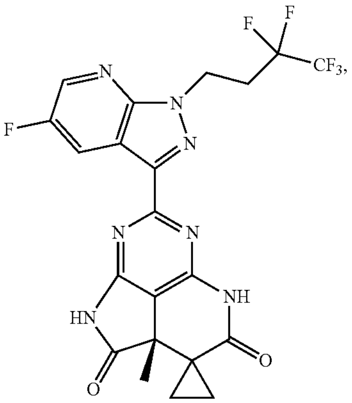
,
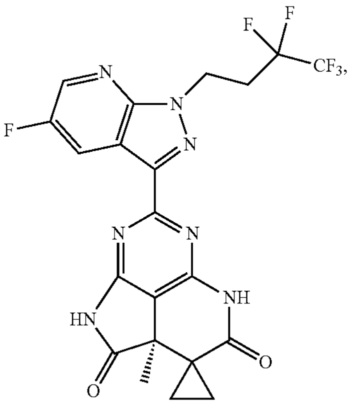
,
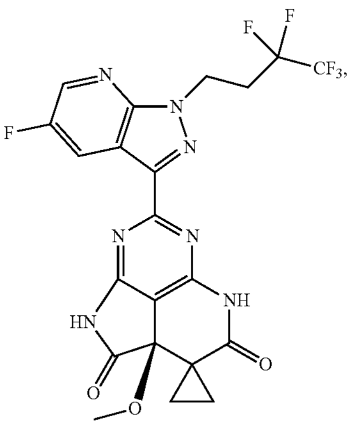
,
-continued
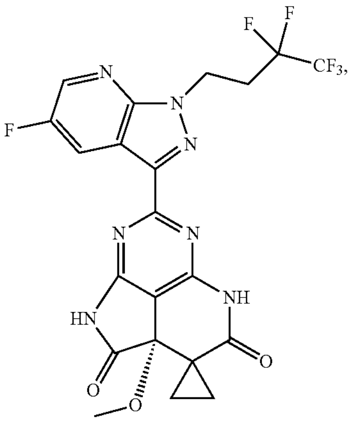
,
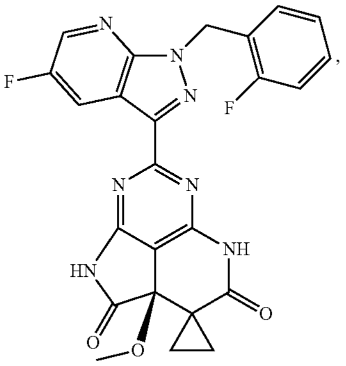
,
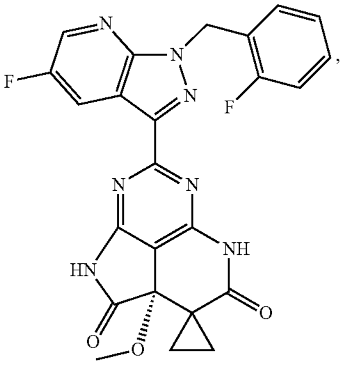
,
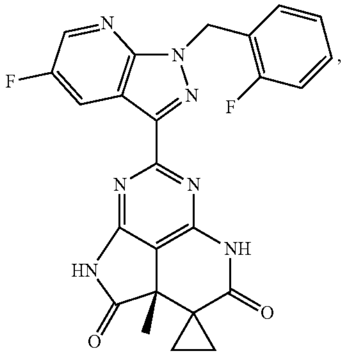
, and -continued

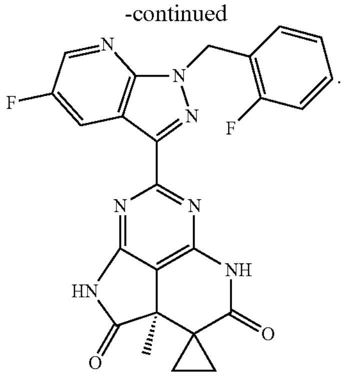

18. A pharmaceutical composition, comprising the compound, the stereoisomer thereof, or the pharmaceutically acceptable salt thereof according to claim 11.

19. A method for treating an sGC agonist or stimulator-associated disease, comprising administering an effective amount of the compound, the stereoisomer thereof, or the pharmaceutically acceptable salt thereof according to claim 11 to a subject in need thereof, wherein the sGC agonist or stimulator-associated disease is selected from the group consisting of heart failure and hypertension.

* * * * *